US011752115B2

(12) United States Patent
Pinna et al.

(10) Patent No.: US 11,752,115 B2
(45) Date of Patent: Sep. 12, 2023

(54) PPAR-ALPHA AGONIST TREATMENT OF NEUROPSYCHIATRIC DISORDERS

(71) Applicant: THE BOARD OF TRUSTEES OF THE UNIVERSITY OF ILLINOIS, Urbana, IL (US)

(72) Inventors: Graziano Pinna, Chicago, IL (US); Andrea Locci, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 416 days.

(21) Appl. No.: 16/014,607

(22) Filed: Jun. 21, 2018

(65) Prior Publication Data

US 2018/0369171 A1 Dec. 27, 2018

Related U.S. Application Data

(60) Provisional application No. 62/523,015, filed on Jun. 21, 2017.

(51) Int. Cl.
| | |
|---|---|
| *A61K 31/16* | (2006.01) |
| *A61P 25/22* | (2006.01) |
| *A61P 25/24* | (2006.01) |
| *A61K 31/216* | (2006.01) |
| *A61K 31/505* | (2006.01) |
| *A61K 31/402* | (2006.01) |
| *A61K 31/403* | (2006.01) |
| *A61K 31/421* | (2006.01) |
| *A61K 31/422* | (2006.01) |
| *A61K 31/045* | (2006.01) |
| *A61K 31/192* | (2006.01) |

(52) U.S. Cl.
CPC ............. *A61K 31/16* (2013.01); *A61P 25/22* (2018.01); *A61P 25/24* (2018.01); *A61K 31/045* (2013.01); *A61K 31/192* (2013.01); *A61K 31/216* (2013.01); *A61K 31/402* (2013.01); *A61K 31/403* (2013.01); *A61K 31/421* (2013.01); *A61K 31/422* (2013.01); *A61K 31/505* (2013.01); *A61K 2300/00* (2013.01)

(58) Field of Classification Search
CPC .. A61K 2300/00; A61K 31/16; A61K 31/216; A61K 31/045; A61K 31/192; A61K 31/402; A61K 31/403; A61K 31/421; A61K 31/422; A61K 31/505; A61P 25/22; A61P 25/24
See application file for complete search history.

(56) References Cited

U.S. PATENT DOCUMENTS

| | | | |
|---|---|---|---|
| 2005/0101542 A1 | 5/2005 | Piomelli et al. | |
| 2008/0103165 A1* | 5/2008 | Barlow | A61K 31/19 514/297 |
| 2008/0103209 A1 | 5/2008 | Piomelli et al. | |

OTHER PUBLICATIONS

Pibiri et al., PNAS Apr. 8, 2008, vol. 105, No. 14, pp. 5567-5572 (Year: 2008).*
Gm et al., J. Neuroendocrinol. Jul. 2011:23(7): 591-600. (Year: 2011).*
Wilker et al., Psycho-neuroendocrinology 67 (2016) 198-203. (Year: 2016).*
Alexander, P & T Jan. 2012, vol. 37, No. 1, pp. 32-38. (Year: 2012).*
Locci et al., 165.19 / RR32—Stimulation of the endocannabinoid system by PEA engages neurosteroid biosynthesis to improve anxiety and fear in a PTSD mouse model, Session 165 Animal Models of Trauma, Stress and Anxiety I, 2017.
Verme et al., The Nuclear Receptor Peroxisome Proliferator-Activated Receptor-α Mediates the Anti-Inflammatory Actions of Palmitoylethanolamide, Accelerated Communication, vol. 67, No. 1, p. 15-19, 2005.
Hauer et al., Plasma Concentrations of Endocannabinoids and Related Primary Fatty Acid Amides in Patients with Post-Traumatic Stress Disorder, PLOS One, vol. 8, Issue 5, p. 1-11, 2013.
Hillard, Circulating Endocannabinoids: From Whence Do They Come and Where are They Going?, Neuropsychopharmacology Reviews, 43, p. 155-17, 2018.
Darmani et al., Involvement of the cannabimimetic compound, N-palmitoyl-ethanolamine, in inflammatory and neuropathic conditions: Review of the available pre-clinical data, and first human studies, Neuropharmacology 48, 1154-1163, 2005.
Ghazizadeh-Hashemi et al., Palmitoylethanolamide as adjunctive therapy in major depressive disorder: A double-blind, randomized and placebo-controlled trial, Journal of Affective Disorders 232, 127-133, 2018.
Esmaeili et al., Preferential PPAR-α activation reduces neuroinflammation, and blocks neurodegeneration in vivo, Human Molecular Genetics, vol. 25, No. 2 317-327, 2016.

(Continued)

*Primary Examiner* — Jean P Cornet
(74) *Attorney, Agent, or Firm* — Thomas | Horstemeyer, LLP

(57) ABSTRACT

Described herein are PPARα agonists, including, but not limited to, endocannabinoids that can be used for treatment of a neuropsychiatric disorder and/or symptom thereof. Also described herein are pharmaceutical formulations containing an effective amount of a PPARα agonists, including but not limited to endocannabinoids, where the effective amount is effective for treating a neuropsychiatric disorder and/or symptom thereof. Also described herein are methods of treating a neuropsychiatric disorder and/or a symptom thereof in a subject in need thereof.

8 Claims, 30 Drawing Sheets

(56) References Cited

OTHER PUBLICATIONS

Hill et al., Is there a role for the endocannabinoid system in the etiology and treatment of melancholic depression?, Behavioural Pharmacology, vol. 16 No. 5 & 6, p. 333-352 2005.

Yehuda et al., Epigenetic biomarkers as predictors and correlates of symptom improvement following psychotherapy in combat veterans with PTSD, frontiers in Psychiatry, vol. 4, Article 118, p. 1-14, 2013.

Racke et al., PPARs in Neuroinflammation, Hindawi Publishing Corporation PPAR Research, vol. 2008, p. 1-2, 2008.

Melis et al., PPARα Regulates Cholinergic-Driven Activity of Midbrain Dopamine Neurons via a Novel Mechanism Involving α7 Nicotinic Acetylcholine Receptors, The Journal of Neuroscience, 33(14):6203-6211, 2013.

Le-Niculescu et al., Identifying blood biomarkers for mood disorders using convergent functional genomics, Molecular Psychiatry, 14, 156-174, 2009.

Redei et al., Blood transcriptomic biomarkers in adult primary care patients with major depressive disorder undergoing cognitive behavioral therapy, Citation: Transl Psychiatry, 4, p. 1*-7, 2014.

Papakostas et al., Assessment of a multi-assay, serum-based biological diagnostic test for major depressive disorder: a Pilot and Replication Study, Molecular Psychiatry 18, 332-339, 2013.

* cited by examiner

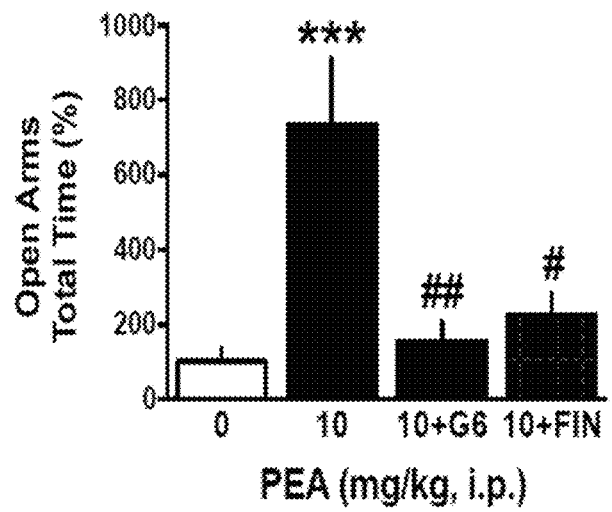
FIG. 3D
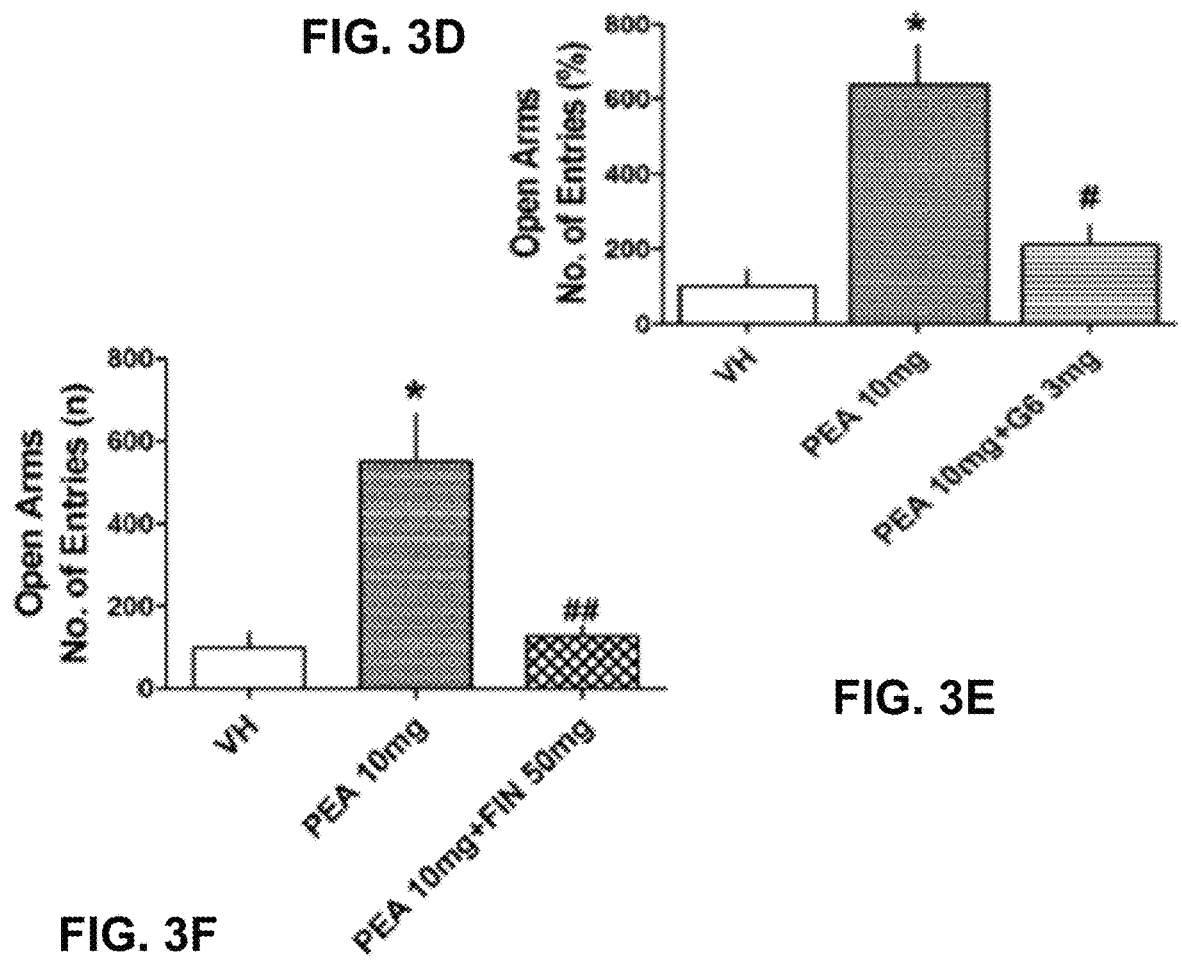
FIG. 3E
FIG. 3F

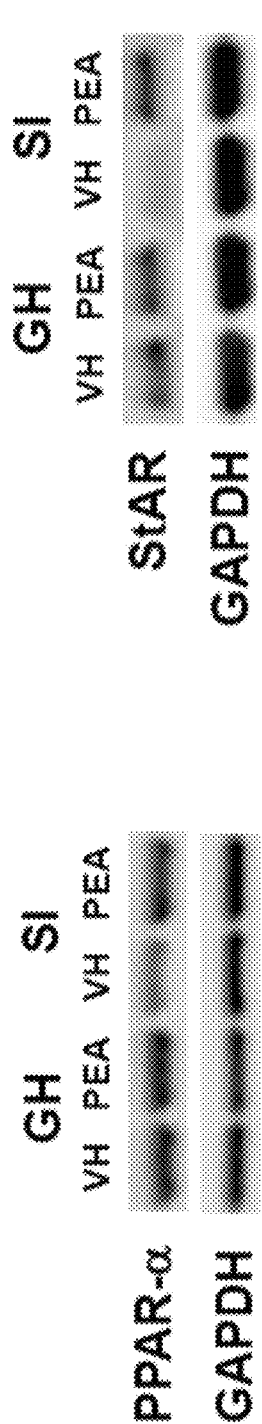
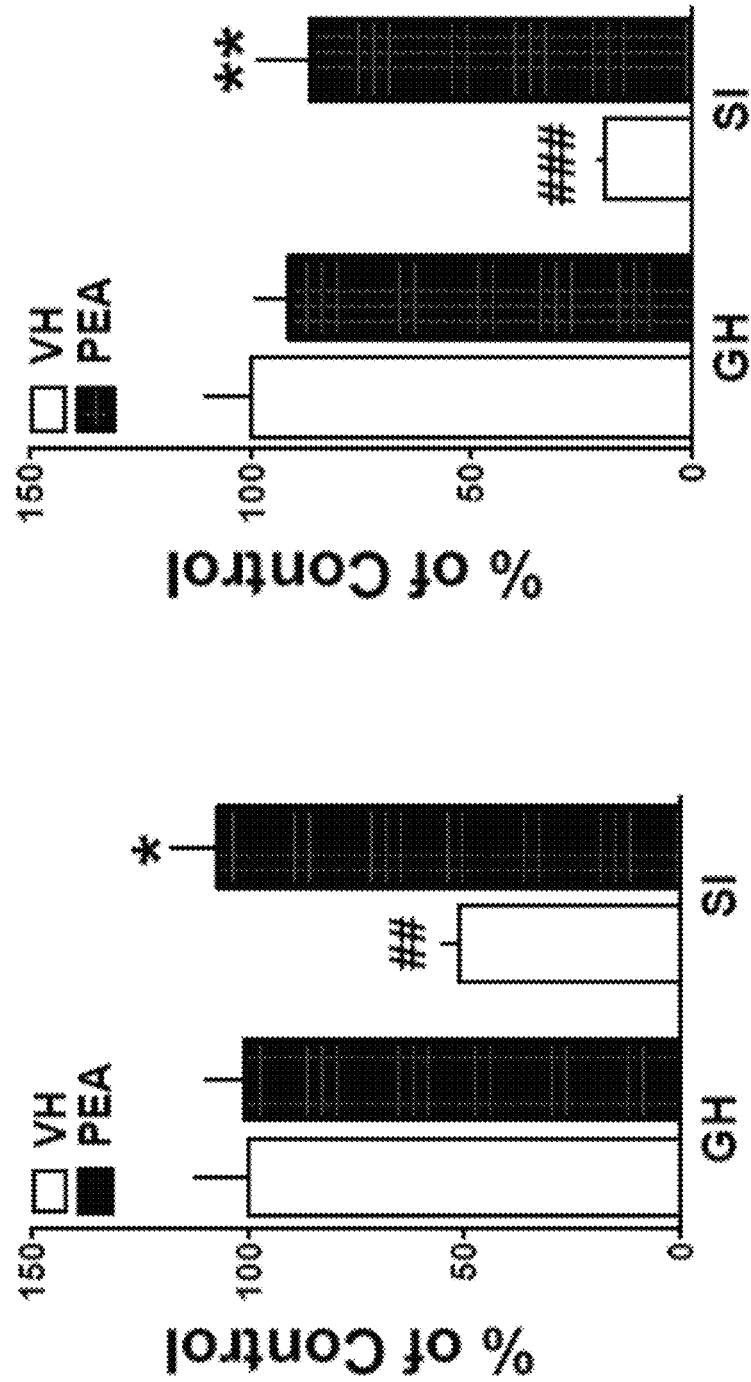
FIG. 4A
FIG. 4B

● GABA
 STEROIDOGENIC ACUTE REGULATORY PROTEIN
● GLUTAMATE
 PEROXISOME PROLIFERATOR-ACTIVATED RECEPTOR
 ALLOPREGNANOLONE
 RETINOID X RECEPTOR
 PREGNANOLONE
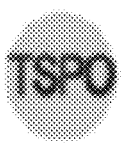 TRANSLOCATOR PROTEIN
 PREGNENOLONE
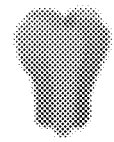 SYNAPTIC GABA RECEPTOR
 ALLOPREGNANOLONE SULFATE
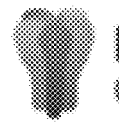 EXTRASYNAPTIC GABA RECEPTOR
 PREGNANOLONE SULFATE
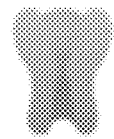 NMDA RECEPTOR
 PALMITOYLETHANOLAMIDE
FIG. 5 (ctnd.)

|  | Pfc | Hip | Amy | Str | OB |
|---|---|---|---|---|---|
| Pregnenolone (pmol/g) | | | | | |
| Vehicle | 7.30 | 2.33 | 6.28 | 2.40 | 26.02 |
| PEA 5 mg | 7.01 | 3.04 | 11.09 | 1.70 | 39.14* |
| PEA 10 mg | 7.06 | 3.82 | 9.87 | 2.13 | 43.96* |
| PEA 20 mg | 5.62 | 2.50 | 11.39 | 2.80 | 15.19 |
| Progesterone (pmol/g) | | | | | |
| Vehicle | 19.99 | 1.16 | 10.23 | 3.52 | 32.45 |
| PEA 5 mg | 20.71 | 5.76 | 13.06 | 5.79 | 34.33 |
| PEA 10 mg | 24.74 | 12.90 | 17.89 | 16.06* | 47.70 |
| PEA 20 mg | 28.80 | **38.13\*\*** | **33.08\*\*** | **24.47\*\*\*** | 48.38 |
| 5α-DHP (pmol/g) | | | | | |
| Vehicle | 40.90 | 22.14 | 59.60 | 41.92 | 93.62 |
| PEA 5 mg | 41.82 | 22.55 | 59.03 | 37.38 | 127.39 |
| PEA 10 mg | 29.96 | 36.20* | 62.23 | 39.51 | 139.15 |
| PEA 20 mg | 45.26 | **41.45\*\*** | 62.38 | 39.36 | 118.42 |

One-Way ANOVA followed by Newman-Keuls post hoc analysis. *p<0.05, p<0.01, and *p<0.001 compared to vehicle-control group.

FIG. 6

PPAR-ALPHA AGONIST TREATMENT OF NEUROPSYCHIATRIC DISORDERS

CROSS-REFERENCE TO RELATED APPLICATIONS

This application claims the benefit of and priority to U.S. Provisional Patent Application No. 62/523,015, filed on Jun. 21, 2017, entitled "Modulating Emotional Behavior with Endocannabinoids," the contents of which is incorporated by reference herein in its entirety.

STATEMENT REGARDING FEDERALLY SPONSORED RESEARCH

This invention was made with government support under grant number W81XWH-15-1-0251 awarded by the United States Department of Defense. The government has certain rights in the invention.

BACKGROUND

Neuropsychiatric disorders are generally diseases, conditions, and disorders of affect, cognition, and/or behavior that can arise from an overt disorder in cerebral function or from indirect effects of extracerebral diseases and disorders. Neuropsychiatric disorders are a significant burden on society and can impair the health of those affected, as well as their ability to learn and work. They also can indirectly burden those not directly afflicted. Indeed, those affected must often rely on caregivers or other forms of assistance due to their inability to fully engage and function in normal work and life activities. As such, there exists a need for the development of improved treatments for neuropsychiatric disorders.

BRIEF DESCRIPTION OF THE DRAWINGS

Further aspects of the present disclosure will be readily appreciated upon review of the detailed description of its various aspects, described below, when taken in conjunction with the accompanying drawings.

FIG. 1A can show results from a single administration of PEA (5 mg/kg, i.p.) (black circles) or vehicle (white circles), given immediately after a contextual fear conditioning reactivation session, facilitates fear extinction (Days 1-3) ("treatment": [$F(3, 24)=10.01$, $p=0.0002$]; "time": [$F(2, 24)=0.5$, $p=0.61$] "interaction": [$F(6, 48)=0.38$, $p=0.89$]), and fear extinction retention on recall (Day 14) in SI mice ("treatment": [$F(1, 27)=9.41$, $p<0.005$]; "isolation": [$F(1,27)=0.611$, $p=0.441$]; "interaction": [$F(1, 27)=12.28$, $p=0.002$]). The same treatment fails to induce effects in GH-control mice (squares). FIG. 1B can show results from administration of a single dose of PEA (5 mg/kg, i.p.) fails to affect fear responses in PPAR-α KO mice. Values are reported in percentage; average of vehicle-treated SI mice is considered as 100%. Data represent the mean±SEM of 9 mice. *$p<0.001$, when compared with PEA-treated SI mice at the same time-point; #$p<0.05$, when compared with vehicle-treated GH mice at the same time-point. Data was analyzed using Two-Way repeated measures ANOVA or Two-Way ANOVA followed by Newman-Keuls post hoc analysis. FIGS. 1C-1D can demonstrate that PEA improves anxiety-like behavior in SI mice. Mice were exposed to an elevated plus maze test for 5 minutes, 1 h after PEA (5 and 10 mg/kg, i.p.). Bar graphs can represent the effect induced by PEA or vehicle treatment on the percentage of total time spent in the open arms (FIG. 1C), and on the number of entries in the open arms (FIG. 1D) of the elevated plus maze both in GH and SI mice. Values are reported in percentage; average of vehicle-treated GH mice is considered as 100%. Data are reported as mean±SEM of 7-9 mice. *$p<0.01$ and **$p<0.001$, when compared with vehicle-treated SI mice; #$p<0.05$ when compared with vehicle-treated GH mice. Data was analyzed using Student's t-test analysis. FIGS. 1E-1F can demonstrate that PEA counteracts the social isolation-induced depressive-like behavior. Mice were exposed to the forced swim test (FST) and were recorded for 4 min, 1 h after PEA (10 mg/kg, i.p.). In FIG. 1E, Bars represent the effect induced by PEA on the time of immobility in SI mice exposed to the FST (["treatment": [$F(1, 27)=2.8$, $p=0.11$]; "isolation": [$F(1,27)=3.3$, $p=0.08$]; "interaction": [$F(1, 27)=4.7$, $p=0.004$]. FIG. 1F can demonstrate that PEA (10 mg/kg, i.p.) fails to induce antidepressant-like effects in SI PPAR-α KO mice. Data are expressed as mean±SEM of 7-9 mice. *$p<0.05$ and **$p<0.01$, when compared with vehicle-treated SI or WT mice; #$p<0.05$, when compared with vehicle-treated GH mice. Data was analyzed using a Two-Way ANOVA followed by Newman-Keuls post hoc analysis.

FIGS. 3A-3L show graphs that can demonstrate the behavioral pharmacology of PPAR-α in SI mice. FIG. 3A can demonstrate an anxiolytic-like effect induced by the PPAR-α agonist, GW 7647 (G7) in SI mice. G7 (10 mg/kg, i.p., given 1 h before an elevated plus maze test) increases the percentage of total time spent in the open arms. FIG. 3B can demonstrate the number of entries in open arms in response to the PPAR-α agonist G7647 (G7) at 10 mg/kg i.p., for 60 minutes before an elevated plus maze test. The average of vehicle-treated SI mice (VH, white bars) is considered as 100%; values of SI mice treated with G7 (grey bars) are reported as percentage compared to VH group. Data represented the mean±SEM of 6 mice. *$p<0.05$ when compared with vehicle-treated SI mice. Data was analyzed using Student's t-test analysis. FIG. 3C can demonstrate that the PPAR-α agonist, fenofibrate (FFB; dose range: 7.5-120 mg/kg, s.c., 1.5 h before test) induces an anxiolytic-like effect in SI mice, as demonstrated by the dose-dependent increase of the time spent in the open arms (7.5 mg/kg: +88%, $p>0.05$; 30 mg/kg: +442%, $p<0.01$; 120 mg/kg: +552%, $p<0.01$). FIG. 3D can demonstrate that the selective PPAR-α antagonist, GW 6471 (G6) or the potent inhibitor of 5α-reductase, finasteride (FIN) can prevent the anxiolytic effect of PEA in SI mice (G6 vs. PEA 10 mg/kg: −78%, $p<0.001$; FIN vs. PEA 10 mg/kg: −68%, $p<0.01$). G6 (3 mg/kg, i.p.), or FIN (50 mg/kg, s.c.), were administered 1.5 h and 2.5 h before the elevated plus maze test, respectively.

PEA (10 mg/kg, i.p.) was injected 1 h before test. FIG. 3E can demonstrate the number of entries into open arms of the elevated plus maze apparatus. The average of vehicle-treated SI mice (VH, white bars) is set as 100%; values of the other experimental group (grey bars) are reported as percentage compared to VH group. Data represented the mean±SEM of 6-7 mice. *$p<0.001$ when compared with vehicle-treated SI mice; #$p<0.01$ and ##$p<0.001$, when compared with PEA at 10 mg. Data was analyzed using a one-way ANOVA followed by Newman-Keuls post hoc analysis. FIG. 3F can demonstrate finasteride (a 5α-reductase inhibitor) can block the anxiolytic effect of PEA on elevated plus maze in SI mice. Representation of the effect induced by the co-administration of finasteride (FIN, 50 mg/kg, s/c/ 150 minutes before the behavioral test) and PEA (10 mg·kg, i.p., 60 min before the behavioral test) on the number of entries in the open arms of the elevated plus maze apparatus. VH represents 100%, and the average of the other experimental groups are reported as percentage as well. Data represent the mean±SEM of 5-7 mice. *$p<0.01$ when compared with vehicle-treated SI mice; #$p<0.01$ and ##$p<0.001$, when compared with PEA at 10 mg. Data was analyzed using a one way ANOVA followed by Newman-Keuls post hoc analysis. FIGS. 3G-3H show graphs that can demonstrate that PEA (10 mg/kg, i.p.) does not induce anxiolytic effects in SI PPAR-α knockout (KO) mice. PEA was injected 60 minutes before an elevated plus maze test was performed. FIGS. 3G-3H can demonstrate PPAR-α deletion resulted in a failure from PEA to increase the percentage of total time (FIG. 3G) and number of entries (FIG. 3H) in the open arms of the elevated plus maze apparatus in SI mice. The average of SI PPAR-α knockout mice treated with vehicle (VH, white bar) was considered as 100%. Data represent the mean±SEM of 5-6 mice. Data was analyzed using Student's t-test. FIG. 3I PEA fails to induce anxiolytic effects in SI PPAR-α KO mice. Data represent the mean±SEM of 7-8 mice. *$p<0.05$, $p<0.01$ and *$p<0.001$, when compared with vehicle-treated SI mice; #$p<0.01$ and ##$p<0.001$, when compared with PEA 10 mg/kg. Data was analyzed using Student's t-test or One-Way ANOVA followed by Newman-Keuls post hoc analysis. FIGS. 3J-3L show graphs that can demonstrate the pharmacology of PPAR-α-induced neurosteroidogenic effects. FIG. 3J shows a graph that can demonstrate that G7 (10 mg/kg, i.p., 1 h before sacrifice) increases Allo levels in the olfactory bulb of SI mice. FIG. 3K can demonstrate that administration of G6 (3 mg/kg, i.p., 1.5 h before sacrifice), or the selective 5α-reductase inhibitor, FIN (50 mg/kg, s.c., 2.5 h before sacrifice), blocked the neurosteroidogenic effect of PEA (10 mg/kg, i.p., 1 h before sacrifice) determined by the Allo content in the olfactory bulb of SI mice (G6 vs. PEA-treated mice: −48%, $p<0.001$; FIN vs. PEA-treated mice −60%, $p<0.001$). FIG. 3L shows a graph can demonstrate that PEA (10 mg/kg, i.p., 1 h before sacrifice) failed to increase Allo levels in the olfactory bulb of SI PPAR-α KO mice. Data represent the mean±SEM of 5-7 mice. *$p<0.01$ and **$p<0.001$, when compared with vehicle-treated SI mice; #$p<0.001$, when compared with PEA 10 mg. Data was analyzed using Student's t-test or One-Way ANOVA followed by Newman-Keuls post hoc analysis.

FIGS. 4A-4D show blot images and corresponding graphs that can demonstrate PEA affects expression of PPAR-α and neurosteroidogenic proteins in the hippocampus of SI mice. A single administration of PEA (10 mg/kg, i.p., 1 h before sacrifice, black bars) reverts the down-regulation of (FIG. 4A) PPAR-α, ["treatment": $F(1, 24)=8.76$, $p=0.007$; "isolation": $F(1,24)=4.94$, $p=0.036$; "interaction": $F(1, 24)=8.38$, $p=0.008$), as well as (FIG. 4B) StAR ["treatment": $F(1,24)=10.39$, $p=0.0036$; "isolation": $F(1, 24)=22.77$, $p<0.0001$; "interaction": $F(1,24)=17.97$, $p=0.0003$), (FIG. 4C) CYP11A1 ["treatment": $F(1, 24)=7.22$, $p=0.013$; "isolation": $F(1, 24)=9.06$, $p=0.006$; "interaction": $F(1,24)=4.34$, $p=0.048$), and (FIG. 4D) 5α-reductase (5α-RI) ["treatment": $F(1, 23)=8.59$, $p=0.008$; "isolation": $F(1, 23)=1.09$, $p=0.31$; "interaction": $F(1,23)=6.74$, $p=0.016$). Values are reported in percentage; average of vehicle-treated GH mice is considered as 100%. Data represent the mean±SEM of 7 mice. *$p<0.01$ and **$p<0.001$, when compared with vehicle-treated SI mice; #$p<0.05$, ##$p<0.01$ and ###$p<0.001$, when compared with vehicle-treated GH mice. Data was analyzing using a Two-Way ANOVA followed by Newman-Keuls post hoc analysis.

FIG. 6 shows a table that can demonstate the effects of PEA on Allo's precursors levels in different coricolimibic regions of SI mice.

Allo and its stereoisomer pregnanolone (PA) are primarily synthesized in glutamatergic neurons and play a central neuromodulatory role in facilitating the action of GABA at $GABA_A$ receptors (a primary target of anxiolytics) and in the fine-tuning of the receptor for agonists and GABA mimetic agents. The finding that Allo facilitates the efficacy of $GABA_A$ receptor allosteric modulators substantiates its endogenous physiological relevance. Neurosteroids can act on $GABA_A$ receptor or on NMDA receptor (sulfated steroids). Allo and PA binding at $GABA_A$ receptors result in behavioral responses, including anti-aggressive, anxiolytic and anti-fear actions; the binding of sulfated Allo and PA inhibit tonic-activated NMDA neurotransmission which result in important repercussions on neuroplasticity, memory formation and learning processes.

The right panel shows the peripheral alterations of eCBs and neurosteroids in patients. It is evident that the modified concentrations of eCBs and neurosteroids present common alterations. The endocannabinoid and neurosteroid system interface, including the action at their receptors (e.g., PPAR-α, CBI and GABAA and NMDA receptors) may provide an important biomarker axis to selectively predict, diagnose, and establish the best individualized treatment selection for MDD and PTSD patients.

Figure 19:
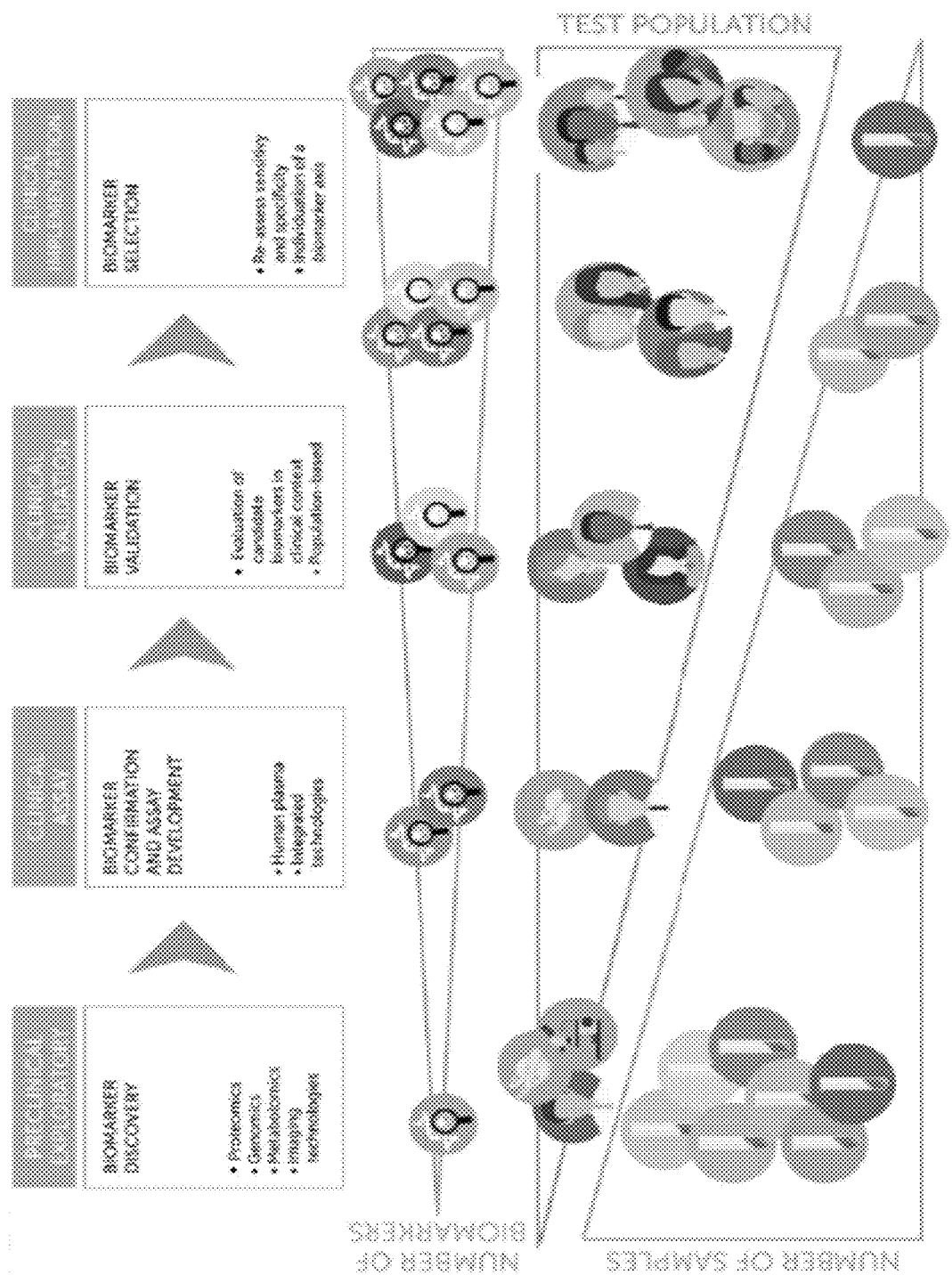

FIG. 19 shows a schematic that can illustrate the process of biomarker-based test assessment. The process that leads to the selection of a biomarker is useful to predict, diagnose and treat psychiatric disorders or test individual susceptibility is articulated in several phases. From the preclinical search to the final selection the number of samples necessary diminishes and assessment of biomarkers becomes available for a large number of individual. Biomarker discovery for potential biomarkers, mainly on animal models, is a long process that requires validation on human samples through different sophisticated technologies, such as gas chromatography-mass spectrometry (GC-MS). Once the biomarker has been established, it has to be validated with a clinical procedure on the population. After this phase, the biomarker selected will go through clinical implementation that improves the specificity and sensitivity of the marker. When more biomarkers are confirmed, it is possible to identify a biomarker axis that allows a precise diagnosis and individualized treatments.

Figure 20:
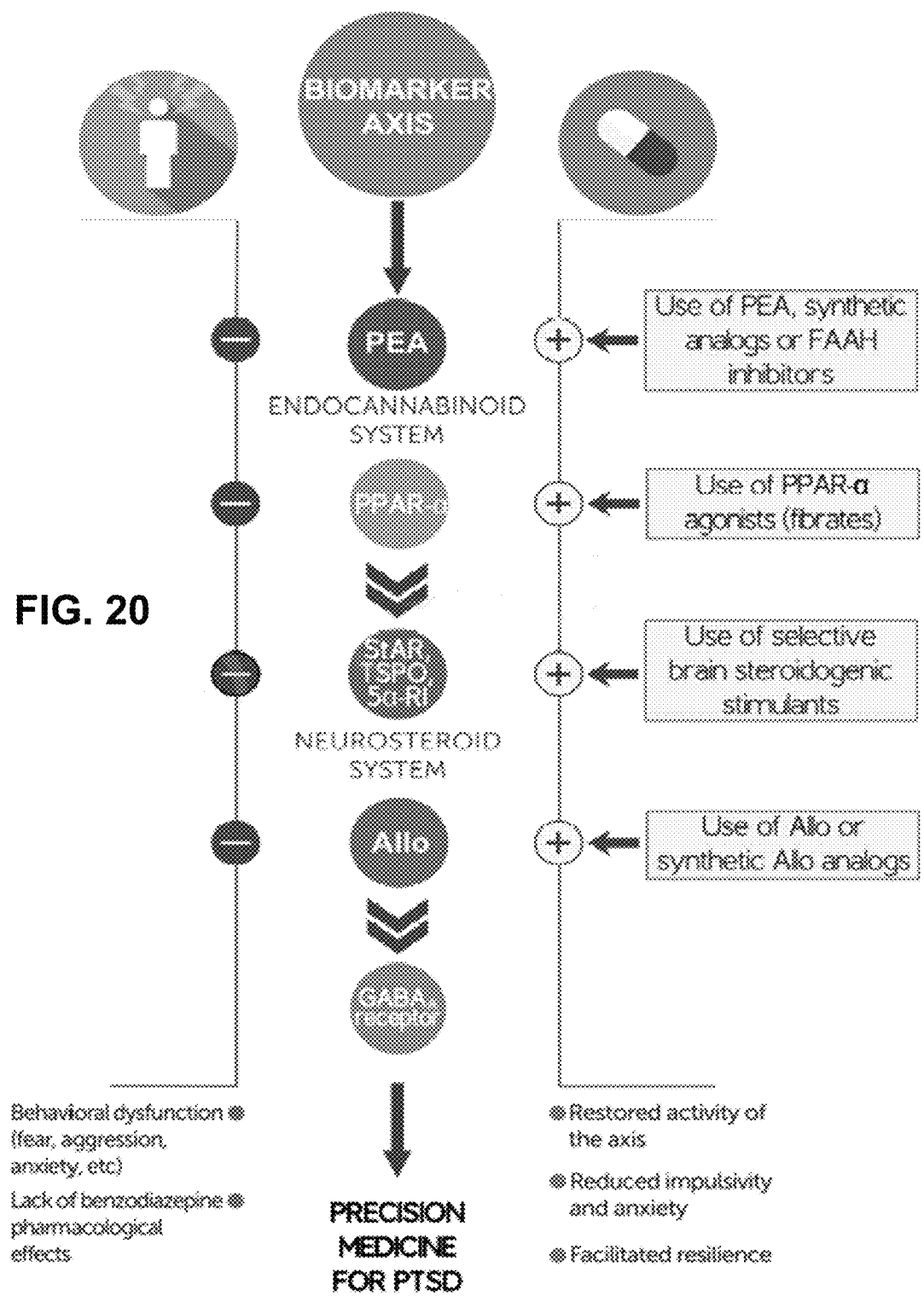

FIG. 20 shows a schematic that can demonstrate the biomarker axis at the interface of the endocannabinoid and neurosteroid systems.

Figure 21:
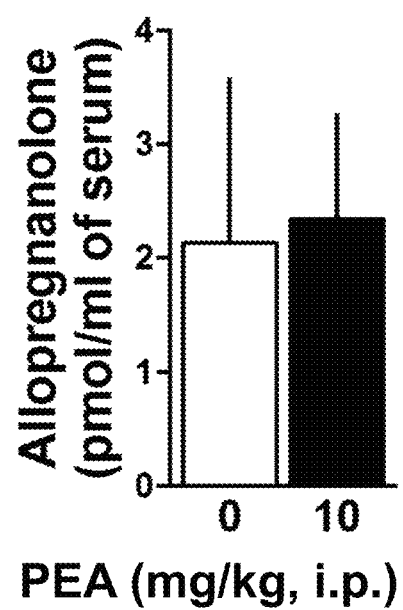

FIG. 21 shows a graph that can demonstrate the effect of PEA on Allo levels determined in the serum of SI mice. A single PEA administration (10 mg/kg, i.p., 1 h before sacrifice) failed to change peripheral levels of Allo. Data are the mean±SEM of 7 mice. Data was analyzed using Student's t-test.

DETAILED DESCRIPTION

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Aspects of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "agent" can refer to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "control" can refer to an alternative subject or sample used in an experiment for comparison purpose and included to minimize or distinguish the effect of variables other than an independent variable.

As used herein, "dose," "unit dose," or "dosage" can refer to physically discrete units suitable for use in a subject, each unit containing a predetermined quantity of the self-assembling cyclopeptide-dye compounds and/or a formulation thereof calculated to produce the desired response or responses in association with its administration.

As used herein, "effective amount" can refer to the amount of a compound provided herein that is sufficient to effect beneficial or desired biological, emotional, medical, or clinical response of a cell, tissue, system, animal, or human. An effective amount can be administered in one or more administrations, applications, or dosages. The term cam also include within its scope amounts effective to enhance or restore to substantially normal physiological function. The "effective amount" can refer to the amount of the PPARα agonist described herein or formulation thereof described herein that can treat and/or prevent a neuropsychiatric disorder or a symptom thereof. In some aspects, the "effective amount" can refer to the amount of the PPARα agonist described herein or formulation thereof described herein that can treat and/or prevent post-traumatic stress disorder or a symptom thereof. In some aspects, the "effective amount" can refer to the amount of the PPARα agonist described herein or formulation thereof described herein that can treat and/or prevent anxiety in a subject.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "organism", "host", "patient", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein "peptide" can refer to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo. Pharmaceutical formulation includes any acceptable pharmaceutically acceptable salts of the active ingredient(s).

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "preventative" and "prevent" can refer to hindering or stopping a disease or condition before it occurs, even if undiagnosed, or while the disease or condition is still in the sub-clinical phase.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a neuropsychiatric disorder (including, but not limited to, PTSD, or a symptom thereof. Others are described elsewhere herein). The effect can be therapeutic in terms of a partial or complete cure of a disease, condition, symptom or adverse effect attributed to the disease, disorder, or condition. The term "treatment" as used herein covers any treatment of a neuropsychiatric disorder (including, but not limited to, PTSD or a symptom thereof), in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic (e.g. preventative) treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

Discussion

Neuropsychiatric disorders are generally diseases, conditions, and disorders of affect, cognition, and/or behavior that can arise from an overt disorder in cerebral function or from indirect effects of extracerebral diseases and disorders. Neuropsychiatric disorders are a significant burden on society and can impair the health of those affected, as well as their ability to learn, work, and/or emotionally cope. They also can burden those not afflicted in that those affected often must rely on caregivers or other forms of assistance due to their inability to fully engage and function in normal work and life activities. Non-limiting examples of neuropsychiatric disorders include addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease), mood/affect disorders (e.g. bipolar disorder, depressions, and mania), neurotic disorders (e.g. obsessive compulsive disorder, trichotillomania, and anxiety disorders (including post-traumatic stress disorder (PTSD)), psychosis (e.g. schizophrenia), and sleep disorders (e.g. sleep apnea, narcolepsy, insomnia, and parasomnia).

Anxiety disorders, including PTSD, affect 8-13% of the population and as much as 25% of soldiers who have spent time in war zones, with an additional 30% have had partial PTSD at some point in their lives. PTSD is marked by clear biological changes as well as psychological symptoms. PTSD is complicated by the fact that people having PTSD often have or develop co-disorders such as depression, substance abuse, problems with memory and cognition, and other problems of physical and mental health. It is reported that up to 80% of Vietnam veterans seeking PTSD treatment abuse alcohol. PTSD is also associated with impairment of the person's ability to function in normal social and/or family live, including occupational instability, marital problems and divorces, family discord, and difficulties parenting.

The benefits and health care costs associated with just veterans affected by PTSD are enormous. The U.S. Congressional Budget Office shows that since Sep. 11, 2001, more than 2.2 million US service members have been deployed to war zones. Among them 1.4 million Afghan and Iraq war veterans are eligible for VA healthcare. About 712,000 patients are treated by the VA and about half of them (about 367,000) are treated for mental healthcare conditions. Patients that have been treated for PTSD account for more than half (about 212,000) of those being treated for mental healthcare conditions. According to the Veteran Health Administration, there are about 10,000 new veteran patients each month.

Benzodiazepines are the most used anxiolytics, but their use is associated with sedation, tolerance, dependence, and severe withdrawal symptoms. Further they are ineffective in those with PTSD. Conventional PTSD treatments include exposure-based therapy (EBT). EBT involves the exposure of the patient to the feared context without any danger, in order to allow the patient to overcome the motivation of their anxiety. This is similar to the procedure used to simulate and study fear responses and fear extinction learning in PTSD mouse models. Generally, psychological therapy has been effective both to treat PTSD and prevent the progression of the event sequelae that leads to the consolidation of fear memories resulting from an acute stress and the development of PTSD.

Despite the reported success of psychological therapy, there are challenges associated with the treatment of PTSD with this modality of treatment. One of the challenges associated with PTSD psychological therapy is the spontaneous recovery of fear that often reemerges a time after conclusion of successful EBT. As such, pharmacological treatment can be advantageous alone or in combination with psychological therapy such as EBT.

Selective serotonin reuptake inhibitors (SSRIs) are the class of drugs that are conventionally used for treating anxiety disorders. SSRIs can be effective in facilitating and restoring the neurobiological changes altered in PTSD patients and are typically devoid of the unwanted side effects that plague the benzodiazepines. SSRIs are can be useful for the treatment of patients with PTSD where benzodiazepines have failed to be beneficial. However, currently available SSRIs are not without their drawbacks. Some SSRIs have significant and intolerable side effects. Further, SSRIs have been reported to have varying benefit and can be ineffective in some patients.

With that said, described herein endocannabinoids or other peroxisome proliferator-activated receptor alpha (PPARα) agonists, such as PEA and AEA that can be administered to a subject in need thereof to treat and/or prevent a neuropsychiatric disorder in the subject. The neuropsychiatric disorder can be an anxiety disorder, including but not limited to, PTSD. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description and be within the scope of the present disclosure.

PPARα Agonists and Pharmaceutical Formulations Thereof

Neurosteroids are steroids that can alter neuronal excitability through non-genomic actions (e.g. action at membrane surface receptors and ligand gated ion channels). Allopregnanolone (abbreviated as "Allo" elsewhere herein) is an example neurosteroid that is endogenously synthesized by post-synaptic neurons from progesterone and can act via retrograde synaptic action at pre-synaptic $GABA_A$ receptors. In the brain, Allo can be synthesized from progesterone by the sequential action of 5alpha-reductase type I (5α-RI), which can reduces progesterone into 5alpha-dihydro-progesterone (5alpha-DHP); 3alpha-hydroxyseroid-dehydrogenase (3alpha-HSD) then converts 5alpha-DHP into Allo via a reduction reaction. 3alpha-HSD can also convert Allo into and 5alpha-DHP via an oxidation reaction. Allo and 5alpha-DHP are unevenly distributed in the mouse brain. Despite the neurotransmitter phenotype (glutamatergic or GABAergic), 5α-RI and 3alpha-HSD are highly expressed in pyramidal, granular cells, reticulo-thalamic medium spiny neurons, and Purkinje neurons and are absent in interneurons and glial cells.

Allo's action is dependent on neuron-type. In glutamatergic neurons, upon secretion, Allo can act in a paracrine fashion at $GABA_A$ receptors located on cell bodies or dendrites of distal pyramidal neurons. Allo can act in an autocrine manner at $GABA_A$ receptors located on glutamatergic neurons dendrites or cell bodies. Allo can access and act at the intracellular sites of $GABA_A$ receptors. Decreased Allo levels and/or reduced Allo biosynthesis can be observed to result in a GABAnergic neurotransmission dysfunction as characterized by a weaker response to the pharmacological action of muscimol, alcohol, pentobarbital, or BDZ, anxiety, and exaggerated contextual fear responses.

Endocannabinoids are lipid-based compounds that can act as neurotransmitters that can bind to cannabinoid receptors and cannabinoid receptor proteins that are expressed throughout the body. Endocannabinoids and cannabinoid receptors can be expressed in the cortex, hippocampus, and BLA. Endocannabinoids such as the fatty acids anadamide (N-arachidonoylethanolamine or AEA) and palmitoylethanolamide (PEA), can act at the peroxisome proliferator-activated receptor alpha (PPARα), which is a member of the nuclear hormone receptor super-family. PPARα can heterodimerize with the retinoid X receptor (RXR) and can bind to consensus binding sites on in the DNA of target genes or their regulatory regions to initiate transcription of the genes. A consensus binding site for the RXR/PPARα heterodimer is present in the gene encoding 5α-RI.

Described herein are PPARα agonists, such as endocannabinoids, and pharmaceutical formulations thereof that can be capable of increasing Allo levels in a subject, including but not limited to various regions in the brain. Those regions can be those that are involved in various neuropsychiatric disorders, including but not limited to anxiety disorders. Without being bound by theory, Allo levels can be increased in a subject in need thereof by exogenous PPARα agonists, including but not limited to AEA and PEA. The increase can be the result of PPARα agonists activating PPARα which can stimulate Allo biosynthesis by increasing gene expression of neurosteroidogenic enzymes and proteins, including 5α-RI, StAR, CYP11A1. PPARα agonists can include, but are not limited to, endocannabinoids (e.g. AEA, PEA, and oleoyldopamine (OEA), stearoylethanolamide (SEA), 2-arachidonoylglycerol (2-AG)), fibrate compounds (e.g. clofibrate, gemfibrozil, ciprofibrate, bezafibrate, and fenofibrate), GW7647, GW6471, dual PPAR agonists (act at PPARα and γ: e.g. aleglitazar, muraglitazar, farglitazar, saroglitazar, chiglitazar and tesaglitazar) (act at PPARα and δ: e.g. GFT505), pan PPAR agonists (e.g. IVA337); phytol, and prinixic acid. In some aspects, the PPARα agonists is a selective PPARα agonist.

The PPARα agonists described herein can be included in a pharmaceutical formulation that, in addition to the compound, can further include a pharmaceutically acceptable carrier. The formulation can be a pharmaceutical formulation. The PPARα agonists and/or formulations thereof described herein can be administered to a subject in need thereof. The subject in need thereof can have, be suspected of having, and/or be at risk for developing a neuropsychiatric disorder. In some aspects, the neuropsychiatric disorder can be an anxiety disorder. In some aspects, the neuropsychiatric disorder can be an anxiety disorder. In some aspects, the neuropsychiatric disorder can be PTSD. The compounds and formulations described herein can be administered by a suitable route, such as but not limited to oral, infusion, epidural, subarachnoid, intracerebroventricular, and intravenous. Other suitable routes are described elsewhere herein.

Parenteral Formulations

The PPARα agonists described herein can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the PPARα agonist(s) described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the self-assembling cyclopeptide-dye compound(s).

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the PPARα agonist(s) in the desired amount in the appropriate solvent or dispersion medium with one or more of the excipients listed above, as required, followed by filtered sterilization. Dispersions can be prepared by incorporating the various sterilized PPARα agonist(s) into a sterile vehicle which contains the basic dispersion medium and the required other ingredients from those listed above. Sterile powders for the preparation of sterile injectable solutions can be prepared by vacuum-drying and freeze-drying techniques, which yields a powder of the PPARα agonist(s) with or without any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of the PPARα agonist(s). Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other aspects, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, including nanoformulations for parenteral administration can also contain one or more excipients, such as dispersing agents, wetting agents, and suspending agents.

Topical Formulations

The PPARα agonist(s) can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some aspects, the PPARα agonist(s) can be administered as a liquid formulation, such as a solution or suspension, a semi-solid formulation, such as a lotion or ointment, or a solid formulation. The PPARα agonist(s) can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some aspects, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some aspects, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some aspects, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. The surfactant can be a non-ionic surfactant. The emulsifying agent is an emulsifying wax. The liquid non-volatile non-aqueous material can be a glycol. The glycol can be propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing the PPARα agonist(s) are also described herein. The lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing the PPARα agonist(s)) are also described herein. The cream can contain emulsifying agents and/or other stabilizing agents. The cream can be in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some aspects of a cream formulation, the water-base percentage can be about 60% to about 75% and the oil-base can be about 20% to about 30% of the total, with the other percentages being the emulsifier agent, preservatives and additives for a total of 100%.

Ointments containing the PPARα agonist(s) and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing the PPARα agonist(s), a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include the PPARα agonist(s). Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. The buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

The formulations can be provided via continuous delivery of one or more formulations to a subject in need thereof. For topical applications, repeated application can be done or a patch can be used to provide continuous administration of the noscapine analogs over an extended period of time.

Enteral Formulations

The PPARα agonist(s) can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing the PPARα agonist(s) can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" can also include all components of the coating composition which can include plasticizers, pigments, colorants, stabilizing agents, and glidants.

Formulations containing the PPARα agonist(s) can be prepared using one or more pharmaceutically acceptable excipients, including diluents, preservatives, binders, lubricants, disintegrators, swelling agents, fillers, stabilizers, and combinations thereof.

Delayed release dosage formulations containing the PPARα agonist(s) can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing the PPARα agonist(s) can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Kits Containing a PPARα Agonist or Pharmaceutical Formulation Thereof

The PPARα agonist(s) and pharmaceutical formulations thereof described herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include, but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations. When one or more of the active agents are not administered simultaneously, the combination kit can contain each active agent in separate pharmaceutical formulations. The separate pharmaceutical formulations can be contained in a single package or in separate packages within the kit.

The kit can also include instructions printed on or otherwise contained in a tangible medium of expression. Instructions can be incorporated in labels, boxes, containers, syringes, delivery devices, insert sheets of paper, flash drives, CD-ROM, an internet website and the like. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some aspects, the instructions provide directions for administering the compounds, compositions, pharmaceutical formulations, or salts thereof to a subject having, suspected of having, or predisposed to or at risk of developing a neuropsychiatric disorder including, but not limited to addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease; amyotrophic lateral sclerosis (ALS), multiple sclerosis), mood/affect disorders (e.g. bipolar disorder, depressions, premenstrual syndrome, impulsivity, aggressiveness, and mania, anxiety spectrum disorders), neurotic disorders (e.g. obsessive compulsive disorder, trichotillomania, and anxiety disorders)), post-traumatic stress disorder (PTSD), psychosis (e.g. schizophrenia), and sleep disorders (e.g. sleep apnea, narcolepsy, insomnia, and parasomnia), epilepsy, suicide, traumatic brain injury (TBI), chronic pain, alcohol and other substance addiction.

The instructions can provide directions for administering the PPARα agonist(s) and/or pharmaceutical formulations thereof to a subject having, suspected of having, or predisposed to developing PTSD. The instructions can provide directions administering the PPARα agonist(s) and/or pharmaceutical formulations thereof to a subject in need thereof that is a non-responder to conventional neuropsychiatric therapies, including conventional pharmacological intervention including but not limited to benzodiazepines and/or SSRI's. The instructions can provide directions for administering compounds, compositions, pharmaceutical formulations, or salts thereof to a subject having lower Allo levels in the brain, saliva, and/or CSF, as compared to a normal control and/or healthy subject. The instructions can provide directions for administering the PPARα agonist(s) and/or pharmaceutical formulations thereof to a subject in need thereof when the subject in need thereof expresses a biomarker for a neuropsychiatric disorder (see e.g. Table 1). The instructions can provide directions for administering the PPARα agonist(s) and/or pharmaceutical formulations thereof to a subject in need thereof when the subject in need thereof expresses a biomarker for PTSD (see e.g. Table 1).

Methods of Treating Neuropsychiatric Disorders Using a PPARα Agonist or Pharmaceutical Formulation Thereof Also described herein are methods of treating a neuropsychiatric disorder in a subject in need thereof. The PPARα agonist(s) and/or pharmaceutical formulation(s) thereof can be administered to a subject in need thereof. In some aspects the subject in need thereof can have, be suspected of having, and/or be predisposed to and/or at risk of developing a neuropsychiatric disorder. Neuropsychiatric disorder can include addiction, developmental conditions (e.g. attention deficit hyperactivity disorder (ADHD), autism, fetal alcohol syndrome, and tic disorders), eating disorders, degenerative disease (e.g. dementia, Parkinson's disease, and Alzheimer's disease; amyotrophic lateral sclerosis (ALS), multiple sclerosis), mood/affect disorders (e.g. bipolar disorder, depressions, premenstrual syndrome, impulsivity, aggressiveness, and mania, anxiety spectrum disorders), neurotic disorders (e.g. obsessive compulsive disorder, trichotillomania, and anxiety disorders)), post-traumatic stress disorder (PTSD), psychosis (e.g. schizophrenia), and sleep disorders (e.g. sleep apnea, narcolepsy, insomnia, and parasomnia), epilepsy, suicide, traumatic brain injury (TBI), chronic pain, alcohol and other substance addiction. In some aspects, the neuropsychiatric disorder is characterized by low Allo levels, such as in the brain, CSF, blood, or other tissue or fluid sample. In some aspects the subject in need thereof is a non-responder to conventional therapies, including conventional pharmacological intervention including but not limited to benzodiazepines and/or SSRI's. In some aspects, the neuropsychiatric disorder can be PTSD.

In some aspects, one or more of the biomarkers shown in Table 1 can be measured and detected in the subject in need thereof. Suitable methods for measuring or detecting a biomarker for a neuropsychiatric disorder can be PCR techniques, immunodetection techniques (e.g. ELISA, western blotting, ChiP, and immunohistochemistry), mass spectrometry, gas chromatography and other chromatography techniques (e.g. high performance liquid chromatography, other size exclusion chromatography techniques, other ion exchange chromatography techniques, affinity chromatography techniques, and other gel filtration chromatography techniques).

TABLE 1

Biomarkers for Neuropsychiatric Disorders

| Biomarker | Example Neuropsychiatric Disorders or symptom thereof | Reference |
|---|---|---|
| polymorphisms in the dopamine D2 receptor gene (DRD2 gene) 957C > T | PTSD | Example 3, Voisey et al. *Depress Anxiety*. 2009; 26(1): 28-33 |
| polymorphism in the 5α-reductase type 2 | PTSD, depression | Example 3, Hellgren et al. *Hormones and Behavior*. 2017; 94: 106-113 |
| decreased expression of the FKB5 gene | PTSD, depression | Example 3, Menke et al. *Neuropsychopharmacology*. 2012. 37(6): 1455-64 |
| methylation status of the FKB5 gene | PTSD | See e.g. Example 3 herein |
| increased cortisol | PTSD | See Example 3 |
| increased methylation of exon 1 of the glucocorticoid receptor gene (leukocytes and hippocampus | PTSD | See Example 3 |
| methylation status of NPY | PTSD | See Example 3 |
| methylation status of brain-derived neurotropic factor (BDNF) | PTSD | See Example 3 |
| methylation status of α-MSH | PTSD | See Example 3 |
| methylation status of enzymes involved in biosynthesis of neurohormones (e.g. GABAergic steroids) | PTSD | See Example 3 |
| increased C-reactive protein | PTSD, depression | See Example 3 |
| increased IL-6 (serum) | PTSD, a treatment (e.g. SSRI) non-responder | See Example 3 |
| decreased BNDF expression serum and brain (e.g. hippocampus) | PTSD, depression, can be indicative of effective response to treatment of SSRI | See Example 3 |
| decreased TrkB (BDNF receptor) | PTSD, depression | See Example 3 |
| polymorphisms in BDNF gene (rs6265 Val66Met substitution and others) | PTSD, affect disorders, depression | See Example 3 |
| decreased NPY (CSF and plasma) | PTSD | See Example 3 |
| SNP in NPY gene (rs16147) | PTSD, depression | See Example 3 |
| Decreased neurosteroids Allo and pregnanolone) (serum, plasma, CSF, brain) | PTSD, depression | See Example 3 |
| decreased 5α-reductase type 1 | PTSD, depression | Example 3 |
| SNP in 5α-reductase type 1 gene | PTSD, depression | Example 3 |
| level of dehydroepiandrosterone (DHEA) and sulfate derivatives (levels are increased) | PTSD | Example 3 |
| ratio of DHEA to Allo | PTSD | Example 3 |
| increased $GABA_A$ receptor subunits α4, α5, and δ | PTSD | See Examples 3 and 4 |
| reduced $GABA_A$ receptor subunits α1, α2, and γ2 | PTSD | See Example 4 |
| increased sensitivity for neurosteroids | PTSD | See Example 4 |
| failure to bind benzodiazepines and no clinical response to benzodiazepines | PTSD | See Examples 3 and 4 |
| increased cannabinoid receptor 1 ($CB_1$) | PTSD | See Example 3 |
| decreased serum AEA and 2-arachidonoylglycerol (2-AG) | PTSD, depression | See Example 3 |
| decreased PEA and OEA | PTSD, depression | See Example 3 |
| polymorphism in 5-HTT gene | depression | See Example 3, Caspi et al., *Science*. 2003 |

TABLE 1-continued

Biomarkers for Neuropsychiatric Disorders

| Biomarker | Example Neuropsychiatric Disorders or symptom thereof | Reference |
| --- | --- | --- |
| | | 18; 301(5631): 386-389 |
| SNP in the CRHR1 gene: 110402, patients homozygous for the TT allele | Major depressive disorder (MDD) | See Example 3 |
| increased corticotrophin releasing hormone in CSF | depression | See Example 3 |
| increased adrenocorticotrophic hormone | depression | See Example 3 |
| increased glucocorticoid synthesis | depression | See Example 3 |
| increased cortisol (saliva, urine, plasma) | PTSD, depression | See Example 3 |
| decreased sensitivity as determined by response to dexamethasone by the glucocorticoid receptor | depression | See Example 3 |
| polymorphisms in the FKB5 genes rs1360780 | depression | See Example 3 |
| increased tumor necrosis factor alpha (TNF-α) | Depression, PTSD, also can indicate an SSRI non-responder | See Example 3 |
| increased IL-1 | depression | See Example 3 |
| increased IL-6 | Depression, can also indicate an SSRI non-responder | See Example 3 |
| Increased IL-1β | depression | See Example 3 |
| SNPs in IL-1β gene: rs16944, rs1143643 | Depression, also can be indicative of subjects non-responsive to anti-depressants | See Example 3 |
| IL-6 SNP rs1800795 | depression | See Example 3 |
| decreased 3α-hydroxisteroid dehydrogenesis | Depression, PTSD | See Example 3 |
| SNPs cannabinoid receptor 1 (CB$_1$) | Depression | See Example 3 |

The method can include administering an amount of the PPARα agonist(s) and/or pharmaceutical formulation(s) the subject in need thereof. The amount can be an effective amount. As described above, the subject in need thereof can have, be suspected of having, be predisposed to, and/or at risk for developing a neuropsychiatric disorder. The effective amount can reduce or eliminate a symptom of a neuropsychiatric disorder. The effective amount can increase Allo biosynthesis in the central nervous system of the subject. The effective amount can increase Allow levels in the central nervous system of the subject.

The PPARα agonist(s) and/or pharmaceutical formulation(s) can be co-administered or be a co-therapy as part of a treatment regimen with another active agent or ingredient that can be included in the formulation or provided in a dosage form separate from the PPARα agonist(s) and/or pharmaceutical formulation(s). Other active agents or ingredients can include SSRI's (e.g. citalopram, escitalopram, fluoxetine, paroxetine, sertraline, and vilazodone). In some aspects, the SSRI's can be administered at low non-serotonergic doses and thus can act as selective brain steroidogenic stimulants. Other active agents or ingredients can include Allo, ganaxolone, BR351, and/or BR297. The PPARα agonist(s) and/or pharmaceutical formulation(s) can be included in a treatment regimen that includes psychotherapy.

The amount of the PPARα agonist(s) and/or pharmaceutical formulation(s) administered can range from about 0.1 μg/kg to up to about 1000 mg/kg or more, depending on the factors mentioned elsewhere herein. The amount can range from 0.1 μg/kg up to about 500 mg/kg, or 1 μg/kg up to about 500 mg/kg, 5 μg/kg up to about 500 mg/kg, 0.1 μg/kg up to about 100 mg/kg, or 1 μg/kg up to about 100 mg/kg, 5 μg/kg up to about 100 mg/kg. In some aspects, the amount can range from about 5 mg/kg to about 20 mg/kg. In some aspects, the amount can be 5 mg/kg, 10 mg/kg, 15 mg/kg, or 20 mg/kg. In some aspects, the effective amount can range from about 5 mg/kg to about 20 mg/kg. In some aspects the effective amount can be about 5 mg/kg, 10 mg/kg, 15 mg/kg, or 20 mg/kg. In some aspects the PPARα agonist can be PEA and can be administered at about 5 mg/kg to about 20 mg/kg.

Administration of the PPARα agonist(s) and/or pharmaceutical formulation(s) can be systemic or localized. The PPARα agonist(s) and/or pharmaceutical formulation(s) thereof can be administered to the subject in need thereof one or more times per hour or day. The PPARα agonist(s) and/or pharmaceutical formulation(s) thereof can be administered once daily. The PPARα agonist(s) and/or pharmaceutical formulation(s) thereof can be administered can be administered 2, 3, 4, 5, 6, 7, 8, 9, 10, 11, 12, or more times daily. When administered, an effective amount of the PPARα agonist(s) and/or pharmaceutical formulation(s) thereof can be administered to the subject in need thereof. The PPARα agonist(s) and/or pharmaceutical formulation(s) thereof can be administered one or more times per week. The PPARα agonist(s) and/or pharmaceutical formulation(s) thereof can be administered 1, 2, 3, 4, 5, 6 or 7 days per week. The PPARα agonist(s) and/or pharmaceutical formulation(s) thereof can be administered 1, 2, 3, 4, 5, 6, 7, 8, 9, 10, 11, 12, or more times per month. The PPARα agonist(s) and/or pharmaceutical formulation(s) thereof can be administered 1, 2, 3, 4, 5, 6, 7, 8, 9, 10, 11, 12, 13, 14, 15, 16, 17, 18, or more time per year.

The PPARα agonist(s) and/or pharmaceutical formulation(s) thereof can be administered in a dosage form. The amount or effective amount of the PPARα agonist(s) and/or pharmaceutical formulation(s) thereof can be divided into multiple dosage forms. For example, the amount or effective amount can be split into two dosage forms and the one dosage forms can be administered, for example, in the morning, and the second dosage form can be administered in the evening. Although the amount can be given over two or more doses, in one day, the subject can receives the desired amount or effective amount when the total amount administered across all the doses is considered. The dosages can range from about 0.1 μg/kg to up to about 1000 mg/kg or more, depending on the factors mentioned above. In certain aspects, the dosage can range from 0.1 μg/kg up to about 500 mg/kg, or 1 μg/kg up to about 500 mg/kg, 5 μg/kg up to about 500 mg/kg, 0.1 μg/kg up to about 100 mg/kg, or 1 μg/kg up to about 100 mg/kg, 5 μg/kg up to about 100 mg/kg. In some aspects, the dosage can range from about 5 mg/kg to about 20 mg/kg. In some aspects, the dosage can be 5 mg/kg, 10 mg/kg, 15 mg/kg, or 20 mg/kg.

In some aspects, the method can also include the step of measuring one or more biomarkers for a neuropsychiatric disorder. In some aspects the biomarker can be a biomarker shown in Table 1.

EXAMPLES

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of aspects of the present disclosure.

Example 1

Introduction.

N-Palmitoylethanolamine (PEA) is an endocannabinoid (eCB), which is synthesized from the phospholipid, N-palmitoyl-phosphatidyl-ethanolamines (NAPE), by N-acyl phosphatidylethanolamine phospholipase D (NAPE-PLD), and is metabolized by the fatty acid amide hydrolase (FAAH) and, more selectively, by N-acylethanolamine acid amide hydrolase (NAAA) (1). PEA and synthetic ligands (e.g., thiazolidinediones, fibrates), directly stimulate the ligand-activated nuclear receptor, peroxisome proliferator-activated receptor (PPAR)-α that, after heterodimerizing with the retinoid X-receptor-α, binds promoter regions of target genes (2). These include genes for lipid metabolism, synthesis of cholesterol, and catabolism of amino acids (2).

Like PEA, PPAR-α is widely expressed in the brain, where plays a role in the down-regulation of neuroinflammation and oxidative stress (3). In support, targeting PPAR-α with selective agonists alleviates neurodegenerative disorders. In fact, PEA is currently used clinically for neuroprotection, analgesia and as anti-inflammatory agent (4).

The eCB system has been implicated in the neuropathophysiology of stress-related neuropsychiatric disorders, such as PTSD and depression (5, 6). Despite PEA is detectable in the brain at physiologically relevant concentrations, and its levels are altered in neurodegenerative diseases (7), its role on psychiatric disorders is poorly understood. Reduced levels of anandamide (AEA), a well-known eCB that mainly activates cannabinoid receptor type 1 (CB1) have been established in depression and PTSD (8, 9). While studies point to CB1 as the mechanism for AEA effects, intriguingly, AEA binds also at PPAR-α (10). However, a single study shows that PTSD symptoms are inversely correlated with reduced PEA levels (11). Interestingly, PEA levels were increased in rat corticolimbic regions by antidepressant treatment (12).

A cross-interaction between PPAR-α and the neurosteroid system has been recently suggested (13, 14). Studies in astrocytes and spinal cord showed PEA's binding at PPAR-α stimulates the biosynthesis of the neurosteroid, allopregnanolone (Allo), and potentiates pentobarbital-evoked hypnosis (13, 14). Allo is a potent positive allosteric modulator of GABA's action at $GABA_A$ receptors, which regulates the receptor fine-tuning and induces anticonvulsant, anxiolytic, antidepressant, sedative and analgesic effects (15). Importantly, Allo can be produced de novo in glutamatergic neurons of the cortex, hippocampus and basolateral amygdala from its precursor progesterone by the dual action of 5α-reductase type I and 3α-hydroxysteroid dehydrogenase enzymes (16, 17). Given that PPAR-α is widely distributed in glutamatergic corticolimbic neurons (3), it is conceivable; PPAR-α activation by PEA or other PPAR-α agonists may induce Allo biosynthesis in corticolimbic neurons tightly involved in regulation of emotions. Compelling evidence indicates endogenous Allo in the brain is altered rodent stress models and in mood disorders (18, 19). Impaired Allo levels have been shown in the serum, cerebrospinal fluid (CSF), and brain of depression and PTSD patients (18, 20, 21, 22, 23). Prior studies showed that brain Allo levels are also reduced in rodents following protracted social isolation, which results in a PTSD-like phenotype, including increased aggression, anxiety-like behavior, and exaggerated contextual fear responses (24, 25). Furthermore, selective serotonin reuptake inhibitors (SSRIs), at low non-serotonergic doses, act as selective brain steroidogenic stimulants (SBSSs), upregulate brain Allo levels and improve behavior in Allo-deficient rodents (24, 25, 26). Likewise, clinical studies have demonstrated SSRIs improve depression by normalizing plasma and CSF Allo levels (20, 21, 27).

Currently, treatment for depression and PTSD fails to improve symptoms in half of treatment seeking patients, highlighting the need to develop new therapies specifically designed for treatment non-responders. The current study shows a previously unknown function of PPAR-α in regulating corticolimbic neurosteroid biosynthesis and emotional behavior. Our results suggest novel translational biomarker candidates and agents suitable for a long-needed precision medicine to counteract PTSD and depression.

Materials and Methods.

Animals. Male Swiss-Webster mice (Harlan Breeders, Indianapolis, Ind.), or PPAR-α KO mice (Pparatm1Gonz/J, The Jackson Laboratory, Bar Harbor, Me.) (21-23 days at arrival) were maintained under a 12-h dark/light cycle with food and water ad libitum. Mice were housed individually (socially isolated, SI) in a cage (24×17×12 cm) for 5 weeks, while group-housed (GH) mice were housed in groups of 5. The vivarium temperature was 24° C. and the humidity 65%.

Drug treatments. N-palmitoylethanolamide (PEA; Epitech Group; 5-20 mg/kg, i.p., 5% tween-80 in saline), GW7647 (G7; Tocris; 5% tween-80 in saline), dose 10 mg/kg, i.p., were given 1 h before tests. Fenofibrate (FFB; Sigma; 7.5-120 mg/kg, s.c., canola oil), was given 1.5 h before tests. GW6471 (G6; Tocris; 3 mg/kg, i.p., 5% tween- 80 in saline), was injected 1.5 h before tests. Finasteride (FIN; Tocris; 50 mg/kg, s.c., canola oil) was given 2.5 h before tests.

Contextual fear conditioning. Contextual fear conditioning was performed as previously (25). Briefly, the conditioning and extinction chamber (25×18×21 cm), surrounded by 16 infrared photo beams, had a stainless steel rods floor connected to an electric shock generator (San Diego Instrument, Inc., San Diego, Calif.).

Conditioning trial. Mice were placed in the chamber and exposed for 8 min to a conditioned stimulus and an electric foot-shock (unconditioned stimulus).

Reactivation. 24 h after conditioning, mice were re-exposed for 5 min to the context for retrieval/reactivation and treated immediately after reactivation.

Extinction and extinction retention. 24 h after reactivation, mice were re-introduced for 5 min in the chamber once daily for 5 days and freezing time was an index of contextual fear responses. After an interval of 8 days, mice were re-exposed to the chamber to determine extinction retention (25).

Elevated plus maze. Elevated plus maze tests were performed as previously (28). Mice chose between entering open or closed arms that extend from a central platform. An arm entry was scored when four legs were within the arm. Behavior was recorded for 5 min. The time spent and the number of open arm entries were used as index of anxiety-like behavior.

Locomotor activity. A computerized AccuScan 12 Animal Activity Monitoring System (Columbus Instruments, Columbus, Ohio) assisted by VERSAMAX software (AccuScan Instruments, Columbus, Ohio) was used to evaluate locomotor activity (29). Horizontal sensors beam interruptions measured horizontal activity for a total of 10 min.

Forced swim test and tail suspension test. The forced swim test (FST) or a tail suspension test (TST) was performed as previously (30, 31). FST sessions were video-recorded for 6 min and the last 4 min were analyzed (30). TST duration was 6 min. Immobility time was an index of depressive-like behavior.

Brain neurosteroid measurements. Extraction, derivatization and quantification of unconjugated neurosteroids was described previously (32). Steroids were extracted and then purified and separated by high-performance liquid chromatography (HPLC) after addition of deuterium-labeled internal standards (25). The aqueous phase (2 ml) containing sulfated neurosteroids underwent a solvolysis. After derivatization, gas chromatography-mass spectrometry analysis in the standard electron impact mode as previously reported (24, 25).

Western blot. The abundance of PPAR-α, StAR, CYP11A1 and 5α-reductase type I was determined in lysates of hippocampus as previously (33). Equal amounts of protein were subjected gel electrophoresis (200 volts for 75 minutes) on 4-12% gel (NuPAGE Novex, Thermo Fisher Scientific, Waltham, Mass., USA). Immunoblot with primary antibodies against PPAR-α, CYP11A1, and 5α-reductase type I (1:500, Proteintech, Rosemont, Ill., USA), and StAR (1:500, Abcam, Cambridge, Mass., USA), were also incubated with glyceraldehyde-3-phosphate dehydrogenase (GAPDH) primary antibody (1:50,000, Millipore Sigma, Billerica, Mass., USA) for normalization. HRP-conjugated secondary anti mouse and anti-rabbit antibodies were used. Membranes were developed and densitometric analysis was conducted with Image Studio™ (LI-COR Bioscience, Lincoln, Nebr.).

Statistical analyses. Results are presented as means±SEMs unless otherwise indicated. Student's t-test, One-way ANOVA, Two-Way ANOVA, or Two-Way repeated measures ANOVA followed by Newman-Keuls post hoc tests were performed to analyze experimental data; significance was set at $p<0.05$.

Results.

Figure 1A:
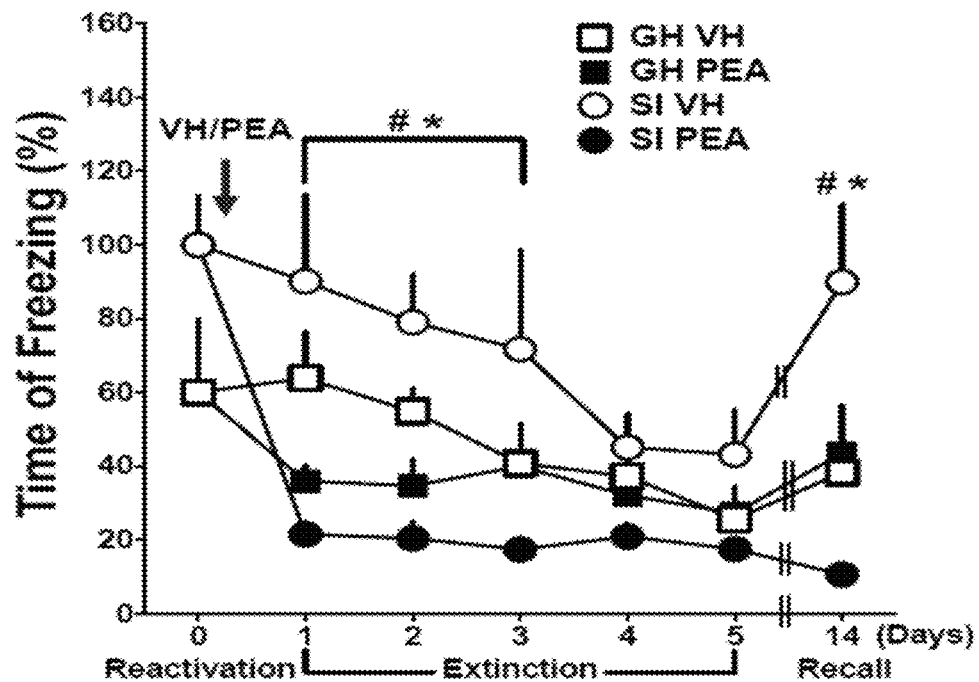
FIGS. 1A-1F show graphs that can demonstrate PEA facilitates extinction of contextual fear memory and prevents spontaneous fear reinstatement in SI mice.
Figure 1B:
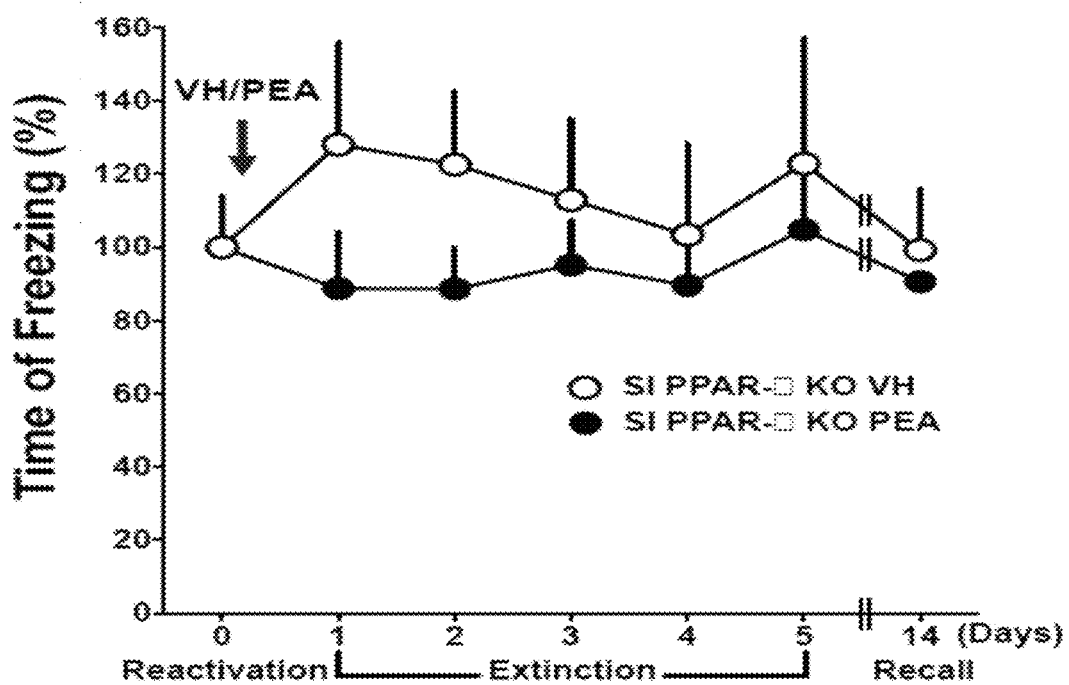

PEA can improve contextual fear responses and facilitates fear extinction in SI mice. SI mice exhibited enhanced contextual fear conditioning responses compared to GH control mice (first three days of extinction trials: +51%, $p<0.05$; recall day: +135%, $p<0.05$) (FIG. 1A). A single administration of PEA (5 mg/kg, i.p.), given immediately after a reactivation session, by blocking the fear memory reconsolidation, facilitated fear extinction during the first three days of extinction trials (−75%; $p<0.001$), and, most importantly, prevented the spontaneous recovery of contextual fear memory after passage of time, during recall (Day 14), i.e., facilitated fear extinction retention (−88%, $p<0.001$) (FIG. 1A). Of note, PEA failed to affect contextual fear responses both in GH and PPAR-α KO mice (FIGS. 1A-B).

Figure 1C:
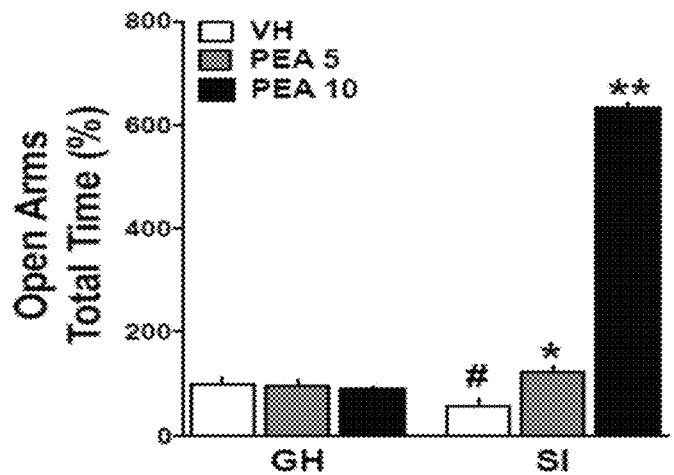
Figure 1D:
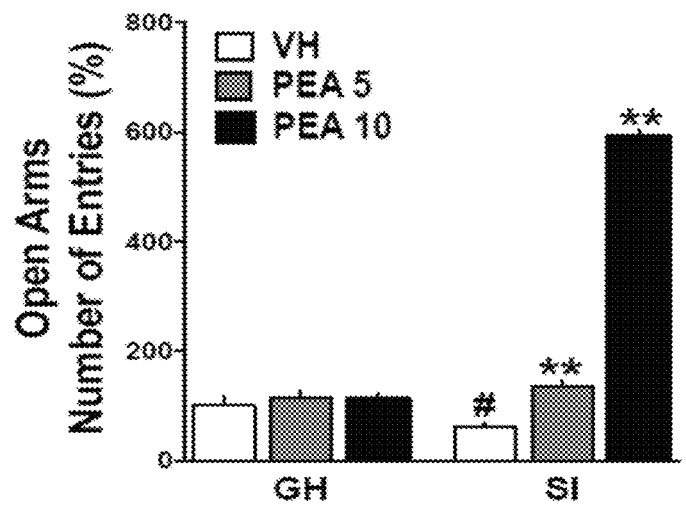

PEA induces a strong anxiolytic effect in SI mice. SI mice showed an enhanced anxiety-like behavior consisting in less time spent (−42%, $t(14)=2.193$, $p<0.05$), (FIG. 1C) and lower number of entries in the open arms (−42%, $t(12)=2.488$, $p<0.05$), (FIG. 1D) compared to GH mice. PEA (5-10 mg/kg, i.p.) induced a dose-dependent anxiolytic effect (5 mg/kg: +113%, $t(15)=3.615$, $p<0.01$, and +116%, $t(10)=p<0.001$; 10 mg/kg: +533%, $t(18)=4.53$, $p=0.0003$, and +492%, $t(22)=5.598$, $p<0.0001$, time spent and number of entries, respectively) (FIGS. 1C-1D). However, PEA treatment had no effect in GH mice (FIGS. 1C-1D).

Figure 1E:
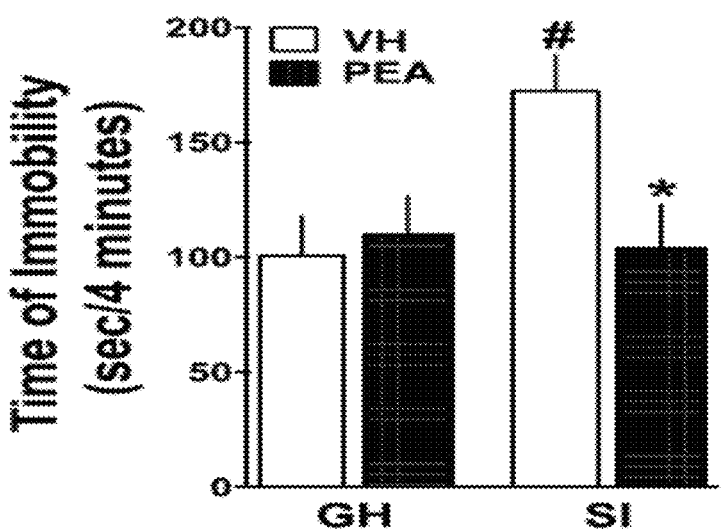
Figure 1F:
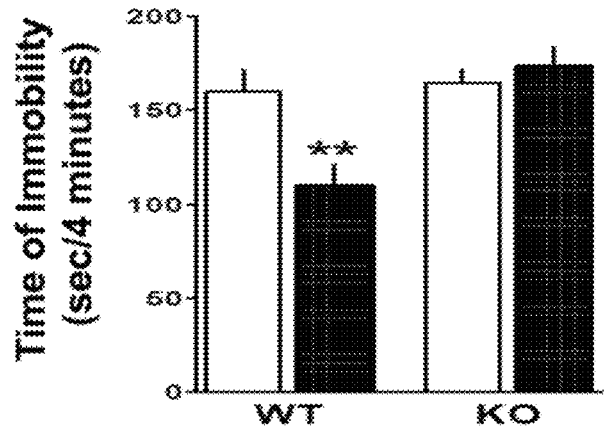
Figure 2A:
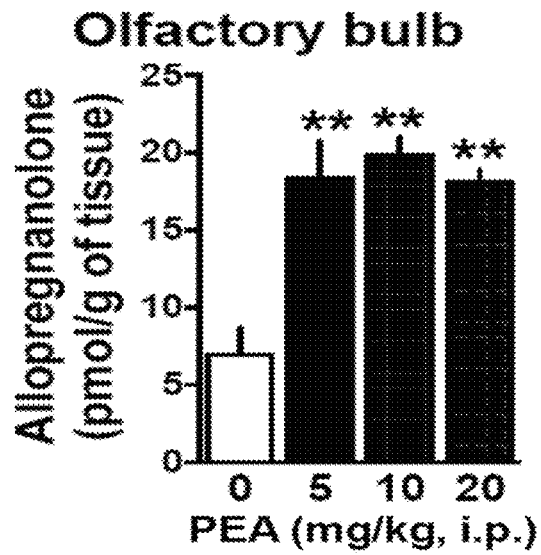
FIGS. 2A-2E show graphs that can demonstrate a neurosteroidogenic effect induced by PEA in corticolimbic areas of SI mice. PEA (5, 10 and 20 mg/kg, i.p.) was observed to increase Allo levels in the olfactory bulb (5 mg/kg: +164%, $p<0.001$; 10 mg/kg: +185%, $p<0.001$; 20 mg/kg: +160%, $p<0.001$), hippocampus (5 mg/kg: +38%, $p<0.05$; 10 mg/kg: +78%, $p<0.001$; 20 mg/kg: +78%, $p<0.001$), and amygdala (5 mg/kg: +34%, $p<0.05$; 10 mg/kg: +42%, $p<0.05$; 20 mg/kg: +120%, $p<0.001$), and at the high 20 mg/kg dose in the frontal cortex (+41%, $p<0.05$). However, PEA failed to change Allo levels in the striatum of SI mice. Mice were sacrificed 1 h after PEA treatment. Data represent the mean±SEM of 6-7 mice. *$p<0.05$ an **$p<0.001$, when compared with vehicle-treated SI mice. Data was analyzed by One-Way ANOVA followed by Newman-Keuls post hoc analysis.
Figure 2B:
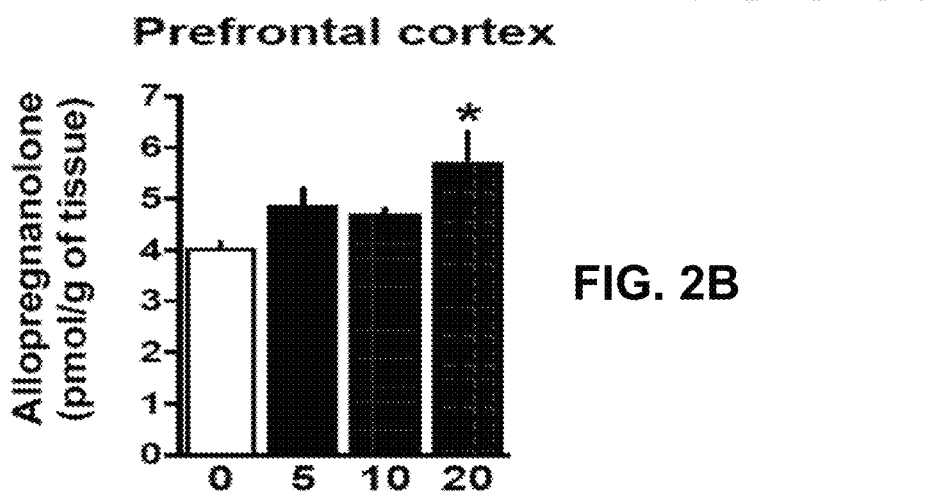
Figure 2C:
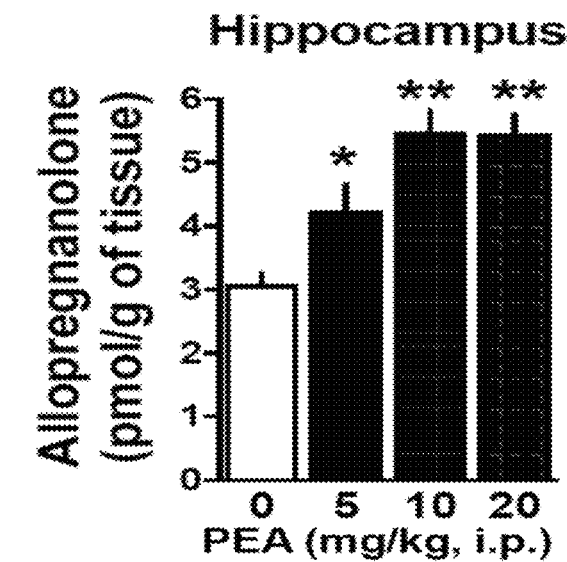
Figure 2D:
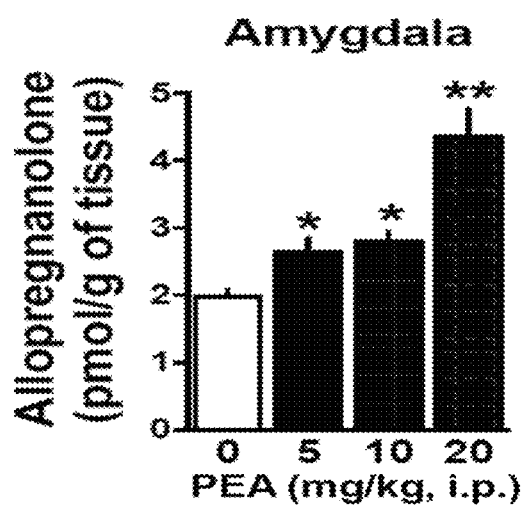
Figure 2E:
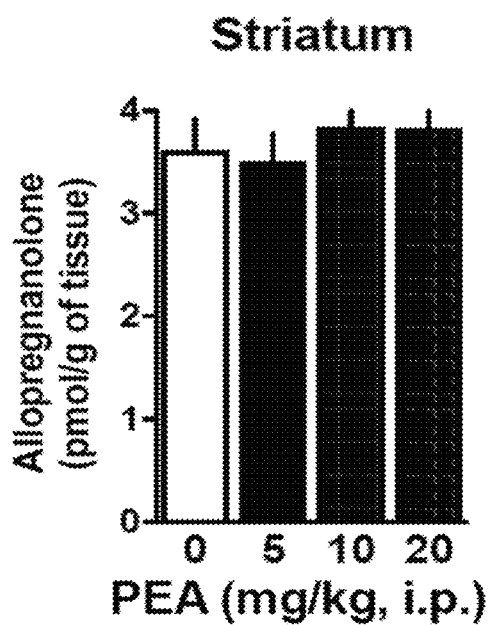

Antidepressant action of PEA in SI mice. When compared to GH-control animals, SI mice's depressive-like behavior was significantly enhanced both in the FST (time of immobility: +41%, $p<0.05$) (FIG. 1E) and in the TST (time of immobility: +41%, $p<0.01$). Despite the lack of effect in GH-control animals, an $EC_{50}$ dose of PEA (10 mg/kg) given to SI mice 1 h before tests significantly decreased the time of immobility in the FST (−40% vs. vehicle-treated SI mice, $p<0.01$; FIG. 1E) and in the TST ["treatment": $F(1, 27)=5.61$, $p=0.025$], "isolation": [$F(1, 27)=2.38$, $p=0.13$; "interaction": [$F(1, 27)=9.24$, $p=0.005$]; −48% vs. vehicle-treated SI mice, $p<0.01$). PEA's antidepressive-like effect was not observed in PPAR-α KO mice (FST: +5%, TST: +12% vs vehicle-treated mice, FIG. 1F).

Figure 7:
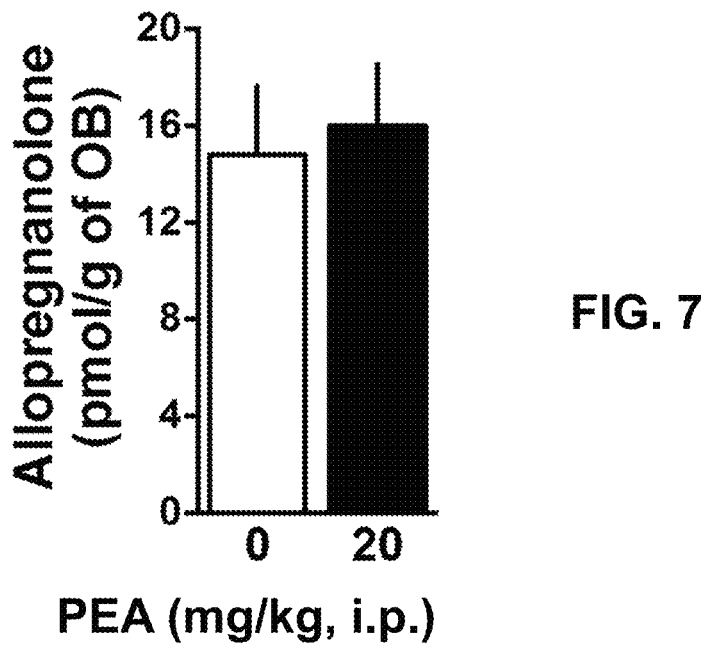
FIG. 7 shows a graph that can demonstrate that PEA (20 mg/kg, i.p., 60 minutes before sacrifice) does not modify Allo concentrations in the olfactory bulb of GH mice. Data are expressed as a mean±SEM of 6-7 mice. Data was analyzed using Student's t-test.

PEA stimulates neurosteroid biosynthesis in several corticolimbic areas of SI mice. A single dose administration of PEA (5-20 mg/kg, i.p.) increased Allo levels after 1 h in the olfactory bulb [$F(3,27)=12.85$; $p<0.0001$], prefrontal cortex [$F(3,26)=3.40$; $p=0.0347$], hippocampus [$F(3,24)=10.45$; $p=0.0002$] and in the amygdala [$F(3,26)=18.03$; $p<0.0001$] of SI mice (FIGS. 2A-2E). This treatment did not affect Allo levels in the striatum (FIGS. 2A-2E). PEA also failed to alter Allo levels in the olfactory bulb of GH control mice (FIG. 7) The neurosteroidogenic effect of PEA was not observed in the serum of SI mice (FIG. 21 The table presented in FIG. 6 summarizes the effect of PEA on Allo's precursor in several corticolimbic areas. Pregnenolone (PE) increased in the olfactory bulb of SI mice [$F(3,26)=9.62$; $p=0.0003$] at the PEA doses of 5 mg/kg (+50%, $p<0.05$) and 10 mg/kg (+69%, $p<0.05$). Progesterone (Prog) levels were increased in the hippocampus [$F(3, 18)=7.42$; $p=0.0028$; 20 mg/kg: +3128%, $p<0.01$], amygdala [$F(3,25)=5.90$; $p=0.0041$; 20 mg/kg: +223%, $p<0.001$], and striatum [$F(3,20)=10.31$; $p=0.0004$; 10 mg/kg: +356%, $p<0.05$; 20 mg/kg: +594%, p<0.001] of PEA-treated SI mice. 5α-dihydroprogesterone (5α-DHP) increased in the hippocampus of SI mice [$F(3, 26)=7.96$; $p=0.0008$; 10 mg/kg: +64%, $p<0.05$; 20 mg/kg: +87%, $p<0.01$].

Figure 8A:
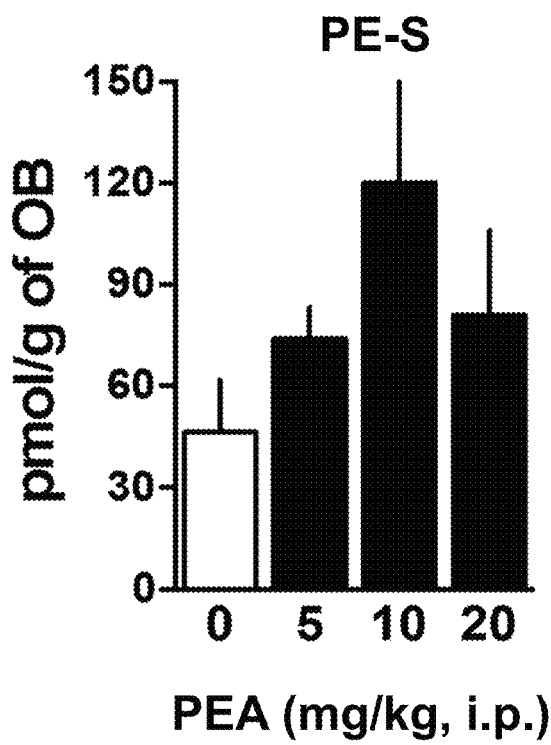
FIGS. 8A-8H shows graphs that can demonstrate the effect of PEA on the sulfated neurosteroid levels in the olfactory bulb (OB) and in the hippocampus (Hippo) of SI mice. Allo-S levels were observed to be significantly increased after a single PEA administration (5, 10 and 20 mg/kg, i.p., 60 minutes before sacrifice) in the hippocampus of SI mice. Data are the mean±SEM of 5-7 mice. *$p<0.05$, when compared with vehicle-treated SI mice. Data was analyzed by one-Way ANOVA followed by Newman-Keuls post hoc analysis.
Figure 8B:
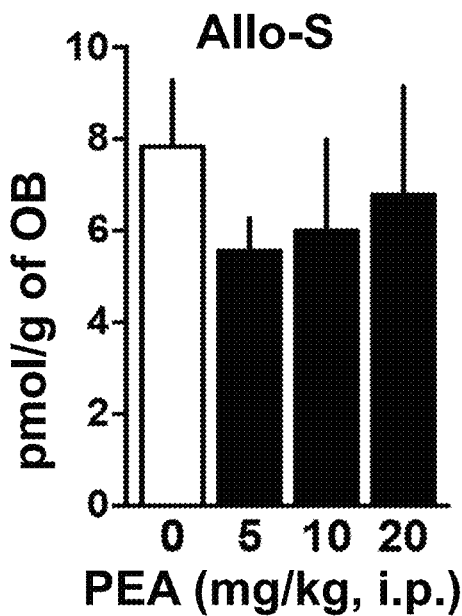
Figure 8C:
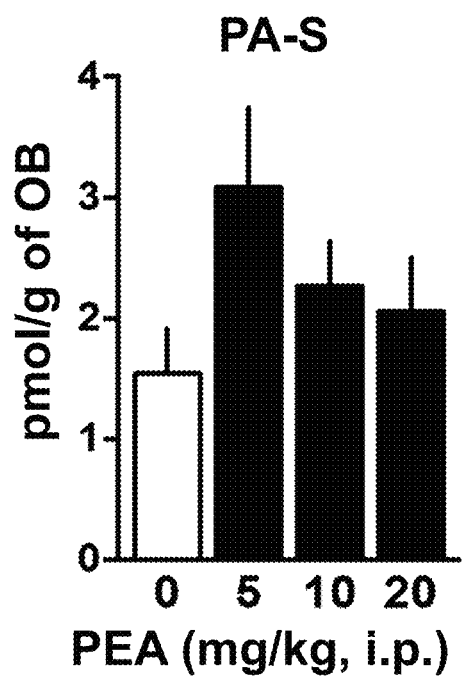
Figure 8D:
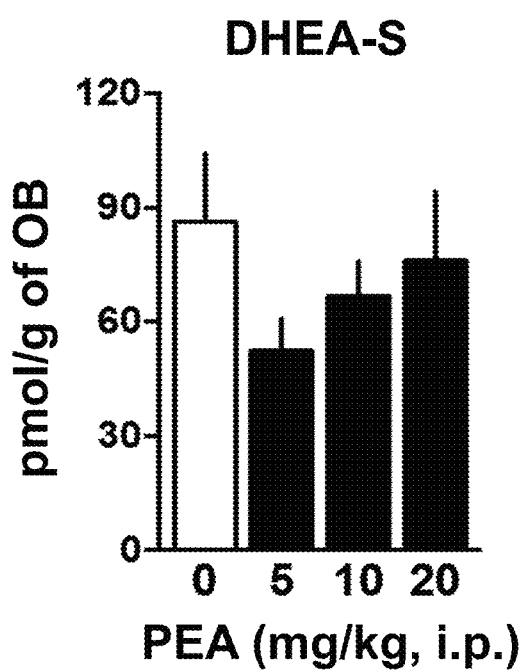
Figure 8E:
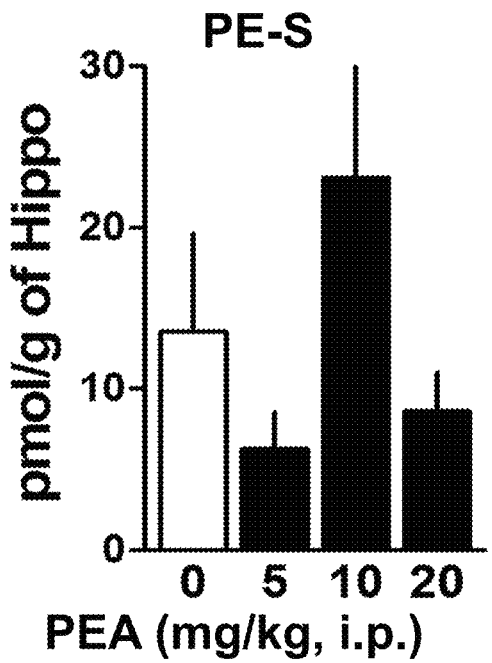
Figure 8F:
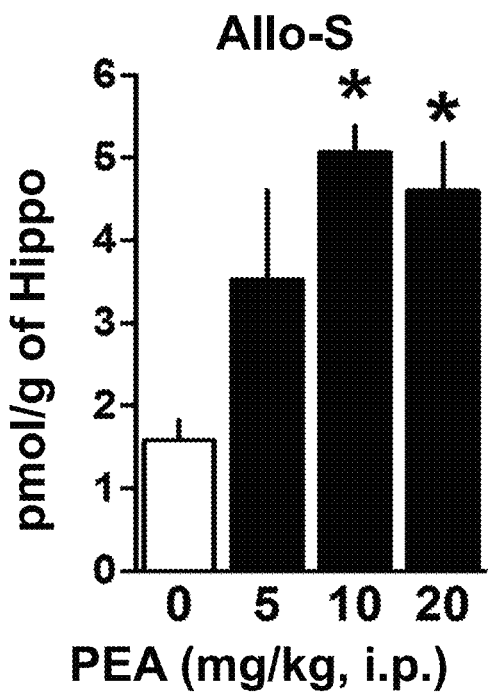
Figure 8G:
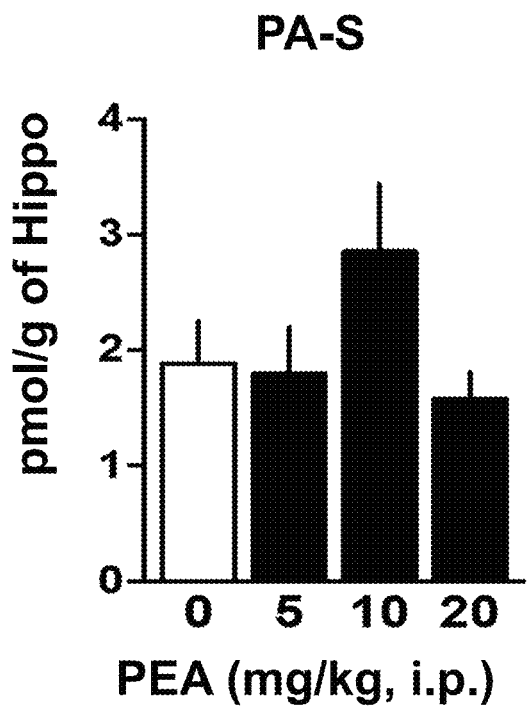
Figure 8H:
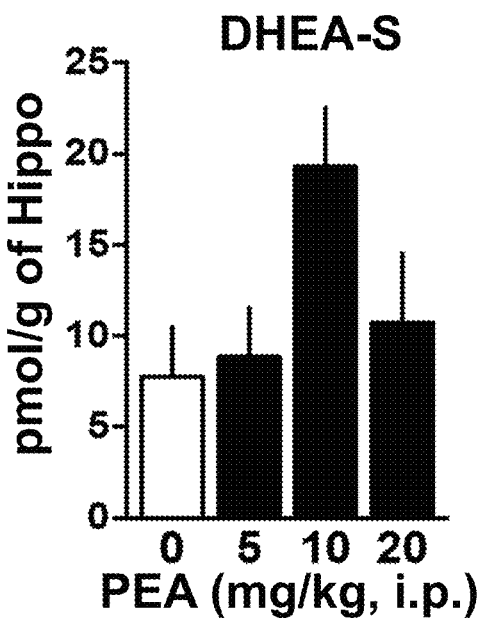

Levels of PE sulfate, Allo sulfate (Allo-S), pregnanolone (PA) sulfate and dehydroepiandrosterone (DHEA) sulfate were measured after PEA administration. PEA was observed to be increased Allo-S in the hippocampus [$F(3,22)=3.75$; $p=0.0285$] after the dose of 10 mg/kg (+100%, $p<0.05$) and 20 mg/kg (+104%, $p<0.05$) (FIG. 8F). This treatment did not affect other sulfated neurosteroid levels (FIGS. 8A-8E and 8G-8H).

PEA-Induced Behavior and Allo Biosynthesis are Mediated by PPAR-α Activation.

Figure 3A:
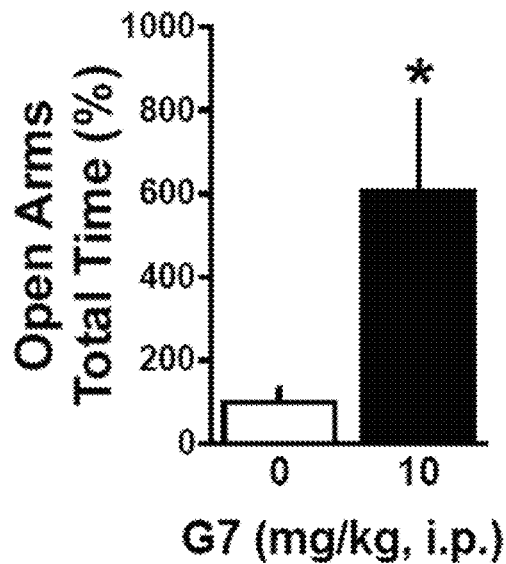
Figure 3B:
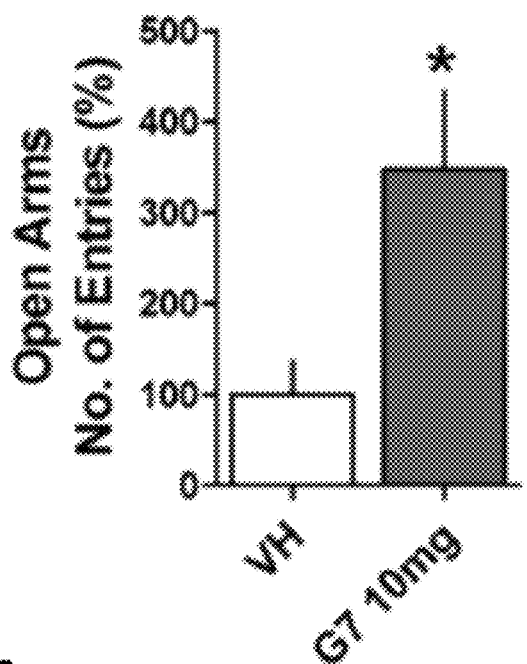
Figure 3C:
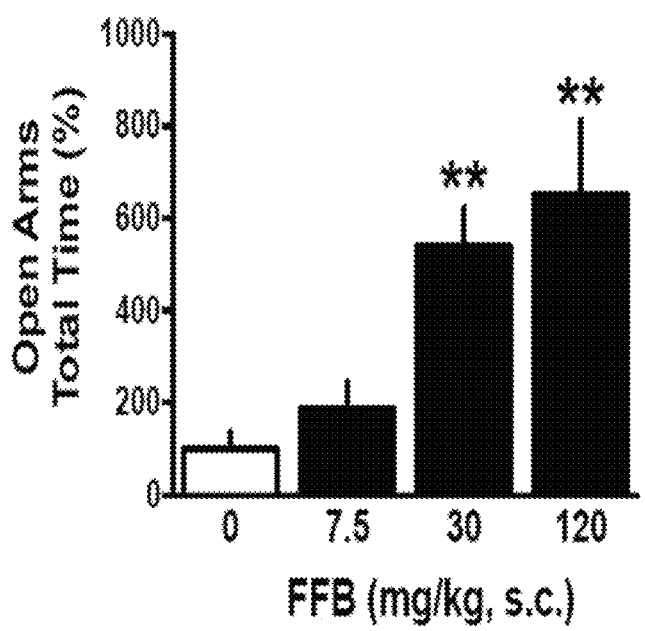

The specificity of PEA's effects at PPAR-α was further analyzed in a pharmacological approach. The PEA $EC_{50}$ dose (10 mg/kg, i.p.) was selected that reduced aggression of SI mice towards a same-sex intruder (34). The PPAR-α synthetic agonist, G7 at the PEA's equimolar dose of 10 mg/kg, i.p., improved anxiety-like behavior in SI mice (time spent in the open arms: +506%, $t(10)=2.281$, $p=0.0457$; number of entries in the open arms: +247%, $t(11)=2.339$, $p=0.0392$) (FIG. 3A). In line with PEA' and G7' effects, the PPAR-α agonist, fenofibrate (dose range 7.5-120 mg/kg, s.c.), dose-dependently induced an anxiolytic-like effect in SI mice [time spent in the open arms: $F(5, 38)=4.991$, $p=0.0013$; number of entries in the open arms: $F(5, 38)=5.601$, $p=0.006$] (FIG. 3C). FIG. 3C can demonstrate that the PPAR-α agonist, fenofibrate (FFB; dose range: 7.5-120 mg/kg, s.c., 1.5 h before test) induces an anxiolytic-like effect in SI mice, as demonstrated by the dose-dependent increase of the time spent in the open arms (7.5 mg/kg: +88%, $p>0.05$; 30 mg/kg: +442%, $p<0.01$; 120 mg/kg: +552%, $p<0.01$). PEA's anxiolytic effect was prevented by pretreatment with the selective PPAR-α antagonist, G6 (3 mg/kg, i.p.) given 30 min before PEA [time spent in the open arms: $F(2, 16)=22.28$; $p<0.0001$; number of entries in the open arms: $F(2, 16)=13.79$; $p=0.0005$] (FIG. 3C).

Figure 3G:
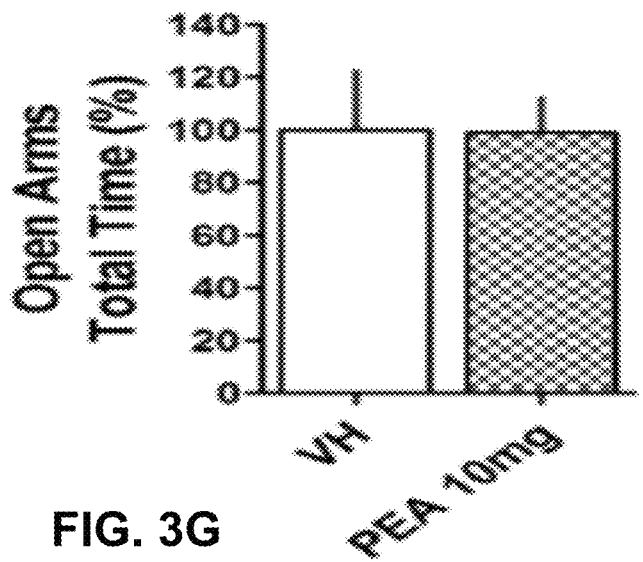
Figure 3H:
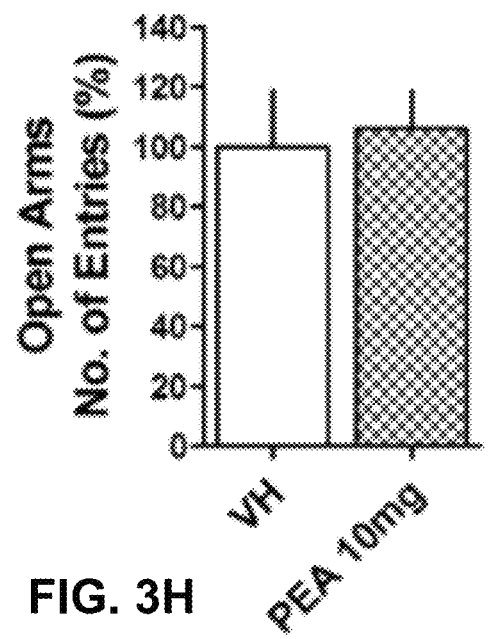
Figure 3I:
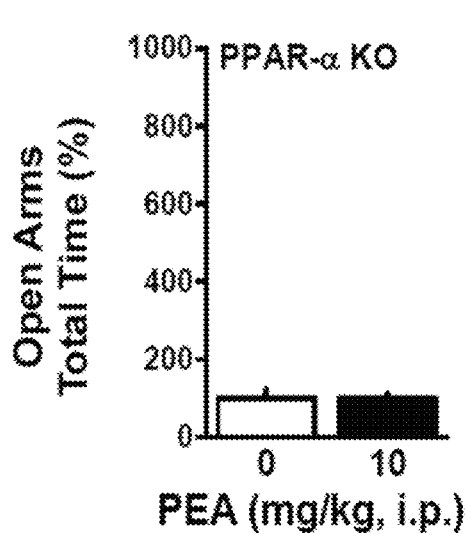
Figure 9:
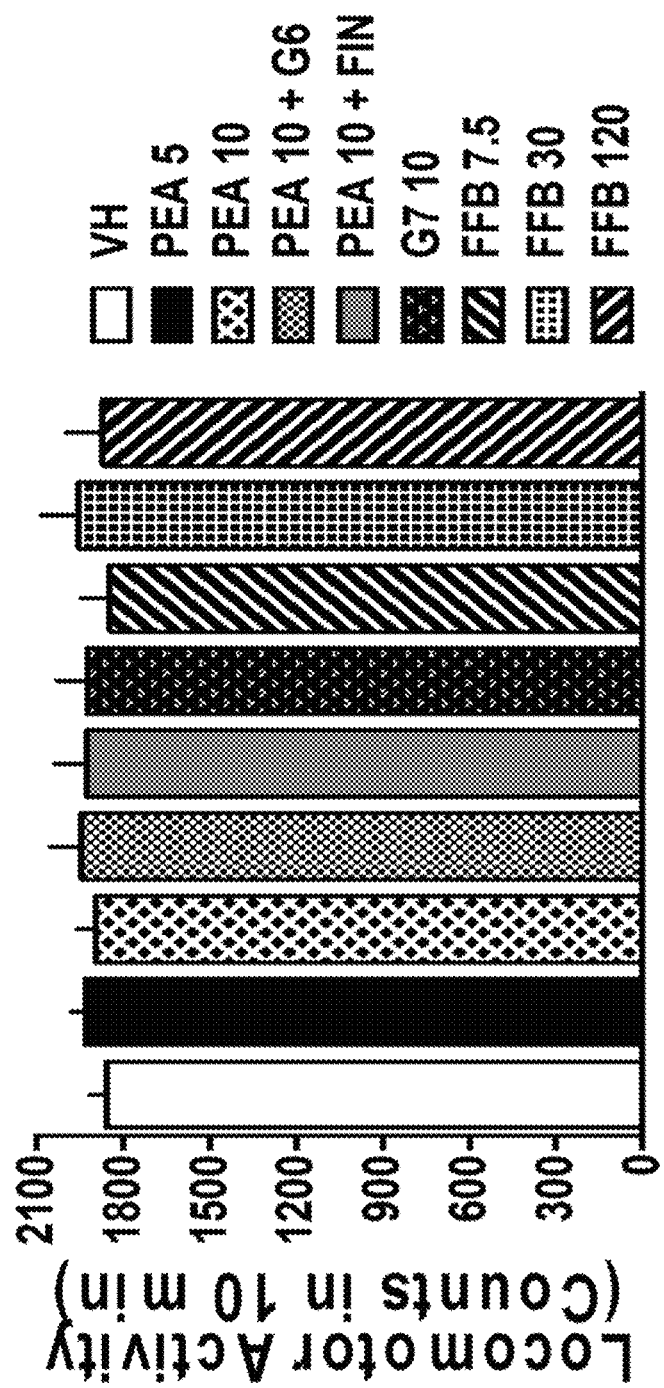
FIG. 9 shows a graph that can demonstrate that PEA, GW 7647 (G7), GW 6471 (G6), fenofibrate (FFB), and finasteride (FIN) do not induce sedation in SI mice. Amounts of compounds in ledgend are in mg/kg. Graph bars represent the effect induced by the administration of PEA (5, 10, and 20 mg/kg, i.p., 60 minutes before behavioral test), G7 (10 mg/kg, i.p., 60 minutes before the behavioral test), G6 (3 mg/kg, i.p., 90 minutes before the behavioral test), or FIN (50 mg/kg, s.c., 150 minutes before behavioral test) on locomotor activity. None of the compounds tested were observed to have a significant effect on locomotion in SI mice. Data represent the mean±SEM of 5-9 mice. Data was analyzed using one-way ANOVA followed by Newman-Keuls post hoc analysis.
Figure 10:
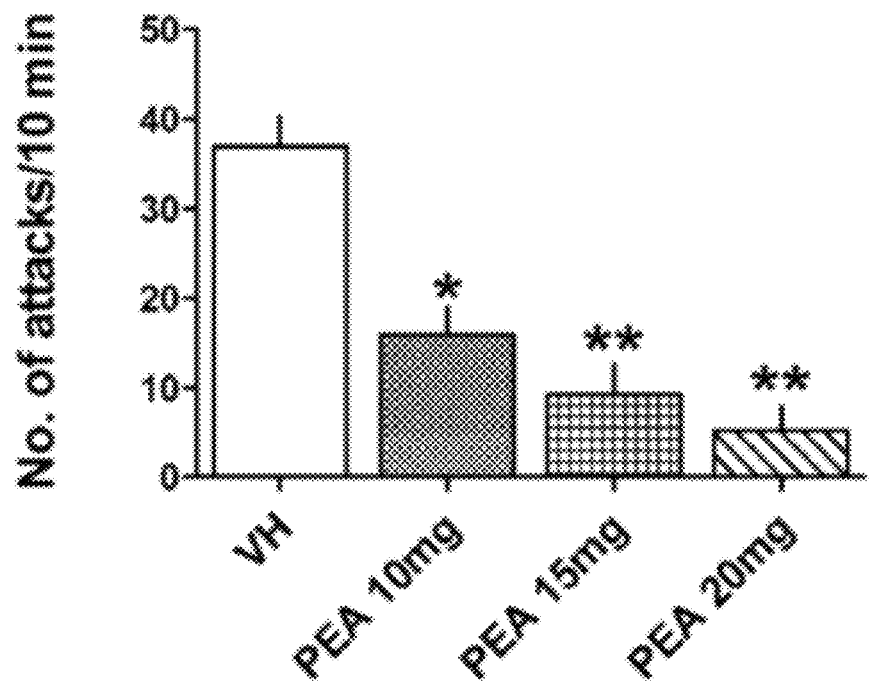
FIG. 10 shows a graph that can demonstrate anti-aggressive behavior induced by PEA in SI mice. PEA was observed to strongly inhibit aggressive behavior in the resident-intruder test (duration of 10 minutes) all the doses tested (10, 15, and 20 mg/kg, i.p., injected 60 minutes before the behavioral test). Data represent the mean±SEM of 13-17 mice. *$p<0.01$; **$p<0.001$, when compared with vehicle-treated control. Data was analyzed using one-way ANOVA followed by Newman-Keuls post hoc analysis.

Furthermore, inhibiting stimulation of Allo biosynthesis, pre-treatment with the 5α-reductase inhibitor, finasteride (50 mg/kg, s.c., 1.5 h before PEA), prevented the anxiolytic-like effect induced by PEA [time spent in the open arms: $F(2, 17)=11.26$; $p=0.001$; number of entries in the open arms: $F(2, 19)=11.96$; $p=0.0006$] (FIG. 3D). FIG. 3E can demonstrate the number of entries into open arms of the elevated plus maze apparatus. The average of vehicle-treated SI mice (VH, white bars) is set as 100%; values of the other experimental group (grey bars) are reported as percentage compared to VH group. Data represented the mean±SEM of 6-7 mice. *$p<0.001$ when compared with vehicle-treated SI mice; #$p<0.01$ and ##$p<0.001$, when compared with PEA at 10 mg. One way ANOVA followed by Newman-Keuls post hoc analysis. FIG. 3F can demonstrate finasteride (a 5α-reductase inhibitor) can block the anxiolytic effect of PEA on elevated plus maze in SI mice. Representation of the effect induced by the co-administration of finasteride (FIN, 50 mg/kg, s/c/ 150 minutes before the behavioral test) and PEA (10 mg·kg, i.p., 60 min before the behavioral test) on the number of entries in the open arms of the elevated plus maze apparatus. Of note, PEA failed to induce anxiolysis in PPAR-α KO SI mice (time spent in the open arms: −1%, $t(9)=0.02$, $p=0.984$; number of entries in the open arms: +6%, $t(9)=0.3$, $p=0.775$) (FIG. 3I). FIGS. 3G-3H show graphs that can demonstrate that PEA (10 mg/kg, i.p.) does not induce anxiolytic effects in SI PPAR-α knockout (KO) mice. PEA was injected 60 minutes before an elevated plus maze test was performed. FIGS. 3G-3H can demonstrate PPAR-α deletion resulted in a failure from PEA to increase the percentage of total time (FIG. 3G) and number of entries (FIG. 3H) in the open arms of the elevated plus maze apparatus in SI mice. Average of SI PPAR-α knockout mice treated with vehicle (VH, white bar) was considered as 100%. Data represent the mean±SEM of 5-6 mice. Data was analyzed using Student's t-test. Finally, locomotion tested by the open field showed no significant differences among all the experimental groups tested (FIG. 9) suggesting a selective effect of PPAR-α stimulation on the modulation of emotional behavior.

Figure 3J:
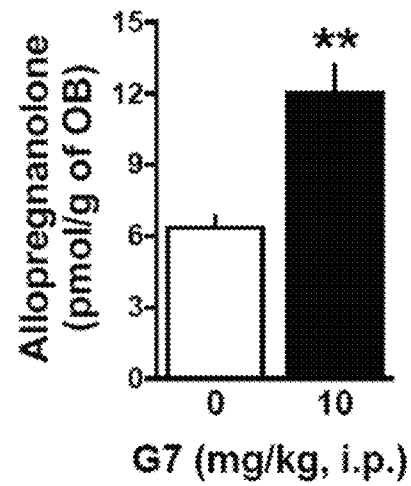
Figure 3K:
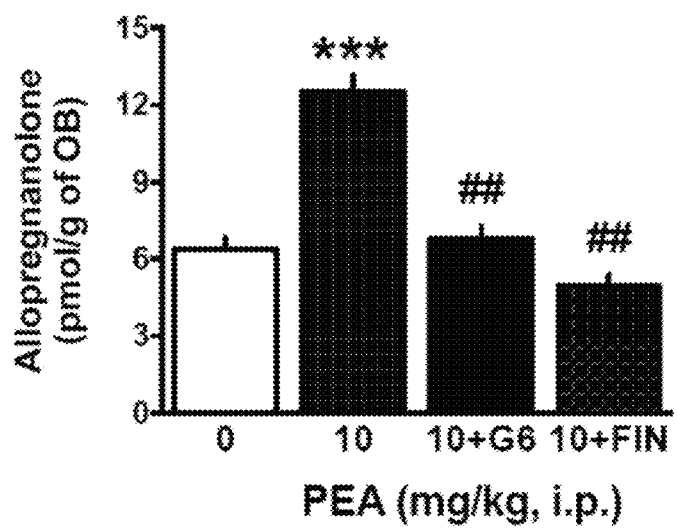
Figure 3L:
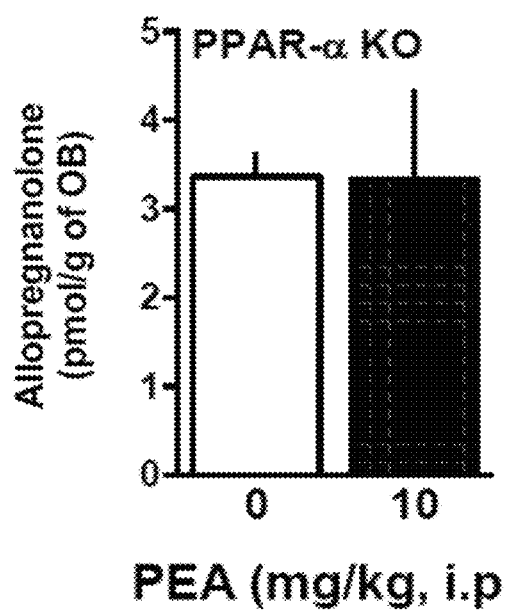

A single administration of the selective PPAR-α agonist, G7 (10 mg/kg, i.p.) increased Allo levels in the olfactory bulb of SI mice (+89%, $t(10)=4.5$, $p=0.0011$) (FIG. 3J). Up-regulation of Allo levels induced by PEA was inhibited by the PPAR-α antagonist, G6 (3 mg/kg, i.p.) [$F(2, 17)=34.48$; $p<0.0001$] (FIG. 3K). Likewise, pre-treatment with finasteride (50 mg/kg) prevented PEA-induced Allo upregulation in SI mice [$F(2, 17)=53.88$; $p<0.0001$] (FIG. 3K). Importantly, PEA failed to affect Allo levels in the olfactory bulb of PPAR-α KO mice (FIG. 3L).

Figure 4C:
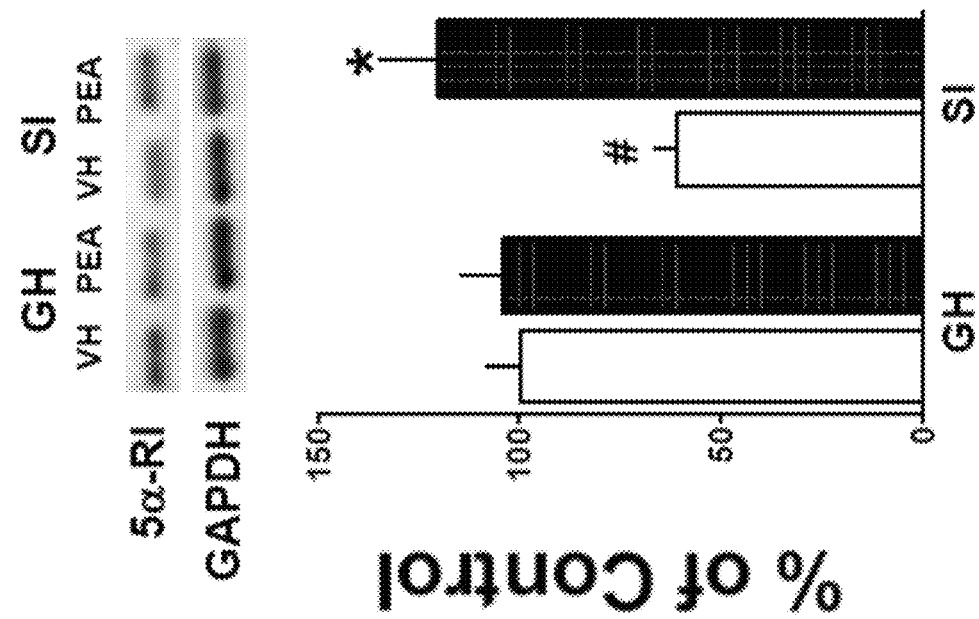
Figure 4D:
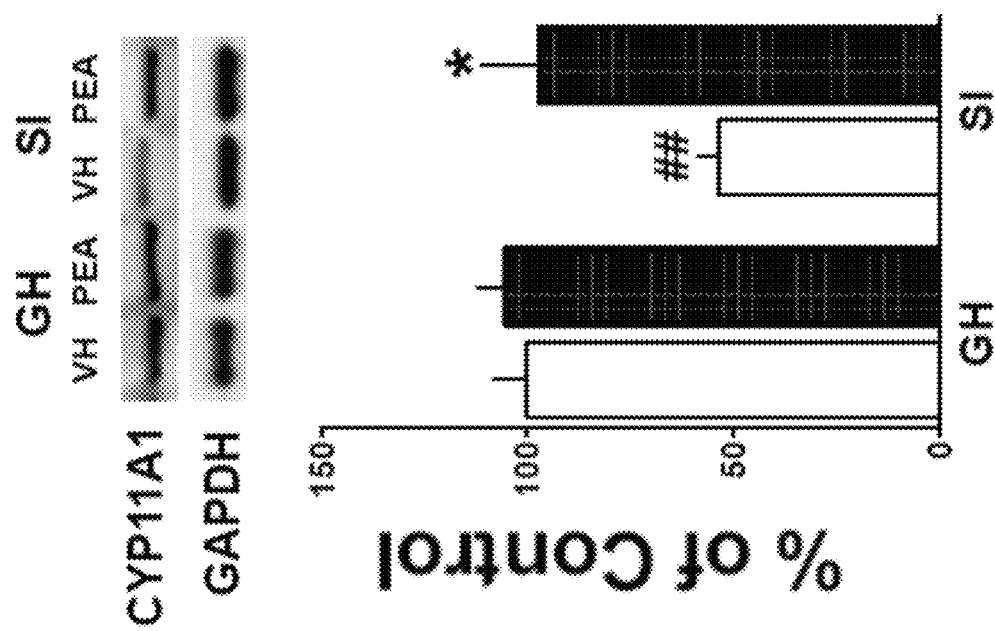

PEA reverts the social isolation-induced hippocampal down-regulation of the protein PPAR-α, StAR, CYP11A1 and 5α-reductase type I. A significant down-regulation in the protein expression of PPAR-α (−49%, $p<0.01$) was observed in the hippocampus of SI mice (FIG. 4A). To understand the mechanism through which PEA stimulates Allo biosynthesis, the expression of proteins involved in neurosteroidogenesis was studied, such as StAR, CYP11A1 and 5α-reductase type I. The expression of these three steroidogenic proteins was observed to be downregulated in the hippocampus of SI mice; specifically, StAR decreased by −80% ($p<0.001$), CYP11A1 by −46% ($p<0.01$), and 5α-reductase type I by −40% ($p<0.05$) (FIG. 4B).

A single PEA EC50 dose (10 mg/kg, i.p.) normalized the expression of any of these proteins at GH-control mice levels (PPAR-α: +109%, $p<0.01$; StAR: +339%, $p<0.001$; CYP11A1: +81%, $p<0.01$; 5α-reductase: +97%, $p<0.01$) (FIGS. 4A-4B).

Discussion.

This study can demonstrate neurobiological evidence that stimulation of PPAR-α by PEA induces the corticolimbic biosynthesis of Allo, an effect that can be directly associated with the improvement of PTSD-like phenotype in SI mice. Specifically, administration of PEA facilitates extinction of contextual fear memory and, most importantly, enhances contextual fear extinction retention. PEA also induces anxiolytic- and antidepressant-like effects in SI mice. Furthermore, PEA's behavioral effects are linked to a normalization of the down-regulated levels of Allo in hippocampus, amygdala, prefrontal cortex and in the olfactory bulb. PEA also elevated Allo-S in the hippocampus. In support of the role of PPAR-α activation in PEA-induced behavior and Allo brain biosynthesis, the PPAR-α synthetic agonist, G7 normalized Allo's levels and improved behavior, whereas; i) antagonism at PPAR-α, ii) pharmacological inhibition of Allo's biosynthetic enzymes, iii) deletion of the PPAR-α gene prevented both PEA behavioral effects and its neurosteroidogenic action.

In addition, this Example can demonstrate that fenofibrate has anxiolytic effects. Fibrates, such as fenofibrate, ciprofibrate and clofibrate have been prescribed for decades to treat dyslipidemia with a safe pharmacological profile (2). Fenofibrate restores the VTA's dopaminergic responses to appetitive stimuli and motivation to sucrose preference in chronically-stressed rats, suggesting an antidepressant-like activity (36). Finally, fenofibrate's mechanism may include a neurosteroidogenic effect through PPAR-α activation. PEA and fenofibrate are already FDA approved; hence, these data entail immediate translational impact to treat neuropsychiatric disorders.

Improvement of fear extinction and anxiolytic-like effects in chronically-stressed mice were observed after treatment with natural and synthetic cannabinoids (e.g., cannabidiol, AEA, HU210, WIN55,212-2) that, in addition to binding CB1, activate PPAR-α (10). Serum concentrations of PEA and OEA are increased in the immediate aftermath of a social stressor (39), before decreasing during recovery (40). Exposure to stressful stimuli evokes a fast induction of the enzyme FAAH, which reduces circulating AEA and PEA levels (40). Exposure to predator stressors reduces peripheral PEA and OEA levels in rodents (41). Circulating eCB levels are also altered in PTSD patients. An inverse correlation between PTSD symptoms and reduced hair levels of PEA, OEA and SEA has been shown in males and females (11), and a recent study suggests that PEA adjunctive therapy to citalopram improves symptoms in depressed patients (42). Finally, intense exercise, by increasing serum PEA and OEA levels may be important to counteract depression and PTSD (43).

While extensive studies have showed that CB1 regulates emotions and stress responses (5), the new role for PPAR-α on emotions is just emerging and poorly understood. The impact of PPAR-α in behavior regulation is underscored by studies showing that, like CB1, PPAR-α is expressed in glutamatergic neurons of emotion-relevant areas (amygdala, hippocampus, frontal cortex) (3, 44). However, unlike PPAR-α, targeting CB1 results in psychotomimetic effects that limit its pharmacological potentials (45). Of note, glutamatergic neurons in corticolimbic areas also express an intense Allo neosynthesis, which, similarly to the eCB system, regulates synaptic transmission and mediates plasticity influencing synaptic formation and neurogenesis in response to stress (16, 17). In mouse models of stress, decreased Allo levels in corticolimbic neurons have been linked to anxiety-like behavior and increased contextual fear responses, and supplementing Allo or giving neurosteroidogenic agents rescues behavioral deficits (25, 28, 46).

The relevance of the PEA-induced increase of Allo-S observed in this Example, in addition to enhancing Allo levels, is two-fold. Sulfated neurosteroids, such as Allo-S and its isomer, pregnanolone sulfate, negatively regulate tonic neurotransmission mediated by NMDA receptors (47). Targeting NMDA receptors in circuitry with relevance for mood disorders is becoming a strategy in antidepressant treatment (48). This therapeutic trend is highlighted by growing evidence of rapid antidepressant action of molecules (e.g. ketamine) that function as NMDA antagonists (49). Hence, it is conceivable that PEA-induced Allo and Allo-S up-regulation may act in concert, on one hand, by potentiating $GABA_A$ receptor-mediated inhibition and on the other, Allo-S may be involved in mechanisms inhibiting tonic NMDA-mediated excitatory neurotransmission, which could counteract cognitive and emotional deficits. In kind, recent findings have shown PEA improves neurological (e.g., normalization of astrocytic function and glutamatergic transmission) and behavioral dysfunctions in animal models of PTSD, traumatic brain injury and Alzheimer's disease (34, 50, 51).

Figure 5:
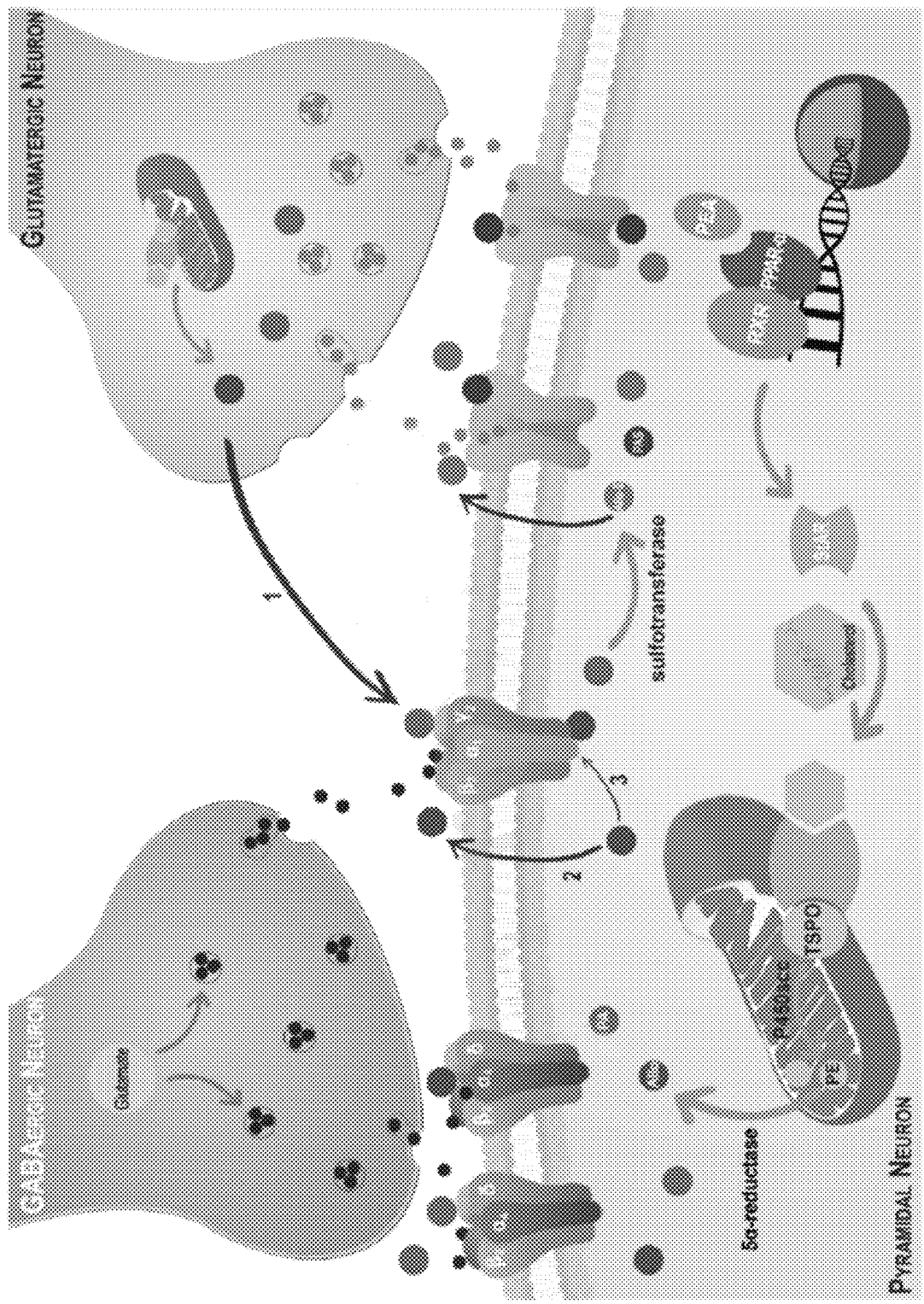
FIG. 5 shows a schematic that can demonstrate the regulation of emotional behavior via endocannabinoid and neurosteroid systems cross-talk.

In SI mice, decreased Allo levels correlate with the down-regulation of the rate-limiting step enzyme, 5α-reductase type I in cortical and hippocampal pyramidal neurons. This conforms with human studies that show 5α-reductase is down-regulated in the prefrontal cortex of depressed male patients (23). In PTSD, a gender-dependent disruption in the Allo biosynthetic enzyme pathway was found at the level of 3α-hydroxysteroid dehydrogenase in women and 5α-reductase in men (22). Here, it was observed that PEA up-regulates StAR, which participates in the translocation of cholesterol into the inner mitochondrial membrane, and CYP11A1, which is the first-step enzyme converting cholesterol into pregnenolone (the precursor of all neurosteroids), in the hippocampus of SI mice. Moreover, PEA increases the hippocampal expression of 5α-reductase type I. It was also demonstrated that social isolation down-regulates the hippocampal expression of PPAR-α and administering PEA reverts this effect. Without being bound by theory, PEA-induced up-regulation of PPAR-α can normalize behavior by enhancing PPAR-α binding at the consensus regions PPAR response element (PPRE) on the promoter of neurosteroidogenic genes to initiate transcription (FIG. 5). In support, the down-regulation of PPAR-α expression can be normalized by application of PEA in primary astrocytes (52), and PEA, G7 and Wy-14643 increased the expression of PPAR-α mRNA when applied topically to mouse skin (53). Without being bound by theory PPAR-α can regulate the expression of genes, including lipid/hormone transport, cholesterol transport and metabolism and mitochondrial oxidation (54). In this Example, the effects of PPAR-α agonists on neurosteroidogenesis appeared 1 h after administration. This relatively fast-effect could be supported by the evidence that activation of PPAR-α by agonists induces the up-regulation of "early response genes", including C-FOS, JUNB, C-JUN, JUND and MYC, which can be and transcribed within minutes, without requiring de novo protein synthesis (55).

The demonstration that PPAR-α activation by endogenous (PEA) or synthetic ligands (G7, fenofibrate) improves emotions by stimulating corticolimbic Allo biosynthesis can provide therapeutic strategies to treat PTSD and depression more efficiently.

REFERENCES FOR EXAMPLE 1

1. Petrosino S, Di Marzo VBr J Pharmacol 2017; 174: 1349-1365.
2. Rigano D, Sirignano C, Taglialatela-Scafati O. Acta Pharm Sin B 2017; 7: 427-438.
3. Moreno S, Farioli-Vecchioli, Cerù M P. Neuroscience 2004; 123:131-45.
4. Mattace Raso G, et al. Pharmacol Res 2014; 86: 32-41.
5. Häring M, Guggenhuber S, Lutz B. Neuroscience 2012; 204: 145-58.
6. Neumeister A, et al. Psychoneuroendocrinology 2014; 51: 577-84.
7. Hill M N, et al. Psychoneuroendocrinology 2009; 34: 1257-62.
8. Hill M N, et al. Psychoneuroendocrinology 2013; 38: 2952-61.
9. Hill M N, Gorzalka B. CNS Neurol Disord Drug Targets 2009; 8: 451-8.
10. O'Sullivan S E. Br J Pharmacol 2007; 152: 576-582.
11. Wilker S, et al. Psychoneuroendocrinology 2016; 67: 198-206.
12. Smaga I, et al. Neurotox Res 2014; 26: 190-206.
13. Sasso O, et al. Eur Neuropsychopharmacol 2010; 20: 195-206
14. Raso G M, et al. J Neuroendocrinol 2011; 23: 591-600.
15. Pinna G, et al. Neuropharmacology 2000; 39: 440-8.
16. Agis-Balboa R C, et al. Proc Natl Acad Sci USA 2006; 103: 14602-7.

17. Agis-Balboa R C, et al. Proc Natl Acad Sci USA 2007; 104: 18736-41.
18. Locci A, Pinna G. Br J Pharmacol 2017; 174: 3226-3241.
19. Qiu Z K, et al. Neurosci Lett 2015; 602: 162-6.
20. Romeo E, et al. Am J Psychiatry 1998; 155: 910-3.
21. Uzunova V, et al. Proc Natl Acad Sci USA 1998; 95: 3239-44.
22. Rasmusson A M, et al. Biol Psychiatry 2006; 60: 704-13.
23. Agis-Balboa R C, et al. Psychopharmacology (Berl) 2014; 231: 3569-80.
24. Pinna G, et al. Proc Natl Acad Sci USA 2003; 100: 2035-40.
25. Pibiri F, et al. Proc Natl Acad Sci USA 2008; 105: 5567-72.
26. Pinna G, Costa E, Guidotti A. Curr Opin Pharmacol 2009; 9:24-30.
27. Lovick T. J Psychopharmacol 2013; 27: 1180-5.
28. Pinna G, Front Cell Neurosci 2014; 8: 256.
29. Pinna G, et al. Proc Natl Acad Sci USA 2006; 103: 4275-80.
30. Can A, et al. The mouse forced swim test. J Vis Exp 2012; 59: e3638.
31. Can A, et al. J Vis Exp 2012; 59: e3769.
32. Uzunov D P, et al. Proc Natl Acad Sci USA 1996; 93: 12599-604.
33. Locci A, et al. Horm Behav 2017; 87: 35-46.
34. Locci A, et al. Front Cell Neurosci 2017; 11: 208.
35. Le Foll B, et al. Curr Drug Targets 2013; 14: 768-76.
36. Scheggi S, et al. Neuropharmacology 2016; 110: 251-259.
37. Puligheddu M, et al. Epilepsia 2017; 58: 1762-1770.
38. Umathe S N, Manna S S, Jain N S. Behav Brain Res 2011; 223: 125-34.
39. Dlugos A, et al. Neuropsychopharmacology 2012; 37: 2416-27.
40. Hill M N, et al. Neuropsychopharmacology 2009; 34: 2733-45.
41. Holman E A, et al. Psychosom Med 2014; 76: 20-28.
42. Ghazizadeh-Hashemi M, et al. J Affect Disord 2018; 232: 127-133.
43. Heyman E, et al. Psychoneuroendocrinology 2012; 37: 844-51.
44. Katona I. Curr Top Behav Neurosci 2009; 1: 65-86
45. Janero D R. Expert Opin Emerg Drugs 2012; 17: 17-29.
46. Pinna G, et al. Neurochem Res 2008; 33: 1990-2007.
47. Vyklicky V, et al. J Neurosci 2016; 36: 2161-75.
48. Dang Y H, et al. Curr Pharm Des 2014; 20: 5151-9.
49. Jafarinia M, et al. J Affect Disord 2016; 204: 1-8.
50. Guida F, et al. Front Pharmacol 2017; 8: 95.
51. Scuderi C, et al. Transl Psychiatry 2018; 8: 32.
52. Scuderi C, et al. J Cell Mol Med 2011; 15: 2664-74.
53. Lo Verme J, et al. Mol Pharmacol 2005; 67: 15-9.
54. Rakhshandehroo M, Hooiveld G, Müller M, Kersten S. PloS One2009; 4: e6796.
55. Ledwith B J, et al. Mol Carcinog 1993; 8: 20-7.

Example 2

Introduction: Exposure to traumatic experiences is associated with a drastic increase in the risk of developing psychiatric disorders, including major depressive disorder (MDD) and post-traumatic stress disorder (PTSD). These debilitating conditions affect 8-16% of adult population in the United States and MDD alone is the most common neuropsychiatric disease worldwide (Kessler et al., 2005; Berton and Nestler, 2006; Whiteford et al., 2013).

Severe traumas, including abuse in women, child abuse and neglect, combat situations or sexual assault, result in a particularly serious form of chronic PTSD that is often comorbid with MDD and suicide (Prigerson et al., 2001), and is associated with a marked increase in vulnerability to substance and alcohol abuse as well as mood disorders such as bipolar disorder, generalized anxiety, and phobias (Famularo et al., 1992; Agid et al., 1999; Heim and Nemeroff, 2001; Kendler et al., 2004). Furthermore, a history of early-life trauma can predict a more severe and chronic depression and inadequate response to both pharmacological and psychotherapeutic treatments and even failure of treatment response in adulthood (Kessler, 1997; Zlotnick et al., 1997; Lanquillon et al., 2000; Wersma et al., 2009; Shamseddeen et al., 2011; Nanni et al., 2012). For example, multiple childhood adverse experiences increased fourfold the risk of developing MDD during adult life (Felitti et al., 1998), and increased 2-5 times the risk of attempted suicide in childhood, adolescence, and adulthood (Dube et al., 2001). A study in women demonstrated a tight correlation between sexual or physical abuse in childhood and increased symptoms of anxiety, MDD, addiction and suicide in adulthood (McCauley et al., 1997). Of note, abuse in general but most notably, abuse occurring between 4 and 7 years of age predicted a lower response to 8 weeks of selective serotonin reuptake inhibitors (SSRIs) (Williams et al., 2016). SSRIs remain the most used antidepressants for decades, however, only 40-50% of MDD patients achieve remission, and more than ⅓ develop pharmacoresistance (Golden et al., 2002; Rush et al., 2006; Kemp et al., 2008). Likewise, for PTSD treatment, the only drugs approved by the FDA are the SSRIs sertraline and paroxetine but only 20% of SSRI-treated PTSD patients do not relapse (Westenberg, 1996; Walderhaug et al., 2010; Ipser and Stein, 2012). The reasons underlying SSRI-resistance can be multiple and can be found in genetic factors, pharmacokinetics, type of trauma, and comorbidity with other mental disorders (El-Hage et al., 2013; Willner et al., 2013). Failure to achieve full remission from MDD and PTSD symptoms in a large portion of patients indicates the need to develop alternative drugs for the treatment of non-responders. Both MDD and PTSD are associated with altered GABAergic neurotransmission. For example, adolescent as well as adult MDD patients show a reduction of plasma, CSF, and cerebral cortex GABA concentrations (Luscher et al., 2011). Moreover, the expression of several GABAA receptor subunits is altered in brain areas of MDD patients (Merali et al., 2004; Choudary et al., 2005; Klempan et al., 2009; Sequeira et al., 2009; Fatemi et al., 2013). Male Dutch veterans affected by PTSD show a significant reduction of benzodiazepine binding in cortex, hippocampus, and hypothalamus (Geuze et al., 2008), while male Viet Nam veterans show reduced binding in prefrontal cortex, Broadmann area 9 (Bremner et al., 2000). Furthermore, MDD and PTSD patients show low plasma, CSF, and brain levels of the GABAA receptor-active, neurosteroid allopregnanolone (Allo) (Romeo et al., 1998; van Broekhoven and Verkes, 2003; Uzunova et al., 2006; Agis-Balboa et al., 2014). Depression during pregnancy and post-partum is likewise associated with changes in Allo levels (Nemeroff, 2008). Importantly, treatment with SSRIs normalizes CSF, plasma, and brain Allo levels in MDD patients, an effect associated with improved symptoms, while patients who fail to respond to SSRIs also fail to increase Allo levels (Romeo et al., 1998; Uzunova et al., 2006). Mouse stress models are probably the best translational approach to reproduce some of the behavioral and neurochemical alterations observed in MDD and PTSD patients. For example, the socially isolated (SI) mouse, a putative rodent model of PTSD, shows a time-dependent downregulation of corticolimbic Allo levels associated with behavioral dysfunction, such as aggressive behavior, anxietylike behavior and altered contextual fear responses (Dong et al., 2001; Pinna et al., 2003; Pibiri et al., 2008; Nin et al., 2011a; Locci and Pinna, 2017a; Rasmusson et al., 2017). Furthermore, SI mice show changes in the expression of several $GABA_A$ receptor subunits, which similar to PTSD patients, result in resistance to benzodiazepine's pharmacological effects (Pinna et al., 2006b; Geuze et al., 2008; Pibiri et al., 2008; Nin et al., 2011b). Intriguingly, administration of low doses of SSRIs, acting as selective brain steroidogenic stimulants (SBSSs), normalize brain Allo levels and improve behavior in SI mice (Pinna et al., 2003, 2009). Likewise, administration of the Allo analog, ganaxolone (GNX), results in a dose-dependent improvement of emotional behavior (Pinna and Rasmusson, 2014).

Without being bound by theory, it is thought that early (PND 21) adolescence social isolation contributes to a more rapid and severe development of aggression and a lower pharmacological response to S-fluoxetine (S-FLX) than mice isolated in late adolescence (PND 45), which can be demonstrated by (i) a lower reduction in the rate of aggression, (ii) a lower duration of the drugs effect, and (iii) a higher percent of "non-responders." The pharmacological effect of S-FLX with that of neurosteroid-based treatments, including the endocannabinoid, N-palmitoylethanolamine (PEA) that can stimulates brain Allo biosynthesis.

This Example can demonstrate that a single dose treatment with S-FLX and PEA induced a stronger reduction of aggressive behavior in late than in early adolescent SI mice. Moreover, the rate of non-responders for these compounds was higher in early SI mice and the pharmacological effect of these compounds was more enduring in late than early adolescent SI mice. These data can show that early SI mice develop earlier and more severe aggression than late SI mice and compounds like and PEA are stronger agents in counteracting these behavioral deficits.

Materials and Methods.

Animals. Male Swiss-Webster mice (Harlan Breeders) (18-30 g body weight), maintained under a 12-h dark/light cycle with food and water ad libitum were used for all experiments. Mice were housed individually in a cage of dimensions 24 cm×17 cm×12 cm. For these experiments, two mice experimental groups were used for the study of drug effect in different age conditions. The first group was isolated at 21 days ("early adolescent SI mice," PND 21), while the second group at 45 days ("late adolescent SI mice," PND 45). The animals were exposed to behavioral testing after 6 weeks of isolation. The vivarium temperature was kept at 24° C. and the humidity near 65%.

Drug Treatments. S-fluoxetine (S-FLX) (0.375-1.5 mg/kg) was obtained from Eli Lilly and Company (Indianapolis, Ind., United States). N-palmitoylethanolamine (PEA; 5-20 mg/kg) was purchased from Epitech Group Research lab (Saccolongo, Italy). All the drugs were dissolved in saline solution containing 0.5% Tween-80 (Sigma Aldrich, St. Louis, Mo., United States), and were injected intraperitoneally (i.p.), 60 min before behavioral tests.

Resident-Intruder Test. To test aggression, a male intruder mouse of the same strain as the resident mouse, was placed in a resident home cage (24 cm×17 cm×12 cm) and resident-intruder interactions were videotaped for 10 min. Aggressive behavior of SI mice was characterized by an initial pattern of exploratory activity around the intruder, followed by rearing and tail rattle, accompanied within a few seconds by wrestling and/or a violent biting attacks. The total number of wrestling and attacks during the 10 min observation period was measured as previously described (Pinna et al., 2003, 2005), 60 min after drug administration. For every drug studied, SI mice were first exposed to three behavioral sessions, and then the average of basal aggression level for every single SI mouse was calculated; 2 days later, aggression levels following treatment were tested. Treated animals showing a reduction of the number of attacks less than 30% vs. the respective basal control values were considered as "low- to non-responders."

Locomotor Activity. A computerized AccuScan 12 Animal Activity Monitoring System (Columbus Instruments, Columbus, Ohio, United States) assisted by VERSAMAX software (AccuScan Instruments, Columbus, Ohio, United States) was used to quantify locomotor activity (Pinna et al., 1997, 2006a). Each activity cage consisted of a 20 cm×20 cm×20 cm Perspex box surrounded by horizontal and vertical infrared sensor beams. Horizontal sensors' beam interruptions were taken as a measure of horizontal activity. Activity was recorded from SI mice for 10 min beginning 60 min after a single injection of the drug.

Statistical Analyses. Results are presented as means±SEMs unless otherwise indicated. Student's t-test, one-way ANOVA and two-way ANOVA repeated measures followed by Bonferroni post hoc test were performed to analyze experimental data; significance was set at p<0.05. $EC_{50}$ values were calculated from dose-response curves analyzed by the "quantal dose-response: probits test" using the computer program of Tallarida and Murray equipped with a statistical package (Tallarida and Murray, 1987). Statistical comparisons among the different EC50s were performed with the "cohort package software." (available at cohort.com).

Results.

Figure 11:
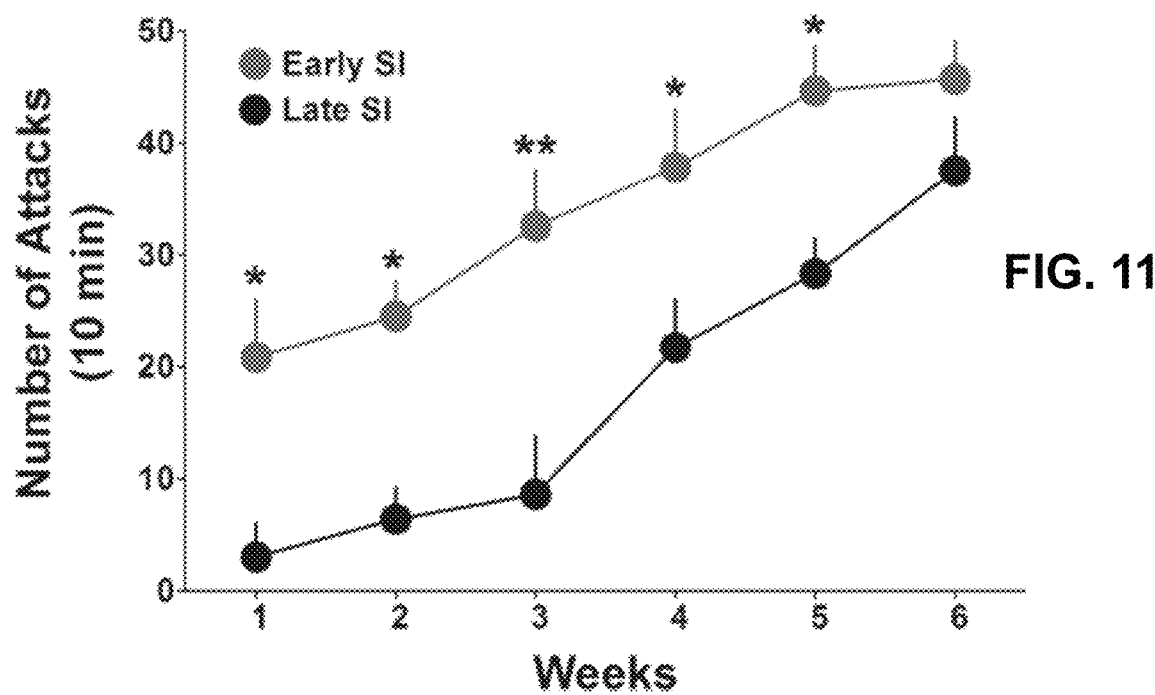
FIG. 11 shows a graph that can demonstrate onset of aggressive behavior in early and late adolescent SI mice. Representation of the development of the aggressive behavior in early (light grey) and late (black) adolescent SI mice from week 1 to 6 of social isolation. Early adolescent social isolation (started at day 21 of life, PND 21) induced a more severe development of aggression compared to late adolescent isolation (started at day 45 of life, PND 45). Data represent the mean±SEM of 15 mice. *p<0.05 and **p<0.001, when compared with late adolescent SI mice at the same time point.

Development of Aggressive Behavior in Late and Early SI Adolescent Mice. The basal levels of aggressive behavior were determined in both late and early SI mice starting from the first week of isolation, by testing resident-intruder interactions once a week for 6 weeks (FIG. 11). It was observed that early isolation, which was started at PND 21, induced a more rapid and severe development of aggression compared to late social isolation, which was started at PND 45. Two-way ANOVA repeated measures revealed a significant effect of "onset of isolation" [F(1, 140) D 42.23; p<0.0001], an effect of "time of test" [F(5, 140) D 16.67; p<0.0001], but no interaction between factors [F(5, 140) D 0.763; p D 0.578]. Bonferroni post hoc test showed a significant difference in the aggressive behavior between late and early SI mice in every week tested except week 6 (FIG. 11). Aggression levels were studied only in SI mice given that group-housed conditions do not account for relevant levels of aggression (Pinna et al., 2003, 2005).

Figure 12A:
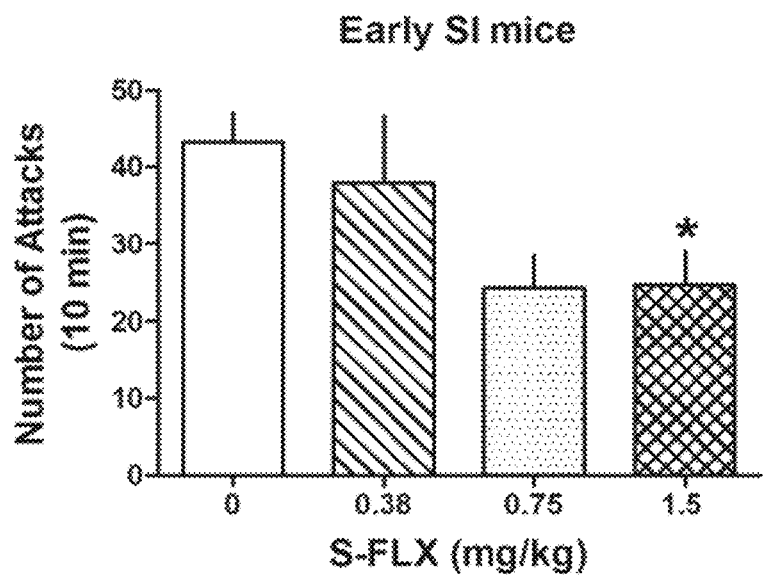
FIGS. 12A-12B show graphs that can demonstrate S-fluoxetine (S-FLX) can decrease aggressive behavior in early and late adolescent SI mice. S-FLX at the doses of 0.375, 0.75, and 1.5 mg/kg, i.p., was administered both to early (FIG. 12A) and late (FIG. 12B) adolescent SI mice 60 min before the resident-intruder test. In late adolescent SI mice, S-FLX reduced aggression at the dose of 0.75 mg/kg with an EC50 dose of 0.85 mg/kg, while in early adolescent SI mice, S-FLX induced a decrease of aggression with an EC50 dose of >1.5 mg/kg. Data represent the mean±SEM of 13-18 mice. *p<0.05; p<0.01; *p<0.001, when compared with basal control levels of aggression.
Figure 12B:
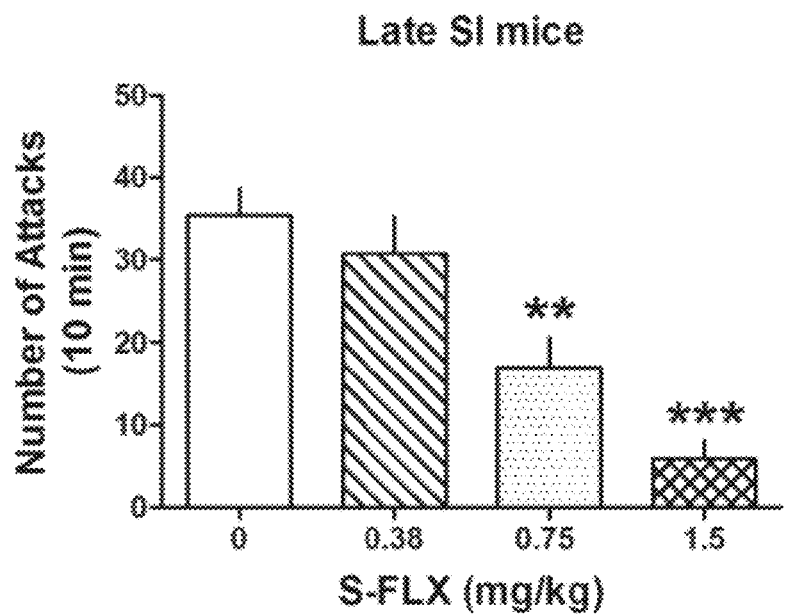

S-FLX More Potently Improves Aggression in Late Than Early SI Mice. Administration of several doses of the SSRI, S-FLX (0.375, 0.75, and 1.5 mg/kg, i.p.) resulted in a stronger dose-dependent decrease of aggression in late than in early SI resident mice toward a same-sex intruder. One-way ANOVA showed that S-FLX reduced aggression in both late [F(3,84) D 13.08; p<0.0001] and early SI mice [F(3, 91)=3.823; p=0.013] (FIGS. 12A-12B). Bonferroni post hoc test showed a significant reduction in the number of attacks at the dose of 0.75 mg/kg (−52%, p<0.01, n=13) as well as at 1.5 mg/kg (−83%, p<0.001, n=17) in late SI mice ($EC_{50}$ dose=0.85 mg/kg), but only at the highest dose (1.5 mg/kg) in early SI mice (−43% vs. basal value, p<0.05, n=18) ($EC_{50}$ dose>1.5 mg/kg). The S-FLX dose of 1.5 mg/kg was more potent in late [+316%, t(33) D 3.761, p=0.0007] than early SI mice.

Figure 13A:
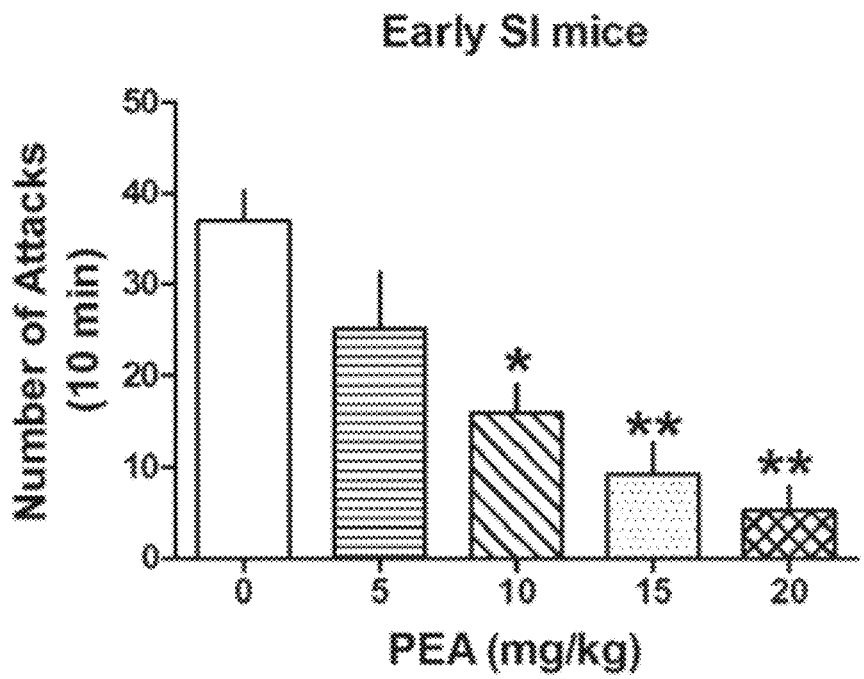
FIGS. 13A-13B show graphs that can demonstrate that the endocannabinoid PEA strongly decreases aggressive behavior in early and late SI mice. PEA at the doses of 5, 10, 15, and 20 mg/kg was administered both to early (FIG. 13A) and late (FIG. 13B) SI mice 60 min before the exposure to a resident-intruder test. The EC50 values were 8 and 6.5 mg/kg, respectively. Data represent the mean±SEM of 7-17 mice. *p<0.01; **p<0.001, when compared with basal control levels of aggression.
Figure 13B:
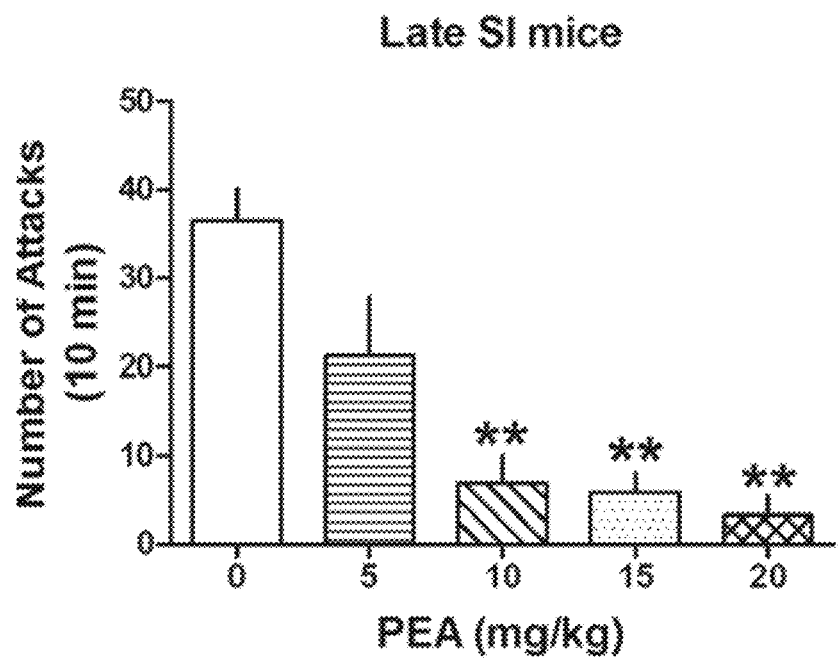

PEA Inhibits Aggression in Early and Late SI Mice. Administration of PEA (5, 10, 15, and 20 mg/kg, i.p.) inhibited aggression both in late [F(4,44)=14.081; p<0.0001] and early SI mice [F(4,98)=12.327; p<0.0001] (FIGS. 13A and 13B). Bonferroni post hoc analysis showed a significant reduction of the number of attacks in the late ($EC_{50}$ dose=6.5 mg/kg) as well as early SI mice ($EC_{50}$ dose=8 mg/kg) at the doses of 10 mg/kg (−81%, p<0.001, n=7 and −57%, p<0.01, n=15, respectively), 15 mg/kg (−84%, p<0.001, n=7 and −75%, p<0.001, n=13, respectively) and 20 mg/kg (−91%, p<0.001, n=7 and −86%, p<0.001, n=17, respectively). Furthermore, our findings suggest no statistical differences in the effect of PEA among early and late adolescent SI mice.

Figure 14A:
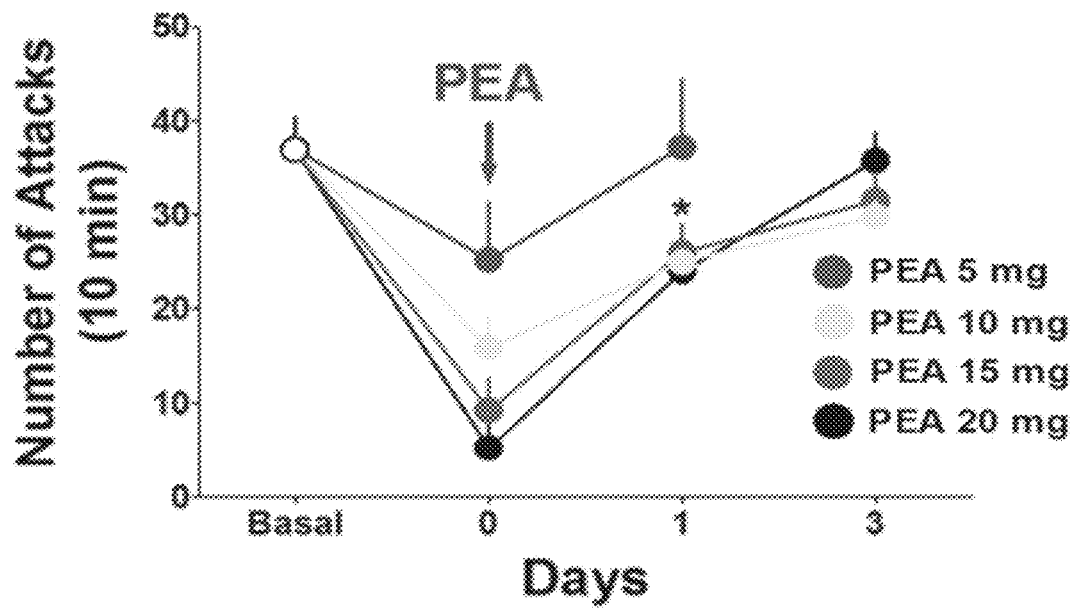
FIGS. 14A-14B show graphs that can demonstrate Drug-induced time-dependent anti-aggressive effect in late and early adolescent SI mice. Aggressive behavior was reinstated after 3 days following a single dose administration with PEA in early SI mice (FIG. 14A) at the doses of 10, 15, and 20 mg/kg, as well as in late SI mice (J) at the doses of 10 and 15 mg/kg. The effect of PEA at the dose of 20 mg/kg was extinguished after 5 days in late SI mice (FIG. 14B). Data represent the mean±SEM of 7-18 mice. *p<0.05; **p<0.01, when compared with basal control levels of aggression.
Figure 14B:
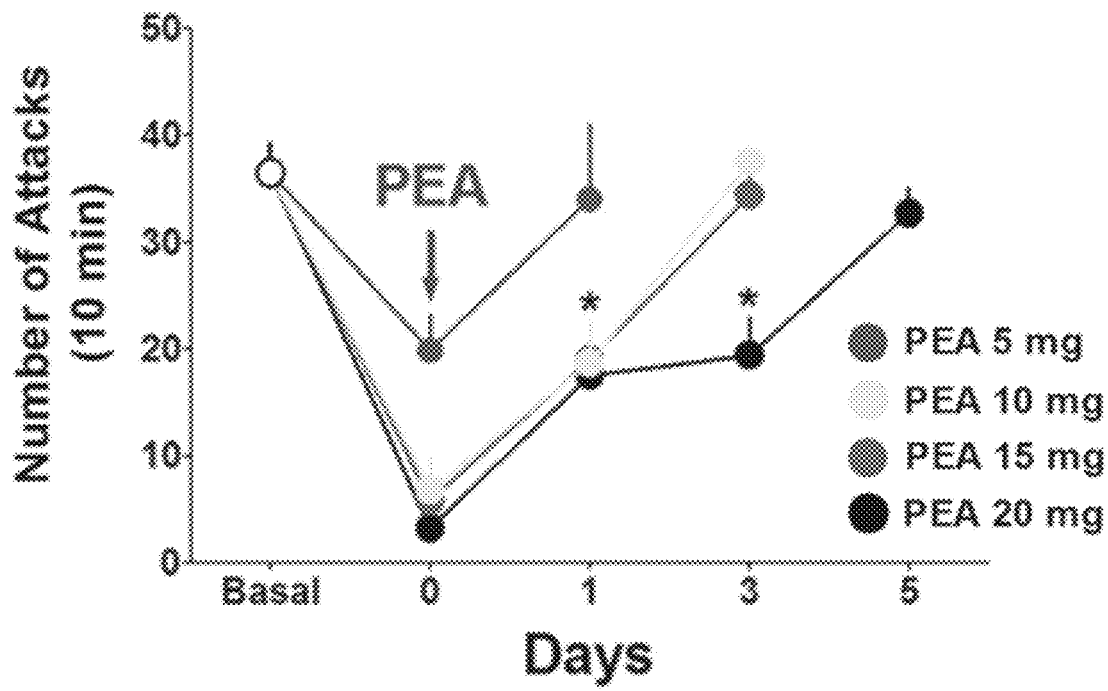
Figure 15A:
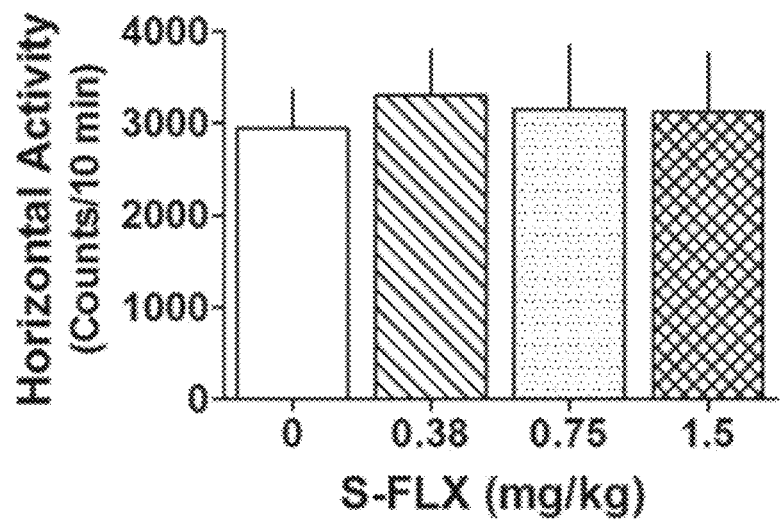
FIG. 15A-15D show graphs that can demonstrate the effect of different drug treatments on locomotor activity both in late and early adolescent SI mice. S-FLX (FIGS. 15A-15B) and PEA (FIG. 15C-15D) were administered to early (left side) and late (right side) adolescent SI mice 60 min before the exposure to the locomotor activity test. All drugs at the dose tested failed to alter locomotion patterns of SI mice. Data represent the mean±SEM of 7-18 mice.
Figure 15B:
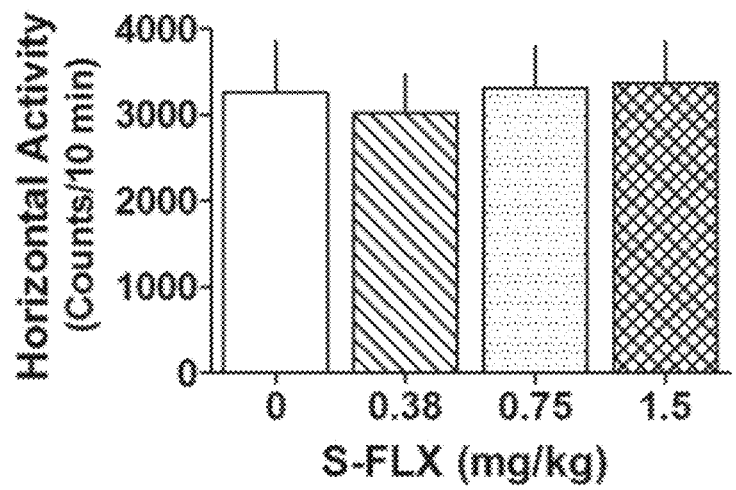
Figure 15C:
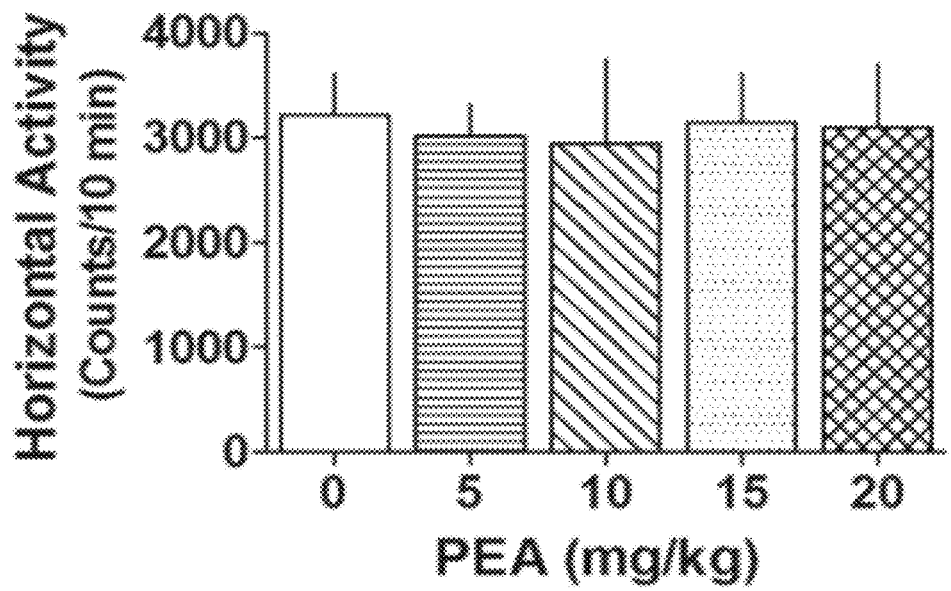
Figure 15D:
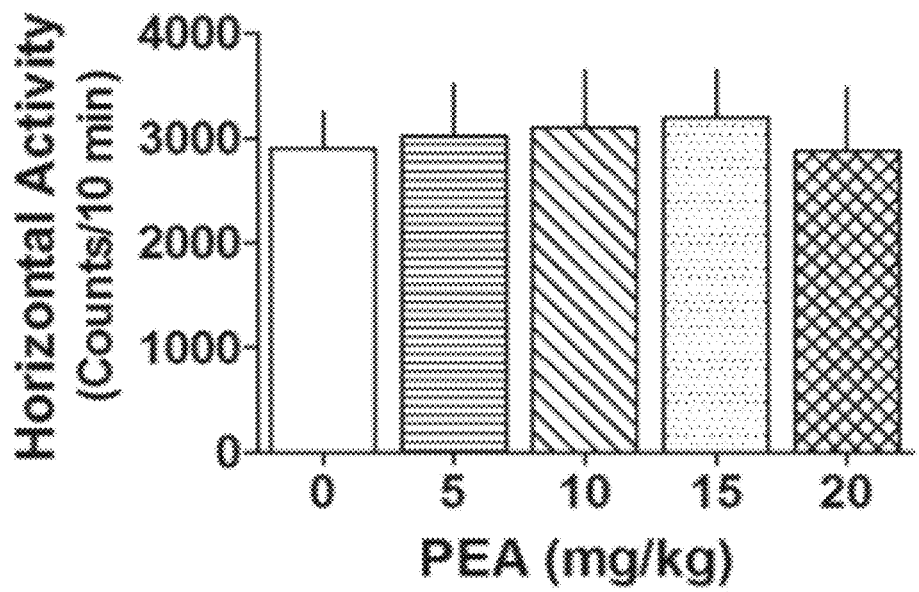

Duration of Drug-Induced Anti-aggressive Effects in Early and Late SI Adolescent Mice. The duration of the anti-aggressive effect for each drug was assessed in a follow-up study after a single dose administration (FIGS. 14A-14B). Aggression rapidly rebounded after 1 day of S-FLX (0.375 mg/kg) administration and after 3 days at the dose of 0.75 mg/kg [PND 21, day 1: t(62)=2.087, p=0.041; PND 45, day 1: t(58)=3.444, p=0.0011] and 1.5 mg/kg [PND 21, day 1: t(63)=3.122, p=0.0027; PND 45, day 1: t(59)=3.59, p=0.0007] both in early and late adolescent SI mice. PEA anti-aggressive effect lasted less than 3 days in late SI adolescent mice at the dose of 10 mg/kg [day 1: t(26)=2.551, p=0.017] and 15 mg/kg [day 1: t(26)=2.309, p=0.0291]. The anti-aggressive effect persisted for 3 days only in late adolescent SI mice after administration of PEA at the dose of 20 mg/kg [day 1: t(26)=2.656, p=0.0133; day 3: t(26)=2.258, p=0.0326]. Even though a similar trend was found in early adolescent SI mice, a significant effect was observed only at the dose of 20 mg/kg [day 1: t(60)=2.044, p=0.0453].

Drug Non-response Rate in Early and Late SI Mice. The rate of SI mice that did not respond to the drugs' pharmacological action was assessed by a decrease of aggression of less than or equal to 30%. Generally, a higher rate of non-response was assessed in early vs. late SI mice (see Table 2, for details). The percentage of non-responders to S-FLX at the higher dose of 1.5 mg/kg was 11.64 and 22.22% in late and early SI mice, respectively. All early SI mice responded to PEA at the doses of 15 and 20 mg/kg; in addition, all late SI mice showed an inhibition of aggression at the PEA doses of 10, 15, and 20 mg/kg.

TABLE 2

Rate of adolescent SI mice that show resistance to the single administration of S-fluoxetine (S-FLX) and PEA

| Drug Treatment | "Non-responders" Late SI mice (%) | "Non-responders" Late SI mice (n) | "Non-responders" Early SI mice (%) | "Non-responders" Early SI mice (n) |
|---|---|---|---|---|
| S-FLX 0.375 mg | 64.3 | 9/14 | 64.3 | 9/14 |
| S-FLX 0.75 mg | 23.1 | 3/13 | 53.3 | 8/15 |
| S-FLX 1.5 mg | 11.8 | 2/17 | 22.2 | 4/18 |
| PEA 5 mg | 42.9 | 3/7 | 53.9 | 7/13 |
| PEA 10 mg | 0 | 0/7 | 26.7 | 4/15 |
| PEA 15 mg | 0 | 0/7 | 0 | 0/13 |
| PEA 20 mg | 0 | 0/7 | 0 | 0/17 |

Effects of Different Drug Treatments on Locomotor Activity in Early and Late SI Mice. A summary of the locomotor activity after all drug tested is shown in FIGS. 15A-15D. S-FLX did not reduce exploratory activity in late and early SI mice at all doses tested. Similarly, exploratory activity was not altered by a single dose treatment with PEA at all doses tested.

Discussion

This Example focused on the aggression expressed by SI mice because it is easy to reproduce, reliable to measure, and fails to decrease after multiple tests (Pinna et al., 2003, 2004; Matsumoto et al., 2005; Nelson and Pinna, 2011). Basal levels of aggression were determined in three resident-intruder tests before performing each of the drug-treated aggression experiment during which, aggression levels for each mouse were monitored before, during and after drug treatment. The effects induced by different classes of drugs, e.g., SSRIs at steroidogenic doses that act as SBSSs, and endocannabinoids that induce neurosteroidogenesis were compared, on the aggression of mice socially isolated in early (PND 21) and late (PND 45) adolescence. These data can demonstrate that: (1) social isolation in early adolescence results in faster development of and a more persistent aggression than isolation in late adolescence (FIG. 11); (2) early isolation was associated with a higher treatment resistance rate Table 2); and (3) a lower duration of the drugs' antiaggressive effects (FIGS. 14A-14B). A single dose of the endocannabinoid, PEA (FIGS. 13A and 13B) induced a dose-dependent robust anti-aggressive effect.

These effects were compared to S-FLX's potency, duration of effects and non-response rate. PEA appeared to be more efficacious as an anti-aggressive agent than S-FLX in both early and late adolescent isolation. Mice isolated at PND21 developed a more severe and persistent aggressive behavior when compared to those isolated at PND45; second, this effect is associated with a higher "non-response" rate toward the drugs tested and a weaker response to S-FLX; third, there was a reduced temporal improvement of behavior following a drug's single dose administration.

One of the best characterized behavioral dysfunctions following protracted social isolation in rodents is the development of aggressive behavior (Valzelli, 1969; Pinna et al., 2003). In SI mice, aggression co-occurs with other emotional behavioral deficits, including enhanced contextual fear and impaired fear extinction, and anxiety-like behavior, which are associated with reduced corticolimbic Allo levels and subsequent GABAergic neurotransmission dysfunction (Dong et al., 2001; Pinna et al., 2003, 2006b; Serra et al., 2006; Matsumoto et al., 2007; Zhang et al., 2014). Remarkably, patients with MDD and PTSD also show a CSF and brain Allo level down-regulation which is correlated with the severity of symptoms (Romeo et al., 1998; van Broekhoven and Verkes, 2003; Uzunova et al., 1998, 2006; Agis-Balboa et al., 2014). These findings suggest that the SI mouse may offer a suitable model to assess the effect of compounds and/or drugs to treat endophenotypic expressions of behavioral deficits that translate into symptoms of psychiatric disorders, including MDD and PTSD. Reduced corticolimbic Allo levels can be upregulated in humans by treatment with SSRIs that also correlates with improved symptoms (Romeo et al., 1998; Uzunova et al., 2006; Agis-Balboa et al., 2014). Further, patients who fail to show behavioral improvements also fail to show CSF Allo level upregulation (Uzunova et al., 1998, 2006). In SI mice, a single low dose of S-FLX, which is devoid of serotoninergic effects, by acting as a SBSSs, e.g., selectively stimulating brain Allo biosynthesis, is associated with reduced aggression and improvement of other emotional behaviors (Pinna et al., 2003, 2009; Pibiri et al., 2008; Nin et al., 2011a). The endocannabinoid PEA (at about 15-20 mg/kg) was the only drug studied that improved aggressive behavior in all of the early adolescent SI mice. These results can evidence the benefit of endocannabinoids can be anti-aggressive agents and can provide benefits in treating neuropsychiatric disorders characterized by impulsive aggression, including but not limited to, PTSD.

Clinical findings show that only 50% of depressed patients respond to first-line therapy antidepressants, while more than one third of responders develop resistance to antidepressants (Kemp et al., 2008). It is generally accepted that early traumatic experiences cause a poor response to SSRI treatments later in adulthood, representing one of main causes for pharmacoresistance. For example, abuse in general but—most notably—abuse occurring at 7 years of age or younger predicted a lower response to 8 weeks of SSRI antidepressants (Williams et al., 2016). Likewise results from this Example show that behavioral deficits are more difficult to improve or modulate in mice subjected to early social isolation than mice who are socially isolated later in adolescence using the same drug doses. Furthermore, these preclinical findings together with clinical observations of high incidence of resistance to current prescribed SSRI medication at supposedly steroidogenic doses can suggest that the deficits in the activity of enzymes that are involved in Allo biosynthesis may not be fully counteracted by SSRIs in a portion of depressed and PTSD patients.

The endocannabinoid system can be involved in stimulating neurosteroidogenesis. Direct activation of cannabinoid receptor type 1 (CB1) by 19-tetrahydrocannabinol (THC), the principal psychotropic compound of *Cannabis sativa*, increased by 30-fold the synthesis of pregnenolone, the precursor of Allo (Vallée et al., 2014; Vallée, 2016). More evidence suggests that the endocannabinoid and neurosteroid systems are interrelated. PEA can induce Allo biosynthesis in cultured astrocytes and spinal cord and it can regulate pentobarbital induced sedation by acting at the intracellular peroxisome proliferator-activated receptor (PPAR)-α (Sasso et al., 2012). Moreover, PEA was observed to induce antidepressant effects similar to those of fluoxetine (Yu et al., 2011). As can be demonstrated by Example 1 herein, PEA can induce Allo biosynthesis in corticolimbic areas and this enhancement of neurosteroid levels is involved in the improvement of behavioral dysfunctions of SI mice (Locci and Pinna, 2017b). Therefore, drugs capable of inducing neurosteroidogenesis by targeting the endocannabinoid system could represent another important therapeutic alternative to treat depression, PTSD and anxiety disorders in SSRI non-responders.

REFERENCES FOR EXAMPLE 2

Agid, O., et al. (1999). Mol. Psychiatry 4, 163-172.
Agis-Balboa, R. C., et. al. (2014). Psychopharmacology 231, 3569-3580.
Berton, O., and Nestler, E. J. (2006). Nat. Rev. Neurosci. 7, 137-151.
Bremner, J. D., et al. (2000). Am. J. Psychiatry 157, 1120-1126.
Choudary, P. V., et al. (2005). Proc. Natl. Acad. Sci. U.S.A. 102, 15653-15658.
Dong, E., et al. (2001). Proc. Natl. Acad. Sci. U.S.A. 98, 2849-2854.
Dube, S. R., et al. (2001). JAMA 286, 3089-3096.
El-Hage, W., et al. (2013). Front. Pharmacol. 4:146.
Famularo, R., et al. (1992). J. Am. Acad. Child Adolesc. Psychiatry 31, 863-867.
Fatemi, S. H., et al. (2013). Transl. Psychiatry 3:e303.
Felitti, V. J., et al. (1998). Am. J. Prey. Med. 14, 245-258.
Geuze, E., et al. (2008). RMol. Psychiatry 13, 74-83.doi: 10.1038/sj.mp.4002054
Golden, R. N., et al. (2002). J. Clin. Psychiatry 63, 577-584.
Heim, C., and Nemeroff, C. B. (2001). Biol. Psychiatry 49, 1023-1039.
Ipser, J. C., and Stein, D. J. (2012). Int. J. Neuropsychopharmacol. 15, 825-840.
Kemp, A. H., et al. (2008). CNS Spectr. 13, 1066-1086.
Kendler, K. S., Kuhn, J. W., and Prescott, C. A. (2004). Psychol. Med. 34, 1475-1482.
Kessler, R. C. (1997). Annu. Rev. Psychol. 48, 191-214.
Kessler, R. C., et al. (2005). Arch. Gen. Psychiatry 62, 593-602.
Klempan, T. A., et al. (2009). Mol. Psychiatry 14, 175-189.
Lanquillon, S., et al. (2000). Neuropsychopharmacology 22, 370-379.
Locci, A., and Pinna, G. (2017a). Br. J. Pharmacol.
Locci, A., and Pinna, G. (2017b). Neurosci. Abstr. 2017: 13420.
Luscher, B., Shen, Q., and Sahir, N. (2011). Mol. Psychiatry 16, 383-406.
Matsumoto, K., et al. (2005). Stress 8, 85-93.
Matsumoto, K., (2007). Stress 10, 3-12.
McCauley, J., et al. (1997). JAMA 277, 1362-1368.
Merali, Z., et al. (2004). J. Neurosci. 24, 1478-1485.
Nanni, V., Uher, R., and Danese, A. (2012). Am. J. Psychiatry 169, 141-151.
Nelson, M., and Pinna, G. (2011). SNeuropharmacology 60, 1154-1159.
Nemeroff, C. B. (2008). Neuron 59, 185-186.
Nin, M. S., et al. (2011a). Front. Endocrinol. 2:73.
Nin, M. S., et al. (2011b). Trab. Inst. Cajal 83, 215-216.
Pibiri, F., et al. (2008). Proc. Natl. Acad. Sci. U.S.A. 105, 5567-5572.
Pinna, G., et al. (2004). Proc. Natl. Acad. Sci. U.S.A. 101, 6222-6225.
Pinna, G., et al. (2005). Proc. Natl. Acad. Sci. U.S.A. 102, 2135-2140.
Pinna, G., et al. (2006a). Proc. Natl. Acad. Sci. U.S.A. 103, 4275-4280.
Pinna, G., Costa, E., and Guidotti, A. (2006b). Psychopharmacology 186, 362-372.
Pinna, G., Costa, E., and Guidotti, A. (2009). Curr. Opin. Pharmacol. 9, 24-30.
Pinna, G., et al. (2003). Proc. Natl. Acad. Sci. U.S.A. 100, 2035-2040.
Pinna, G., et al. (1997). Proc. Natl. Acad. Sci. U.S.A. 94, 2719-2723.
Pinna, G., and Rasmusson, A. M. (2014). Front. Cell. Neurosci. 8:256.
Prigerson, H. G., et al. (2001). J. Nerv. Ment. Dis. 189, 99-108.
Rasmusson, A. et al. (2017). Neurosci. Lett. 649, 156-163.
Romeo, E., et al. (1998). Am. J. Psychiatry 155, 910-913.
Rush, A. J., et al. (2006). Biol. Psychiatry 59, 493-501.
Sasso, O., et al. (2012). Pain 153, 33-41.
Sequeira, A., et al. (2009). PLoS ONE 4:e6585.
Serra, M., et al. (2006). J. Neurochem. 98, 122-133.
Shamseddeen, W., et al. (2011). J. Am. Acad. Child Adolesc. Psychiatry 50, 293-301.
Tallarida, R. J., and Murray, R. B. (1987). Manual of Pharmacologic Calculations with Computer Programs, 2nd Edn. New York, N.Y.: Springer.
Uzunova, V., et al. (2006). Psychopharmacology 186, 351-361.

Uzunova, V., Sheline, Y., Davis, J. M., Rasmusson, A., Uzunov, D. P., Costa, E. et al. (1998). Proc. Natl. Acad. Sci. U.S.A. 95, 3239-3244.
Vallée, M. (2016). Mol. Biol. 160, 78-87.
Vallée, M., et al. (2014). Science 343, 94-98.
Valzelli, L. (1969). "Aggressive behavior induced by isolation," in Aggressive Behavior, eds S. Garattini and S. B. Sigg (Amsterdam: Excerpta Medica Foundation), 70-76.
van Broekhoven, F., and Verkes, R. J. (2003). Psychopharmacology 165, 97-110.-1
Walderhaug, E., et al. (2010). Pharmacopsychiatry 43, 45-49.
Westenberg, H. G. (1996). J. Affect Disord. 40, 85-93.
Whiteford, H. A., et al. (2013). Lancet 382, 1575-1586.
Wiersma, J. E., et al. (2009). J. Clin. Psychiatry 70, 983-989.
Williams, L. M., et al. (2016). Transl. Psychiatry 6:e799.
Willner, P., et al. (2013). Neurosci. Biobehav. Rev. 37(10 Pt 1), 2331-2371.
Yu, H. L., et al. (2011). Pharmacol. Rep. 63, 834-839.
Zhang, L. M., et al. (2014). Int. J. Neuropsychopharmacol. 17, 1659-1669.
Zlotnick, C., et al. (1997). J. Consult. Clin. Psychol. 65, 333-336.

Example 3

Introduction.

Figure 16:
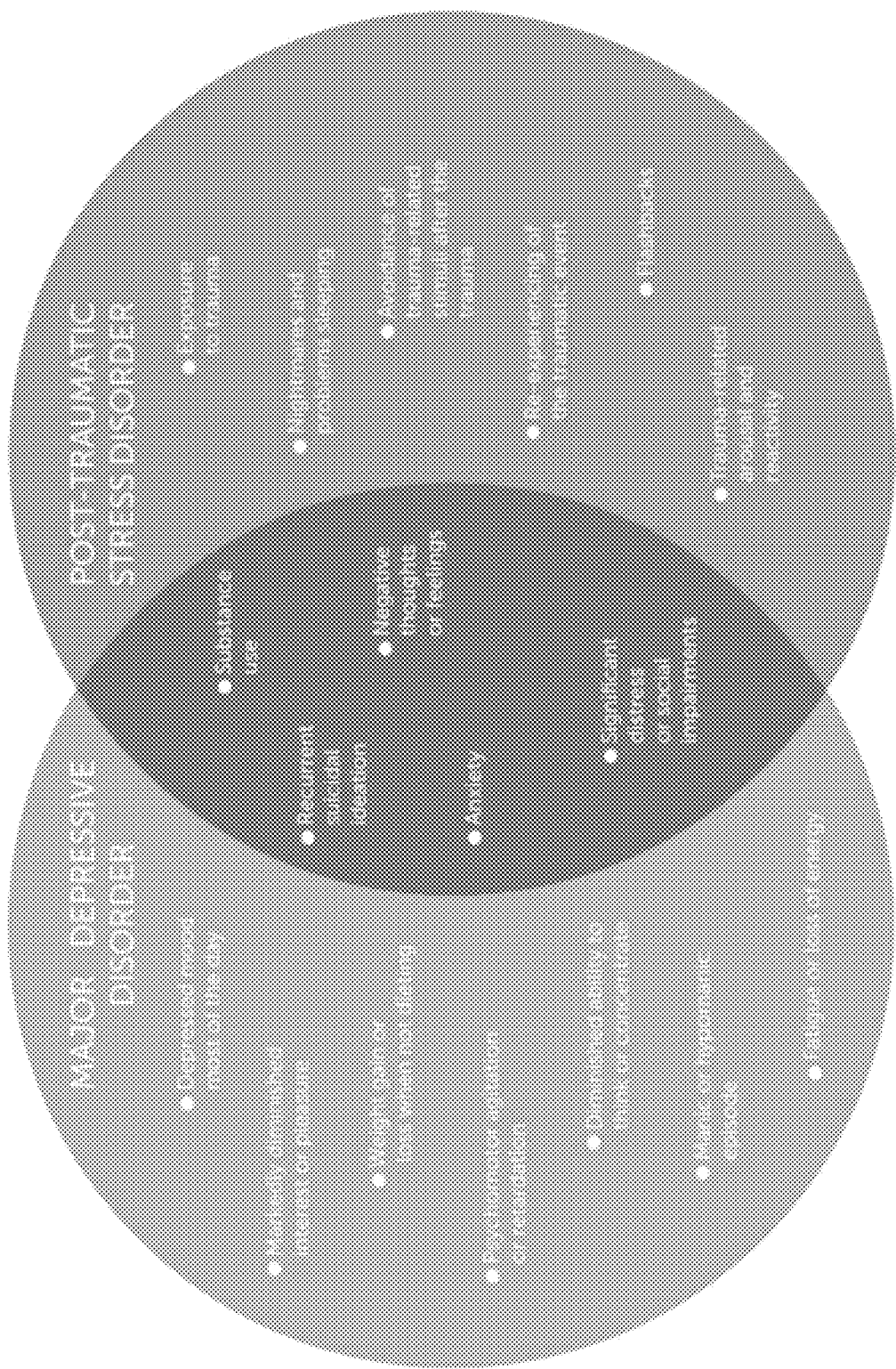
FIG. 16 shows a schematic that can demonstrate symptoms of MDD and PTSD as described by DSM-5. The DSM-5 describes the criteria to diagnose psychiatric disorders such as MDD and PTSD. The left blue circle lists the core symptoms of MDD, while, the right circle lists the core symptoms of PTSD. The intersection represents the shared symptoms of these two disorders.

The ability to cope with stress and negative life experience is an essential survival function not only in humans, but in all living organisms. Environmental factors play a role in the development of behavioral alterations. The ability to adapt to changed environmental conditions or the lack thereof, could play a key role in the onset of mood disorders. While adversities are very frequent during the lifetime of an individual, ranging from 50% to 84% in the general population [1, 2], the majority of people are resilient to adverse life events [3] but still, a large portion (about 10%) fails to develop resilience, and instead develop mood disorders such as major depressive disorder (MDD) and/or post-traumatic stress disorder (PTSD) [4]. MDD and PTSD have been dramatically increasing in the past decade [5]. Depression is a profound multifaceted neurobiological disorder of mood and emotions, which is often the result of different psychological stressors. It has a prevalence of 8-12% [6], and is the cause of impairment in different neuropsychological functions, like attention, learning and memory [7]. The DSM-5 describes a multitude of symptoms for MDD, including sadness, anhedonia, disturbed concentration, significant changes in body weight (loss or gain), that highlight the complexity of this neuropsychopathology [8]. PTSD is a stress-induced psychiatric disorder that emerges in individuals after the exposure to a trauma and is characterized by an altered ability to cope with stress. The core symptoms of this psychiatric disorder are re-experiencing symptoms, nightmares about the trauma, changes in arousal and reactivity, avoidance of trauma-related reminders and alterations of mood [8]. PTSD and MDD share numerous overlapping symptoms and comorbidity and often MDD symptoms in PTSD patients are a progression of the disorder [9]. Both PTSD and MDD are characterized by high incidence of suicidality with a prevalence of 9.5% of patients with MDD that attempted suicide over an 18 month period [10]. Predictors for suicide in MDD patients are the male gender, family history of psychiatric disorders, more serious depressive symptoms and comorbidity with other disorders, such as anxiety spectrum disorders and substance use disorder (SUD) [11]. The core and overlapping symptoms of MDD and PTSD are presented in FIG. 16.

Moreover, both of these pathologies show a gender-related dimorphism with females more affected than males [12, 13]. In both PTSD and MDD, the prevalence in women is more than double that observed in males [14] pointing to a role of sexual hormones in the development and maintenance of the disorder. While, imbalance in sexual hormones synthesis could play an important role, they cannot explain the basic psychobiological mechanisms. Recently, it has become clearer that the convergence of multiple factors, such as biological aspects and socio-psychological environmental conditions, play a role in MDD and PTSD [15, 16, 17, 18]. Likewise, a multiplicity of factors, including genetic vulnerability, immunological alterations, epigenetic mechanisms, neurohormones, neurotransmitter systems, neuropeptides and endocannabinoids and their receptors, seem to play a role both in the manifestation and the maintenance of mood disorders.

Despite advances in the neurobiological and pathophysiological aspects, the current diagnosis for MDD and PTSD is based on patients' self-reported interviews and on the clinician's observation. These methods to diagnose psychiatric disorders is quite subjective and far from optimal because of the consistent heterogeneity not only of the symptoms, but also of the etiology [19]. Furthermore, patients with mood disorders frequently are not able to adequately characterize the symptoms of the pathology [20] and the scoring systems are often discordant [21]. Thus, it becomes urgent to develop objective biological diagnostic tools based on neurobiological deficits to obtain early diagnosis, monitor individuals at risk, instruct individualized treatments, follow-up on treatment success and possibly prevent future relapse [22, 23]. This may bring a disruption in the diagnosis of psychiatric disorders as we know of, based on symptoms characterized by the DSM-5 to regroup disorders based on their neurobiological characteristics. The progress in the diagnosis and treatment of psychiatric disorders based on biomarker assessment, rather than by symptoms classification, is long needed. Contrary to other neuroscience fields, such as the neurodegenerative disorders, progress in the assessment of valid biomarkers has been rather slow [24].

This Example discusses several biomarkers in PTSD and MDD. Tests can provide a useful tool for treatment and patient selection and to monitor treatment outcomes; ensuring patients receive the most appropriate and efficient treatment for a better chance to promptly recover.

Mood disorders and Biomarkers. The identification of biomarkers in clinical psychiatry can give a measurable indicator of the neurobiological condition of an individual independent of a DSM-5-based diagnosis, of its predisposition to develop psychiatric disorders or the current presence of a behavioral dysfunction. A genetic predisposition for PTSD or MDD has been shown in familial or twin studies [25], which highlights the role of genetic polymorphisms in some psychiatric disorders. In particular, some polymorphisms of the dopaminergic and serotoninergic circuits have been found. A polymorphism for the dopamine D2 receptor seems to contribute to PTSD predisposition [26], while, the serotonin transport gene is linked with more depressive symptoms and suicidal ideations [27]. Furthermore, a functional polymorphism of the BDNF gene has been associated with deficient hippocampal cognitive function [28], and a polymorphism in 5α-reductase type 2 informed susceptibility for PTSD or depressive symptoms during pregnancy [29].

Figure 17:
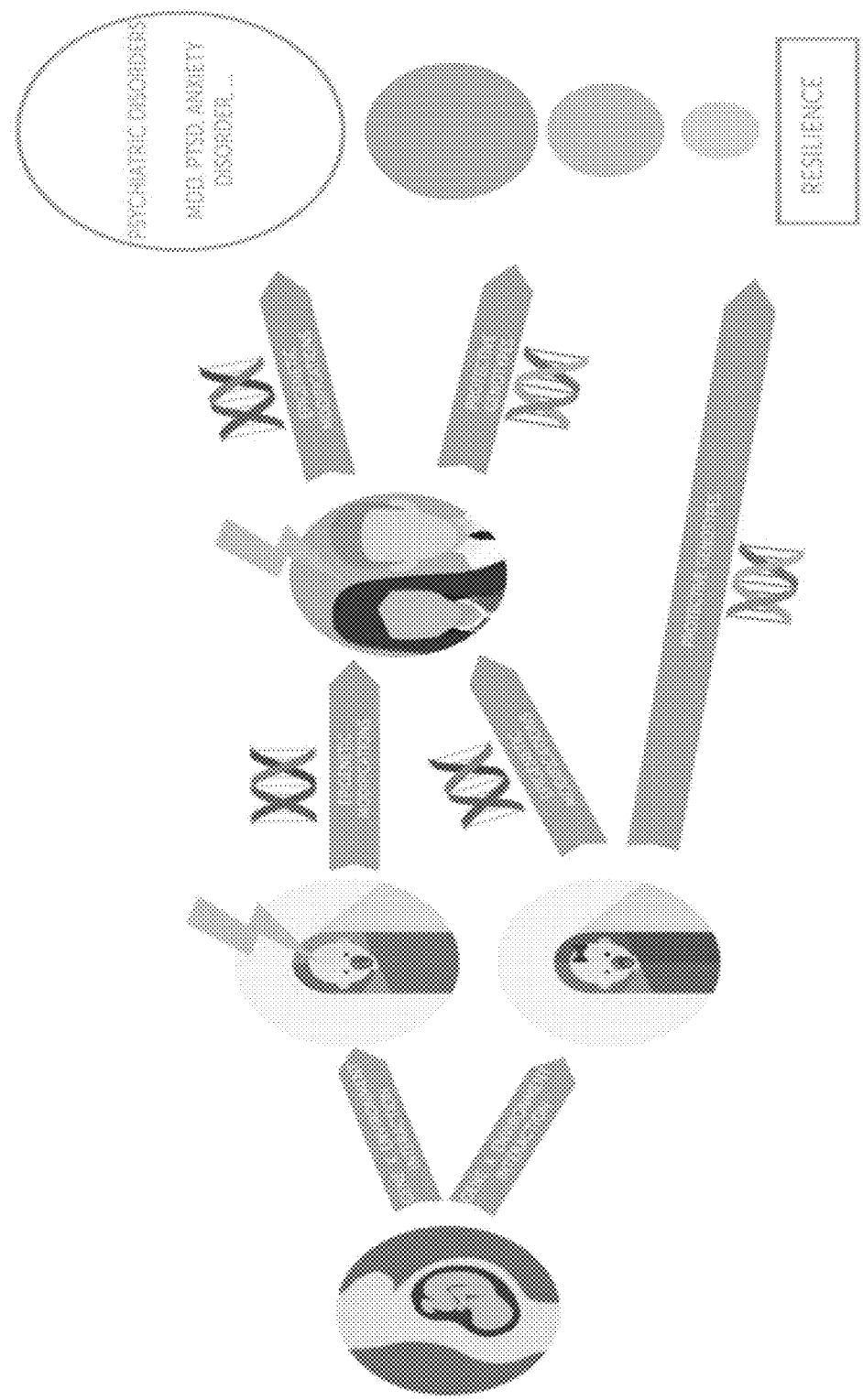
FIG. 17 shows a representation of genomic and epigenetic roles in the development of neuropsychiatric disorders. The early life experiences, particularly early life adversities, may lead to epigenetic alterations. In absence of traumas and stressful conditions there is an increased possibility of developing resilience in adult life. The exposure to early life adversities in childhood may result in a phenotype that is more susceptible to psychiatric disorders following a more recent exposure to a stressor. Nevertheless, even trauma-exposed adults who have not experienced adversities during early life may develop PTSD or MDD.

In PTSD and MDD, exposure to a trauma can epigenetically impact neuronal function and affect the physiological and the behavioral mechanisms of stress adaptation [30]. Understanding the genetic vulnerability of factors that contribute to psychiatric illness may enable identification of individuals which fail to cope with traumatic events. For instance, the exposure to early-life traumas is very frequent in the psychiatric patients' history [31, 32]. During childhood, the programming of the neurobiological system and the most relevant epigenetic alterations take place [33]. Thus, an early adverse experience, like child abuse and neglect, dramatically enhance an individual predisposition to develop depression or other psychiatric disorders later in life. Trauma clearly induces epigenetic changes with short- and long-term effects on neuronal function, brain plasticity and behavioral modifications [30, 34, 35]. Epigenetic alterations can be reversible and are potential biomarker candidates for the development of new treatments for psychiatric disorders, as demonstrated by studies in rodents [36] (depicted in FIG. 17).

One of the principal neuronal deficits, which was firstly pointed as a primary deficit in depression was the serotoninergic neurotransmission although this hypothesis has never found to be convincing scientific evidence [37]. A fundamental evidence for the original hypothesis of serotonin's role in depression is derived from the mechanism of tricyclic antidepressant (TCA) on the reuptake of serotonin. This gave rise to develop a number of antidepressants, such as the selective serotonin reuptake inhibitors (SSRIs), which can enhance the activity of serotonin in depressed patients' brain, improving their depressive symptoms [38, 39]. However, SSRIs only help 50% of MDD and PTSD patients [40] and this result highlights that more and better biomarkers need to be discovered. Given PTSD and MDD are multifactorial disorders, it is important to assess a number of other biomarkers and treatment targets so that patients can be classified based on their specific biochemical deficits. Furthermore, this could lead to stratification in patients' population that allows the design of better clinical trials and, later, the design of better treatments. Therefore, if a patient has a deficit in a specific neuroactive steroid level, the possible therapy will supplement that neuroactive steroid or its surrogate but will not provide a serotonergic molecule that may not help and may only result in unwanted side effects.

In the previous years, biomarker discovery for MDD and PTSD has suggested a number of neurochemical deficits in preclinical and clinical settings, including HPA alterations in response to stress, variations of immune response or signaling and dysregulation of the endocannabinoid and neurosteroid systems, which will be examined in further details herein.

Biomarkers in PTSD and MDD.

Chronic Stress and HPA Axis Role. Aside from a genetic vulnerability, one of the major causes of depression is exposure to chronic stress. Prolonged stress leads to alteration of behavior and physiology of both humans and rodent models of depression [41, 42]. The stress response is mediated by the hypothalamus-pituitary-adrenal (HPA) axis; the role of this axis in MDD and PTSD has been demonstrated [43]. Alterations of the corticotropin-releasing hormone (CRH) function have been reported and enhanced levels of CRH have been found in the cerebrospinal fluid (CSF) of depressed patients [44]. The increased release of CRH results in a greater secretion of adrenocorticotropic hormone (ACTH) and in increased glucocorticoids synthesis, in particular cortisol, which has an inhibitory feedback on CRH and ACTH through the glucocorticoid receptor (GR) and the mineralocorticoid receptor (MR). Of note, patients with MDD and PTSD show enhanced levels of cortisol in saliva, plasma and urine, and an increased size and activity of pituitary and adrenal glands [45]. The receptor subtype for CRH, CRHR1, seems to have important effects on anxiety and depression, even if the results are somewhat inconclusive [46]. Papiol and colleagues found a SNP in the CRHR1 gene, rs 110402, and showed that homozygous patients for TT in this SNP present an earlier onset of the disease than other patients [47].

Several studies investigated the possible alteration of the HPA axis by stimulating the GR by the administration of the synthetic glucocorticoid, dexamethasone (dex). They demonstrated that depressed patients fail to show a negative feedback induced by an oral dose of dex; while, in healthy individual, a low dose of dex leads to an inhibition of the HPA axis and to decreased cortisol levels for up to 24 hours [48, 49, 50, 51]. Nevertheless, the glucocorticoid system is a potential target for MDD and PTSD therapeutics. For example, GR sensitivity is regulated by FKA binding protein 51 (FKBP5) and depressed patients exhibit decreased GR sensitivity with a substantial reduction of FKBP5 mRNA expression. The FKBP5 gene transcription is dependent on GR activation with a feedback modulation that regulates GR sensitivity. After an administration of dex, depressed patients showed a GR-mediated alteration in gene expression compared with healthy controls [52]. However, the FKBP5 gene appears to play a primary role in psychiatric pathologies. For example, polymorphisms associated with early traumatic events, like childhood abuse, predict adult major depression and PTSD [53]. A study of Binder and colleagues revealed that 3 polymorphisms of this gene are significantly associated with an enhanced FKBP5 expression, which regulates the HPA axis functionality. Patients with these polymorphisms show less hyperactivity of the axis during depression and, specifically rs1360780 was strongly associated with antidepressant effects in patients with a slower response in homozygotes [54].

The interaction between early traumas and polymorphisms determines the methylation state of the gene and regulates the sensitivity of FKBP5 to GR regulation [55]. Remarkably, the severity of PTSD is associated with the level of FKBP5 gene expression; low expression of this gene is linked to low plasma cortisol [56]. Of note, adversities during childhood influence the transcriptional activity and the state of the HPA axis genes implicated in the response to stress. Moreover, the onset of PTSD after trauma exposure is associated with pre-traumatic biomarkers, which reveal the level of sensitivity to stress [57].

Two possible stable epigenetic biomarkers for PTSD: GR and the FKBP5 gene methylation were observed. The different methylation of these genes is associated, respectively, with prognosis and with symptom severity. The GR exon 1F promoter methylation predicted the outcome of the treatment, while, the cytosine methylation of FKBP5 promoter seemed to be associated with recovery [58]. GR gene methylation does not change over time signifying that early environmental experiences cause a durable epigenetic modification of this gene [59]. In animal studies, it is clear that variations in maternal care leads to a different methylation pattern of GR gene with lasting effects on GR responsiveness in adults [60]. In humans, child abuse is linked to enhanced methylation of GR exon 1F promoter in leukocytes and in the hippocampus obtained post-mortem [61]. Thus, the GR promoter methylation in hippocampus seems to be affected by maternal care, which may alter the inhibiting feedback regulation of glucocorticoids on CRF expression and on HPA axis ability to cope with stressors [62].

The early-life experiences have a strong impact on gene expression and adversity during the early phase can influence both GR and FKBP5 methylation. In PTSD, the GR promoter methylation induces an enhanced GR sensitivity with low levels of glucocorticoids, which decrease FKBP5 gene expression. This diminished FKBP5 gene expression could sustain the increased sensitivity of GR. Thus, the methylation of the FKBP5 promoter leads to an increase of this gene expression and, consequently, to a reduced GR sensitivity. Coincidently, patients who respond to treatment show a decrease methylation of the FKBP5 promoter and of GR sensitivity.

Methylation or demethylation of a number of other genes and their expression patterns are due to glucocorticoids effects. This includes genes linked to the synthesis of the brain-derived neurotrophic factor (BDNF), which affects neurogenesis, of neuropeptides, such as neuropeptide Y and α-MSH, or of enzymes involved in biosynthesis of neurohormones, such as the GABAergic neuroactive steroids [63, 64, 65].

The Immune System Modulation of Stress Response. The HPA axis and the immune systems are interconnected; however, it is poorly understood or research how they regulate each other in PTSD and MDD. Some pre-clinical research highlights the role of immune factors, such as pro-inflammatory cytokines (interleukin IL-6, IL-1 and TNF-α) in the regulation of memory and neurogenesis, and their interaction with glutamate and GABA signaling or changes in long term potentiation (LTP) [66, 67].

The most promising inflammatory biomarkers in serum of subjects with psychiatric disorders are pentraxin C-reactive protein (CRP), tumor necrosis factor alpha (TNF-α), and IL-1 and IL-6 [68]. CRP, an acute-phase protein produced by the liver, is found in plasma in response to inflammation, and could be an important biomarker for psychiatric disorders, in addition to participating in inflammatory processes [69]. An increased CRP level was shown in patients with PTSD or in suicidal patients [70, 71]. Some recent studies showed that patients with CRP levels above 10 mg/l responded better to treatment with TCAs or SSRIs than to psychotherapy [72] and that patient with low CRP levels (<1 mg/l) showed more consistent treatment response to escitalopram than to nortriptyline [73]. Taken together, these findings suggest that CRP may be an intriguing predictor of treatment outcomes that could lead to a personalized treatment approach.

In depressed patients, an increased level of plasma CRP and IL-6 [74], and the serum or plasma levels of IL-1β and IL-6 are often related to antidepressant treatment, given that their levels inversely correlated with treatment response [75].

The investigation of mRNA levels of cytokines in MDD patients showed an increase of several inflammatory factors, such as IL-1β, IL-6 and TNF-α. Furthermore, two SNPs of IL-1β gene, rs16944 and rs1143643, were strongly associated with decreased responsiveness to antidepressants and the fMRI-analysis showed reduced amygdala hyperactivity to emotional stimuli [76]. A SNP was also discovered for the IL-6 gene, rs1800795, which is associated with enhanced levels of plasma IL-6. Furthermore, its interaction with additional stressors increases the risk of MDD development [77, 78].

A study by Sukoff Rizzo and colleagues, in rodents, demonstrated that an increased IL-6 level in the brain results in development of depressive-like behavior and the activation of IL-6, inhibits the antidepressant effect of SSRIs [79]. This finding may explain why some antidepressants fail to induce beneficial pharmacological effects in patients with MDD and PTSD.

Another cytokine that is increased in the plasma of depressed patients is TNF-α, and failure to normalize its levels also correlated with failed response to SSRIs [80, 81]. In particular, recent studies suggested that responders to antidepressants showed a lower expression of TNF-α. Lower expression of this cytokine (30%) was observed after successful treatment with escitalopram [82]. These findings collectively suggest that pro-inflammatory markers may be more useful to predict treatment outcomes rather than for diagnosis of the pathology. Whether the enhancement of pro-inflammatory markers reflects a neural dysfunction or whether these molecules play a role in the pathogenesis of psychiatric disorders is unclear, however, their alteration may be used as a marker to determine the most appropriate treatment. The complex interconnection between the immune and the neuroendocrine systems allows an appropriate adaptive reaction to a variety of stressors with a logical role in the development of the disorder.

Neuroplasticity. PTSD and MDD are associated with low levels of neurotrophins, like BDNF, which play a fundamental role in neuronal growth, synaptic maturation and plasticity [83]. Hence, BDNF is fundamental for the development of the nervous system and decreased serum levels of this neurotrophin and/or of its receptor, TrkB, may be a useful predictor for dysfunctional behavior and in particular for suicidal ideations [70]. Studies in rodent models show a decreased BDNF mRNA expression in the hippocampus during chronic and acute stress, with a consequent effects on hippocampal neurogenesis [84]. The reduction of BDNF mRNA expression has been associated with increased IL-6 expression [85]. Importantly, both glucocorticoids and pro-inflammatory cytokines have been often linked to a reduction of BDNF levels and to a diminished neurogenesis resulting in dendritic atrophy [86, 87]. The mechanism by which pro-inflammatory cytokines could affect BDNF expression is still unclear. However, animal studies showed that IL-1β down-regulates BDNF expression in rat hippocampus, probably by an indirect mechanism that relates to regulation of glucocorticoids [88].

Depressed patients show a reduction of BDNF mRNA expression, with increased levels that correlated with symptom improvement in antidepressant-responders [89]. A recent meta-analysis investigation has suggested that BDNF is a promising biomarker for MDD patients relevant to predict clinical improvement [90].

Contrary to what is observed in MDD patients, the BDNF levels in the serum of subjects with PTSD are controversial. Some researchers reported that it increases in PTSD and it is even higher after traumatic events [91], while others showed lower levels [92]. Berger and colleagues found that serum BDNF level is a good predictor of the treatment outcome in PTSD: lower serum BDNF is a good marker for an appropriate response to escitalopram in patients. They explained this apparent contradictory result, discussing the role of BDNF in the mesolimbic dopamine pathway, where high levels of this neurotrophin is necessary to maintain, in mice, social avoidance behavior, which is a fundamental symptom of PTSD in humans. So, the inhibition of BDNF activity could have mood-regulatory activity in some animal models, which suggests a biphasic concentration-dependent activity of BDNF [93].

Polymorphisms of the BDNF gene have also been investigated, the rs6265, resulting from a substitution of Val66Met, is frequently linked to a higher risk of developing affective disorders [94, 95]. This SNP influences hippocampal volume and memory and seems to increase the susceptibility to both depression and PTSD [96]. Furthermore, the frequency of Met is two times higher in PTSD patients than in healthy control [97]. Stress and Met-allele seem to interact; a study of healthy European volunteers suggested that this interaction can result in developing depression and anxiety [98].

The NPY implications in Resilience. An important mediator in the regulation of the stress responses is the neuropeptide Y (NPY) [99]. NPY and its receptors play a fundamental role in the response to stressors and a decreased fear, anxiety, and also improve memory processes [100, 101]. NPY participates in the regulation of HPA axis by interacting with the paraventricular nucleus (PVN) of the hypothalamus and with the action of CRH [102]. Stimulation of NPY Y1 receptors in the hippocampus of rodents appears to inhibit the HPA axis, although some studies have reported different results [103, 104, 105]. Evidence demonstrates that NPY is relevant in PTSD and MDD pathophysiology. Clinical studies showed that NPY concentration in the CSF and plasma is reduced in patients with PTSD [106, 107, 108]. In particular, a study by Ramusson et al. showed a lowered level of plasma NPY in PTSD subjects, but NPY level was also reduced in combat-exposed individuals without PTSD, showing that the trauma itself alters NPY concentration [107]. However, later studies observed opposite results, showing both trauma-exposed PTSD patients with no alterations of NPY levels [109] and combatexposed veterans without PTSD with a higher NPY expression [110]. Sah and colleagues showed that combat-exposed veterans with PTSD have lower NPY levels in the CSF in comparison to trauma-exposed veterans without PTSD [108]. Thus, the abnormalities in NPY concentrations are of interest because NPY seems to promote resilience and prevent the development of trauma-induced PTSD. Genetic evidence supports this role of NPY: Individuals with low expression of NPY genotype present exaggerated amygdala reactivity, which reflects an over-reaction to stress [111]. However, direct associations between NPY gene polymorphisms with PTSD have not been observed. Several SNPs of the NPY gene have been studied and the most promising is rs16147 for its role in stress responsiveness. The NPY SNP rs16147 is highly related to the variation of the NPY levels and is associated with a reduction of NPY expression [111]. Thus, NPY could have therapeutic implications, because it is stress-related, linked to trauma exposure, and it could facilitate resilience decreasing the possibility to develop PTSD [112].

The Role of Endocannabinoids and Allopregnanolone in MDD and PTSD.

The biosynthesis of Neuroactive Steroids. Neurosteroids, allopregnanolone (Allo) and its stereoisomer, pregnanolone (PA), are synthesized in glutamatergic corticolimbic neurons, including cortical and hippocampal pyramidal neurons, and pyramidallike neurons of the basolateral amygdala [113, 114]. They rapidly modulate neuronal excitability by acting as potent positive allosteric modulators of the action of GABA at GABAA receptors and they are responsible for the fine-tuning of the receptor for GABAmimetic, agonists and positive allosteric modulators [115, 116, 117, 118]. Recent finding in the field have suggested that the sulfated congeners of these neurosteroids, e.g., PA sulfate, act as inhibitors of tonic rather than phasic NMDA-mediated neurotransmission [119].

Downregulation of neurosteroid biosynthesis, which includes Allo and PA levels and their biosynthetic enzyme 5α-reductase type I and 3α-hydroxisteroid dehydrogenesis (3α-HSD), are strongly associated with major depression and PTSD (for a review please see [120, 121]). Specifically, patients with depression show serum, plasma, CSF, and brain reductions of Allo levels and/or biosynthesis [122, 123, 124, 125]. Likewise, depression and anxiety symptoms in both anorexic and obese females or during pregnancy and postpartum are associated with downregulated Allo levels [126, 127]. The levels of Allo in the CSF are 40-60% decreased in patients with unipolar major depression and premenopausal women with PTSD [124]. The lowest levels were found in the PTSD patients with comorbid depression [128]. Altered Allo levels have been observed both in serum and CSF in several other neuropathologies, including postpartum depression and drug addiction [124,129]. Women with PTSD show lower Allo concentration in the CSF and serum, while progesterone and the immediate Allo precursor, 5α-DHP fail to change, pointing to a possible deficit in the enzyme 3α-HSD [130]. Likewise, in PTSD males, the CSF Allo levels decrease. Without being bound by theory, this may be due to deficits of 5α-reductase type 1, and were negatively correlated with PTSD symptoms [131]. Moreover, a SNP in the 5α-reductase type II gene is linked to enhanced risk for PTSD in men [132]. 5α-reductase type 2 is preferentially expressed in the periphery in the adrenal cortex [133], however, peripheral GABAergic neuroactive steroids, including THDOC are changed during stress and may access and influence corticolimbic circuitry [134]. Thus, the concentration and, in particular, the ratio of Allo with other neuroactive steroids levels and deficits in the enzymatic pathway may unveil sex-related biomarkers for PTSD and MDD as well as therapeutic properties in MDD and PTSD patients. Studies in depressed patients with low Allo concentrations in CSF and plasma showed that after SSRI treatment, increased Allo level correlated with improvement of depressive symptoms [123, 124].

The plasma levels of the GABAA antagonist and neuroactive steroids, dehydroepiandrosterone (DHEA) and its sulfate derivatives, DHEA sulfate (DHEAS) are currently being investigated as potential biomarkers for anxiety, MDD and PTSD. DHEA facilitated excitatory NMDA receptor function and plays a role in the inactivation of cortisol in its metabolite cortisone [135]. The DHEAS concentration and the ratio DHEAS to cortisol seems to predict the severity of symptoms of PTSD and depression in patients [136]. In the CSF of women with PTSD, correlation between the ratio of DHEA to Allo levels and their symptoms was observed [128]. This suggests a role in the balance between excitatory and inhibitory neurotransmission and the severity of the pathology.

In mouse models of depression, induced by protracted social isolation stress, a downregulation of Allo levels in corticolimbic neurons was observed and resulted from a decreased expression of 5α-reductase type I [137]. Furthermore, socially isolated (SI) mice show increased aggression, anxiety-like behavior and exaggerated contextual fear responses [138, 139]. In another model of PTSD, the single prolonged stress (SPS) mouse, downregulated cortical Allo levels was associated with enhanced anxiety-like behavior and enhanced contextual fear responses. Importantly, like in PTSD patients [140], stress in SI mice induces changes in GABAA receptor subunit composition with increased expression of α4 and δ subunits [129] that are: 1) mainly expressed in the extra-synaptic GABAA receptor, 2) show an increased sensitivity for neurosteroids, and, importantly, 3) fail to bind benzodiazepines, and therefore result in inefficacy to respond to their pharmacological action. These findings are strikingly consistent with dysfunctions observed in PTSD patients. PET studies show PTSD patients have decreased benzodiazepine binding sites and lack of response to benzodiazepines [140]. Collectively, PTSD like MDD shows a sex-related downregulation of Allo biosynthesis, however, this and its interface with changes in GABAA receptor subunit expression and lack of response to benzodiazepines points to a biomarker axis (FIG. 18), which may be specific for PTSD (discussed in [120]).

In SI mice, administration of Allo or its analogs (ganaxolone, BR351 and BR297) reduces behavioral dysfunction [120, 141]. Furthermore, SSRIs given at low non-serotonergic doses, act as selective brain steroidogenic stimulants (SBSSs), up-regulate Allo levels and improve fear responses, anxiety-like behavior and aggression in Allo-deficient SI mice [142]. Likewise, the 18 kDa translocator protein (TSPO), which gates the entry of cholesterol from the cytosol into the inner mitochondrial membrane to initiate neurosteroidogenesis, resulted in a useful PTSD therapeutic target [143]. Drugs that act at TSPO stimulate downstream Allo levels in the brain of SPS mice and rescue behavioral dysfunctions [144]. In recent clinical trials, allopregnanolone (brexanolone) efficacy against symptoms of postpartum depression (PPD) was superior to that of placebo [145]. PPD patients who received intravenous infusions of allopregnanolone showed a rapid and long lasting remission of depressive symptoms in 70% of treated vs only 9% of placebotreated patients.

The Endocannabinoid System. The endocannabinoid system (eCBS) is involved in HPA activation and its interaction with glucocorticoids is useful to cope with stress. Furthermore, the endocannabinoids (eCBs) modulate fear memory and other memory processes, like reconsolidation and extinction, which are a core feature of PTSD [146]. In a mouse model of depression, the hippocampal suppression of the eCB signaling leads to depressive-like behavior [147, 148], thus suggesting it may play a role in PTSD and MDD.

The endocannabinoid receptor type 1 (CB1) has received growing attention in mood disorders. A positron emission tomography study showed enhanced expression in individuals with PTSD but not in trauma-exposed healthy controls [149]. Furthermore, this study found diminished peripheral level of the endocannabinoid, anandamide (AEA), which suggest that the enhanced CB1 receptor expression, and probably sensitivity, may be in part due to lower levels of AEA [149]. Likewise, a post-mortem study revealed higher expression of CB1 in depressed suicide victims [150]. However, genetic studies support the hypothesis that impairment in CB1 may increase the risk to develop depression and other psychiatric pathologies. SNPs in the CB1 gene can increase the vulnerability to develop depressive episode after trauma exposure and in patients with mood disorders when the frequency of SNPs increases [151, 152]. Moreover, AEA and the congener, 2-arachidonoylglycerol (2-AG) serum concentration is lower in the plasma of depressed women than in matched control subjects [153]. These endocannabinoids in depressed women are a focus of investigation and several considerations of whether they may be valuable markers are being drawn. Rodent models of PTSD and depression show decreased levels of AEA and 2-AG [154]. Other endocannabinoids that activate the peroxisome proliferator-activated receptor alpha (PPAR-α) such as N-oleoyldopamine (OEA) and N-palmitoylethanolamine (PEA) may be involved in the pathophysiology of PTSD and MDD [155]. PPAR-α activation has been shown to mediate the responses to stressful conditions [156]. In healthy adults, PEA significantly increase in clinical stress tests in connection with an increase of cortisol levels [157]. PEA levels also when healthy subjects experience a short-term depressed mood [158]. On the other hand, PEA in PTSD, MDD, and impulsive aggression are decreased [159]. Of note, PEA adjunctive therapy to citalopram improves depressed symptoms and intense physical activity increases PEA and OEA levels while improving depression and PTSD symptoms [161]. The relationship between PPAR-α and emotional regulation is further highlighted by its role as an anti-neuroinflammatory target [162, 163, 164, 165, 166].

It has been demonstrated that that stimulation of PPAR-α by PEA or synthetic agonists increased corticolimbic allopregnanolone levels in hippocampus, amygdala, and prefrontal cortex, which resulted in decreased contextual fear extinction and fear extinction retention, improved aggression and anxiety-like behavior in SI mice [120, 167]. PEA also induces antidepressant-like effects in SI mice [120]. Furthermore, this behavioral improvement by PEA or other PPAR-α synthetic agonists, which was associated with normalized allopregnanolone levels, was blunted by antagonism at PPAR-α, inhibition of allopregnanolone biosynthetic enzymes, and in PPAR-α KO mice. Other rodent studies have reported that exposure to predator stressors downregulates PEA and OEA levels (Holman et al., 2014), but elevating PEA and OEA levels results in antidepressant-like effects [168, 169, 170].

Figure 18:
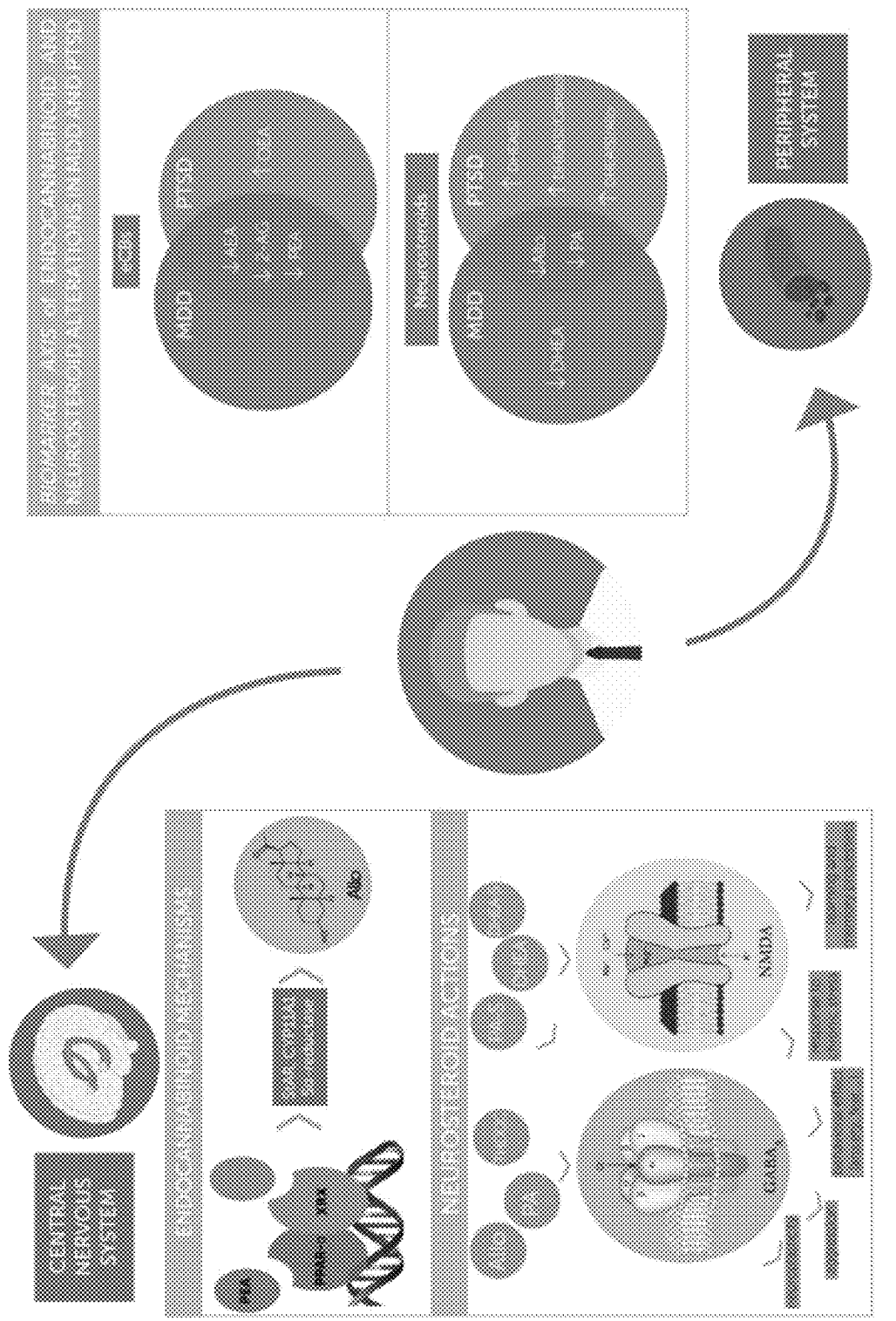
FIG. 18 shows a schematic that can demonstrate the role of endo cannabinoids and neurosteroids in a biomarker axis. The schematic representation shows the role of endocannabinoids (eCBs) and neurosteroids in the central nervous system (left panel), and their altered level in the peripheral tissue of PTSD and MDD patients (right panel). The eCBs, such as PEA and OEA activate the intracellular peroxisome proliferator-activated receptor (PPAR)-α, which heterodimerize with the retinoid X receptor (RXR). The PPAR-α and RXR complex binds to the consensus regions on the target gene promoters and initiates transcription. PEA, through the activation of PPAR-α, can enhance the induction of corticolimbic allopregnanolone (Allo) biosynthetic enzymes, including CYPIIAI and 5α-reductase, resulting in an enhanced neurosteroid synthesis (e.g., Allo). PEA levels and probably expression of PPAR-α are influenced by stress, which may negatively affect Allo's biosynthetic enzyme expression and allopregnanolone levels.

Altogether, these reports originating by preclinical and clinical studies support an emerging role of PPAR-α in MDD and PTSD. Furthermore, this new discovered interaction between PPAR-α activation and allopregnanolone levels may unveil biomarker axis uniquely altered at the interface of the endocannabinoid and the neurosteroid systems (FIG. 18).

Blood-Based Biomarker Axis.

Peripheral Biomarkers. All biomarkers discussed in this Example have been studied in animal models and in humans, with a focus on the CNS and CSF, serum and plasma [171, 172]. Noninvasive peripheral biomarkers are more useful and functional for diagnosis of disorders of mood and emotions. CSF reflects more closely the alterations of the brain but the procedure is stressful and results in pain and discomfort in the patients [173, 174]. Blood draws can also be stressful for some patients, putting at risk a precise diagnosis or may even turn patients away from testing. However, most studies are currently assessing serum- or plasma-based diagnostic tests [175], considering different biomarkers and several methods, including metabolomics (neurohormones, neuroactive steroids, endocannabinoids) or genomics and proteomics. The techniques used for the proteomics are immunoassays (ELISAs), but the mass spectrometry (MS)-coupled with 2D electrophoresis is now applied for the analysis of several proteins in biological tissues [176, 177]. While immunoassays present some limitations, principally due to large volume of sample required and limited amount of proteins that can be analyzed, the MS is making its way into proteomics as it provides unsurpassed structure selectivity. An advantage of this technique is the quantification of several biomarkers simultaneously in small samples; while, the disadvantages include very low reproducibility and the need of targeted analyses to discover a potential biomarker. In our laboratory, with the goal of assessing biomarkers, we employ the gas chromatography-mass spectrometry (GC-MS) to determine neuroactive steroids in CSF, serum and plasma of MDD and PTSD patients but also in mouse models of these disorders.

These results have identified specific changes in the axis of neuroactive steroid biosynthesis and their relation with neurotransmitter systems, including GABAA receptors

[120] (FIG. 18). Several protocols that consider not one, but several biomarkers are advantageous and have been recently proposed [178, 179]. These panels provide the evaluation of several biomarkers together: for example, Papakostas and colleagues proposed a test based on neuropeptides that gives an adequate sensitivity to distinguish MDD from non-depressed subjects [180]. Other studies considered a panel of blood transcriptomic biomarkers to predict early-onset MDD [181] and to identify depressed patients in remission or predict response to therapy [179]. Transcriptomics, including FAM46A, MARCKS and RAPH1 seem to be particular promising. Evaluation of blood-based tests also showed that candidate biomarker transcripts are promising for psychiatric disorders [179, 181, 182, 183]. Also, functional genomics tests have been proposed, analysis genes involved in several functions from myelination to growth factor signaling [178].

A consistent number of studies are currently working on assessing biomarker tests for MDD and PTSD, to provide a pre-clinical screening, a precise and accurate analytical validation of the marker, and a clinical validation. The process for a test-assessment based on biomarkers, from discovery to validation, is represented in FIG. 19.

REFERENCES FOR EXAMPLE 3

1. Benjet C, Bromet E, Karam E G, et al. Psychol Med. 2016 January; 46(2):327-43.
2. Breslau N, Kessler R C, Chilcoat H D, et al. Arch Gen Psychiatry. 1998 July; 55(7):626-32.
3. Bonanno G A, Diminich E D. Annual Research Review: Positive adjustment to adversity—trajectories of minimal-impact resilience and emergent resilience. J Child Psychol Psychiatry. 2013 April; 54(4):378-401.
4. White J, Pearce J, Morrison S, et al. Epidemiol Psychiatr Sci. 2015 June; 24(3):249-57.
5. Whiteford H A, Degenhardt L, Rehm J, et al. 2010. Lancet. 2013 Nov. 9; 382(9904):1575-86.
6. Demyttenaere K, Bruffaerts R, Posada-Villa J, et al. JAMA. 2004 Jun. 2; 291(21):2581-90.
7. Snyder H R. Psychol Bull. 2013 January; 139(1):81-132.
8. American Psychiatric Association. Diagnostic and Statistical Manual of Mental Disorders. 5th ed. Washington, D.C. 2013.
9. Bleich A, Koslowsky M, Dolev A, et al. British Journal of Psychiatry. 2018; 170(5):479-482.
10. Holma K M, Haukka J, Suominen K, et al. Bipolar Disord. 2014 September; 16(6):652-61.
11. Hawton K, Casanas I C C, Haw C, et al. J Affect Disord. 2013 May; 147(1-3):17-28.
12. Kokras N, Dalla C, Sideris A C, et al. Neuropharmacology. 2012 January; 62(1):436-45.
13. Pitychoutis P M, Nakamura K, Tsonis P A, et al. Neuroscience. 2009 Apr. 10; 159(4):1216-32.
14. Breslau N. Trauma Violence Abuse. 2009 July; 10(3):198-210.
15. De Bellis M D, Thomas L A. Current Psychiatry Reports. 2003 Apr. 1; 5(2):108-117.
16. Fu Q, Heath A C, Bucholz K K, et al. Psychological Medicine. 2002; 32(1):11-24.
17. Gill J, Vythilingam M, G. P G. Journal of Traumatic Stress. 2008; 21(6):530-539.
18. Koenen K C, Fu Q J, Ertel K, et al. Journal of Affective Disorders. 105(1):109-115.
19. Gottesman, I I, Gould T D. Am J Psychiatry. 2003 April; 160(4):636-45.
20. Carter J D, Frampton C M, Mulder R T, et al. J Affect Disord. 2010 July; 124(1-2):202-6.
21. Riedel M, Moller H J, Obermeier M, et al. J Psychiatr Res. 2010 November; 44(15):1063-8.
22. Altamura A C, Buoli M, Albano A, et al. Int Clin Psychopharmacol. 2010 May; 25(3):172-9.
23. Huerta-Ramirez R, Bertsch J, Cabello M, et al. J Affect Disord. 2013 Sep. 25; 150(3):1247-50.
24. Lakhan S E, Vieira K, Hamlat E. Int Arch Med. 2010 Jan. 12; 3:1.
25. Koenen K C, Harley R, Lyons M J, et al. J Nery Ment Dis. 2002 April; 190(4):209-18.
26. Voisey J, Swagell C D, Hughes I P, et al. Depress Anxiety. 2009; 26(1):28-33.
27. Caspi A, Sugden K, Moffitt T E, et al. Science. 2003 Jul. 18; 301(5631):386-9.
28. Yulug B, Ozan E, Kilic E. The Journal of Neuropsychiatry and Clinical Neurosciences. 2010; 22(1):123.e5-123.e6.
29. Hellgren C, Comasco E, Skalkidou A, et al. Hormones and Behavior. 2017
30. Zannas A S, West A E. Neuroscience. 2014 2014/04/04/; 264:157-170.
31. Meena Vythilingam, Christine Heim, Jeffrey Newport, et al. American Journal of Psychiatry. 2002; 159(12):2072-2080.
32. Nemeroff C B, Heim C M, Thase M E, et al. Proceedings of the National Academy o Sciences. 2003; 100(24):14293-14296.
33. Teicher M H, Andersen S L, Polcari A, et al. Neuroscience & Biobehavioral Reviews. 2003 2003/01/01/; 27(1):33-44
34. Provencal N, Binder E B. Curr Opin Neurobiol. 2015 February; 30:31-7.
35. Rampp C, Binder E B, Provencal N. Prog Mol Biol Transl Sci. 2014; 128:29-50.
36. Kwapis J L, Wood M A. Trends Neurosci. 2014 December; 37(12):706-20.
37. Cowen P J. Trends in Pharmacological Sciences. 2008 2008/09/01/; 29(9):433-436.
38. Anderson I M. Depress Anxiety. 1998; 7 Suppl 1:11-7.
39. Cowen P J. Pharmacol Ther. 1990; 46(1):43-51.
40. Kemp A H, Gordon E, Rush A J, et al. CNS Spectr. 2008 December; 13(12):1066-86
41. Lupien S J, McEwen B S, Gunnar M R, et al. Nat Rev Neurosci. 2009 June; 10(6):434-45.
42. Katz R J, Roth K A, Carroll B J. Neurosci Biobehav Rev. 1981 Summer; 5(2):247-51.
43. Holsboer F. Neuropsychopharmacology. 2000 November; 23(5):477-501.
44. Waters R P, Rivalan M, Bangasser D A, et al. Neurosci Biobehav Rev. 2015 November; 58:63-78.
45. Nemeroff C B, Vale W W. J Clin Psychiatry. 2005; 66 Suppl 7:5-13.
46. Koob G F, Zorrilla E P. Neuropsychopharmacology. 2012 January; 37(1):308-9.
47. Papiol S, Arias B, Gasto C, et al. J Affect Disord. 2007 December; 104(1-3):83-90.
48. Casat C D, Powell K. J Clin Psychiatry. 1988 October; 49(10):390-3.
49. Pariante C M. J Psychopharmacol. 2006 July; 20(4 Suppl):79-84.
50. Kalin N H, Cohen R M, Kraemer G W, et al. Neuroendocrinology. 1981 February; 32(2):92-5.
51. Miller A H, Spencer R L, Pulera M, et al. Biol Psychiatry. 1992 Nov. 15; 32(10):850-69.

52. Menke A, Arloth J, Putz B, et al. Neuropsychopharmacology. 2012 May; 37(6):1455-64.
53. Zannas A S, Binder E B. Genes Brain Behav. 2014 January; 13(1):25-37.
54. Binder E B, Salyakina D, Lichtner P, et al. Nat Genet. 2004 December; 36(12):1319-25.
55. Klengel T, Mehta D, Anacker C, et al. Nat Neurosci. 2013 January; 16(1):33-41.
56. Yehuda R, Cai G, Golier J A, et al. Biol Psychiatry. 2009 Oct. 1; 66(7):708-11.
57. Yehuda R. Psychiatry. 1999 February; 44(1):34-9.
58. Yehuda R, Daskalakis N P, Desarnaud F, et al. Front Psychiatry. 2013; 4:118.
59. Meaney M J, Ferguson-Smith A C. Nat Neurosci. 2010 November; 13(11):1313-8.
60. Zhang T Y, Labonte B, Wen X L, et al. Neuropsychopharmacology. 2013 January; 38(1):111-23.
61. McGowan P O, Sasaki A, D'Alessio A C, et al. Nat Neurosci. 2009 March; 12(3):342-8.
62. Hellstrom I C, Dhir S K, Diorio J C, et al. Philos Trans R Soc Lond B Biol Sci. 2012 Sep. 5; 367(1601):2495-510.
63. Di S, Maxson M M, Franco A, et al. J Neurosci. 2009 Jan. 14; 29(2):393-401.
64. Gourley S L, Kedves A T, Olausson P, et al. Neuropsychopharmacology. 2009 February; 34(3):707-16.
65. Higuchi H, Yang H Y, Sabol S L. J Biol Chem. 1988 May 5; 263(13):6288-95.
66. Tambuyzer B R, Ponsaerts P, Nouwen E J. J Leukoc Biol. 2009 March; 85(3):352-70.
67. Yirmiya R, Goshen I. Brain Behav Immun. 2011 February; 25(2):181-213.
68. Liu Y, Ho R C, Mak A. J Affect Disord. 2012 August; 139(3):230-9.
69. Pepys M B, Rowe I F, Baltz M L. Int Rev Exp Pathol. 1985; 27:83-111.
70. Priya P K, Rajappa M, Kattimani S, et al. Clin Chim Acta. 2016 Jun. 1; 457:41-5.
71. Spitzer C, Barnow S, Volzke H, et al. J Psychiatr Res. 2010 January; 44(1):15-21.
72. Harley J, Luty S, Carter J, et al. J Psychopharmacol. 2010 April; 24(4):625-6.
73. Uher R, Tansey K E, Dew T, et al. Am J Psychiatry. 2014 Dec. 1; 171(12):1278-86.
74. Wium-Andersen M K, Orsted D D, Nielsen S F, et al. JAMA Psychiatry. 2013 February; 70(2):176 84.
75. Hannestad J, DellaGioia N, Bloch M. Neuropsychopharmacology. 2011 November; 36(12):2452-9.
76. Baune B T, Dannlowski U, Domschke K, et al. Biol Psychiatry. 2010 Mar. 15; 67(6):543-9.
77. Kovacs D, Eszlari N, Petschner P, et al. J Neural Transm (Vienna). 2016 May; 123(5):541-8.
78. Zakharyan R, Petrek M, Arakelyan A, et al. Tissue Antigens. 2012 August; 80(2):136-42.
79. Sukoff Rizzo S J, Neal S J, Hughes Z A, et al. Transl Psychiatry. 2012 Dec. 4; 2:e199.
80. Dowlati Y, Herrmann N, Swardfager W, et al. Biol Psychiatry. 2010 Mar. 1; 67(5):446-57.
81. Eller T, Vasar V, Shlik J, et al. Prog Neuropsychopharmacol Biol Psychiatry. 2008 Feb. 15; 32(2):445-50.
82. Powell T R, Schalkwyk L C, Heffernan A L, et al. Eur Neuropsychopharmacol. 2013 September; 23(9):1105-14.
83. Huang E J, Reichardt L F. Annu Rev Neurosci. 2001; 24:677-736.
84. Murakami S, Imbe H, Morikawa Y, et al. Neurosci Res. 2005 October; 53(2):129-39.
85. Mondelli V, Cattaneo A, Murri M B, et al. J Clin Psychiatry. 2011 December; 72(12):1677-1684.
86. Kikusui T, Ichikawa S, Mori Y. Psychoneuroendocrinology. 2009 June; 34(5):762-72.
87. Sousa N, Madeira M D, Paula-Barbosa M M. Brain Res. 1998 Jun. 1; 794(2):199-210.
88. Barbany G, Persson H. Eur J Neurosci. 1992; 4(5):396-403.
89. Cattaneo A, Bocchio-Chiavetto L, Zanardini R, et al. Int J Neuropsychopharmacol. 2010 February; 13(1):103-8.
90. Fernandes B S, Berk M, Turck C W, et al. Mol Psychiatry. 2014 July; 19(7):750-1.
91. Hauck S, Kapczinski F, Roesler R, et al. Progress in Neuro-Psychopharmacology and Biological Psychiatry. 2010
92. Dell'Osso L, Carmassi C, Del Debbio A, et al. Progress in Neuro-Psychopharmacology and Biological Psychiatry. 2009 2009/08/01/; 33(5):899-902.
93. Berger W, Mehra A, Lenoci M, et al. Prog Neuropsychopharmacol Biol Psychiatry. 2010 Oct. 1; 34(7):1279-84. doi: 10.1016/j.pnpbp.2010.07.008.
94. Lisiecka D M, O'Hanlon E, Fagan A J, et al. J Affect Disord. 2015 Sep. 15; 184:239-44.
95. Notaras M, Hill R, van den Buuse M. Mol Psychiatry. 2015 August; 20(8):916-30.
96. Brooks S J, Nilsson E K, Jacobsson J A, et al. PLoS One. 2014; 9(1):e82707.
97. Harrisberger F, Spalek K, Smieskova R, et al. Neuroscience & Biobehavioral Reviews. 2014 2014/05/01/; 42:267-278.
98. Gatt J M, Nemeroff C B, Dobson-Stone C, et al. Mol Psychiatry. 2009 July; 14(7):681-95.
99. Hassan A M, Jain P, Reichmann F, et al. Front Behav Neurosci. 2014; 8:386.
100. Heilig M. Neuropeptides. 2004 August; 38(4):213-24.
101. Thorsell A, Carlsson K, Ekman R, et al. Neuroreport. 1999 Sep. 29; 10(14):3003-7.
102. Cavagnini F, Croci M, Putignano P, et al. Int J Obes Relat Metab Disord. 2000 June; 24 Suppl 2:S77-9.
103. Baldock P A, Lin S, Zhang L, et al. J Bone Miner Res. 2014 October; 29(10):2238-49.
104. Bertocchi I, Oberto A, Longo A, et al. Proc Natl Acad Sci USA. 2011 Nov. 29; 108(48):19395-400.
105. Schmidt M V, Liebl C, Sterlemann V, et al. J Endocrinol. 2008 May; 197(2):421-7.
106. Morgan C A, 3rd, Wang S, Southwick S M, et al. Biol Psychiatry. 2000 May 15; 47(10):902-9.
107. Rasmusson A M, Hauger R L, Morgan C A, et al. Biol Psychiatry. 2000 Mar. 15; 47(6):526-39.
108. Sah R, Ekhator N N, Jefferson-Wilson L, et al. Psychoneuroendocrinology. 2014 February; 40:277-83.
109. Nishi D, Hashimoto K, Noguchi H, et al. Neurosci Res. 2014 June; 83:8-12.
110. Yehuda R, Brand S, Yang R K. Biol Psychiatry. 2006 Apr. 1; 59(7):660-3.
111. Zhou Z, Zhu G, Hariri A R, et al. Nature. 2008 Apr. 24; 452(7190):997-1001.
112. Brothers S P, Wahlestedt C. EMBO Mol Med. 2010 November; 2(11):429-39.
113. Agis-Balboa R C, Pinna G, Zhubi A, et al. Proc Natl Acad Sci USA. 2006 Sep. 26; 103(39):14602-7.
114. Baulieu E E, Robel P. J Steroid Biochem Mol Biol. 1990 Nov. 20; 37(3):395-403.
115. Belelli D, Peden D R, Rosahl T W, et al. J Neurosci. 2005 Dec. 14; 25(50):11513-20.
116. Pinna G, Uzunova V, Matsumoto K, et al. Neuropharmacology. 2000 Jan. 28; 39(3):440-8.

117. He J, Hoffman S W, Stein D G. Restor Neurol Neurosci. 2004; 22(1):19-31.
118. Smith S S, Waterhouse B D, Chapin J K, et al. Brain Research. 1987
119. Vyklicky V, Smejkalova T, Krausova B, et al. J Neurosci. 2016 Feb. 17; 36(7):2161-75.
120. Locci A, Pinna G. British Journal of Pharmacology. 2017; 174(19):3226-3241.
121. Zorumski C F, Mennerick S. JAMA Psychiatry. 2013 July; 70(7):659-60.
122. Agis-Balboa R C, Fischer A. Cell Mol Life Sci. 2014 January; 71(1):21-42.
123. Romeo E, Strohle A, Spalletta G, et al. American Journal of Psychiatry.
124. Uzunova V, Sheline Y, Davis J M, et al. P. Natl Acad Sci USA. 1998; 95(6):3239-3244.
125. van Broekhoven F, Verkes R J. Psychopharmacology. 2003; 165(97).
126. Dichtel L E, Lawson E A, Schorr M, et al. Neuropsychopharmacology. 2018 May; 43(6):1436-1444.
127. Nemeroff C B. Neuron. 2008 Jul. 31; 59(2):185-6.
128. Rasmusson A M, Pinna G, Paliwal P, et al. Biol Psychiatry. 2006 Oct. 1; 60(7):704-13.
129. Pinna G, Costa E, Guidotti A. Psychopharmacology (Berl). 2006 June; 186(3):362-72.
130. Rasmusson A M, Pinna G, Paliwal P, et al. Biological Psychiatry. 60(7):704-713.
131. Rasmusson A. P450 enzyme blocks in the progesterone GABAergic neuroactive steroid synthesis pathway in PTSD: sex differences. 2nd Neurosteroid Congress; Apr. 6-8 (2016); Durham, N.C. 2016.
132. Gillespie C F, Almli L M, Smith A K, et al. Am J Med Genet B Neuropsychiatr Genet. 2013 April; 162B(3):283-292.
133. Eicheler W, Tuohimaa P, Vilja P, et al. J Histochem Cytochem. 1994 May; 42(5):667-75.
134. Purdy R H, Morrow A L, Moore P H, Jr., et al. Proc Natl Acad Sci USA. 1991 May 15; 88(10):4553-7.
135. Chalbot S, Morfin R. Drug Metabol Drug Interact. 2006; 22(1):1-23.
136. Pitman R K, Rasmusson A M, Koenen K C, et al. Nat Rev Neurosci. 2012 November; 13(11):769-87.
137. Dong E, Matsumoto K, Uzunova V, et al. Proc Natl Acad Sci USA. 2001 Feb. 27; 98(5):2849-54.
138. Nin M S, Martinez L A, Pibiri F, et al. Front Endocrinol (Lausanne). 2011; 2:73.
139. Pibiri F, Nelson M, Guidotti A, et al. Proc Natl Acad Sci USA. 2008 Apr. 8; 105(14):5567-72.
140. Geuze E, van Berckel B N, Lammertsma A A, et al. Mol Psychiatry. 2008 January; 13(1):74-83, 3.
141. Pinna G, Rasmusson A M. Front Cell Neurosci. 2014; 8:256.
142. Pinna G, Dong E, Matsumoto K, et al. P Natl Acad Sci USA. 2003; 100(4):2035-2040.
143. Schule C, Eser D, Baghai T C, et al. Neuroscience. 2011 Sep. 15; 191:55-77.
144. Zhang L-M, Qiu Z-K, Zhao N, et al. International Journal of Neuropsychopharmacology. 2014; 17(10):1659-1669.
145. Kanes S J, Colquhoun H, Doherty J, et al. Human Psychopharmacology: Clinical and Experimental. 2017; 32(2).
146. Morena M, Roozendaal B, Trezza V, et al. P Natl Acad Sci USA. 2014 Dec. 23; 111(51):18333-18338.
147. Hill M N, Gorzalka B B. Behav Pharmacol. 2005 September; 16(5-6):333-52.
148. Valverde O, Torrens M. Neuroscience. 2012 Mar. 1; 204:193-206.
149. Neumeister A, Normandin M D, Pietrzak R H, et al. Mol Psychiatry. 2013 September; 18(9):1034-40.
150. Hungund B L, Vinod K Y, Kassir S A, et al. Mol Psychiatry. 2004 February; 9(2):184-90.
151. Juhasz G, Chase D, Pegg E, et al. Neuropsychopharmacology. 2009 July; 34(8):2019-27.
152. Monteleone P, Bifulco M, Maina G, et al. Pharmacol Res. 2010 May; 61(5):400-4.
153. Hill M N, Miller G E, Carrier E J, et al. Psychoneuroendocrinology. 2009 September; 34(8):1257-62.
154. Hill M N, Carrier E J, McLaughlin R J, et al. J. Neurochemistry. 2008; 106(6):2322-2336.
155. Hauer D, Schelling G, Gola H, et al. PLoS One. 2013; 8(5):e62741.
156. Hillard C J. Neuropsychopharmacology. 2018; 43(1):155.
157. Dlugos A, Childs E, Stuhr K L, et al. Neuropsychopharmacology. 2012; 37(11):2416.
158. Darmani N A, Izzo A A, Degenhardt B, et al. Neuropharmacology. 2005; 48(8):1154-1163.
159. Sabelli H C, Javaid J I. Therapeutic and Diagnostic Implications. Neurosciences. 1995; 7:6 14.
160. Ghazizadeh-Hashemi M, Ghajar A, Shalbafan M R, et al. J Affect Disord. 2018 May; 232:127-133.
161. Heyman E, Gamelin F X, Goekint M, et al. Psychoneuroendocrinology. 2012 June; 37(6):844-51.
162. Rolland B, Deguil J, Jardri R, et al. Current drug targets. 2013; 14(7):724-732.
163. Esmaeili M A, Yadav S, Gupta R K, et al. Human molecular genetics. 2015; 25(2):317-327.
164. Racke M K, Drew P D. PPARs in neuroinflammation. PPAR research. 2008; 2008.
165. Jeon S W, Kim Y K. World journal of psychiatry. 2016 Sep. 22; 6(3):283-93.
166. O'Leary A. Psychological bulletin. 1990; 108(3):363.
167. Locci A, Geoffroy P, Miesch M, et al. Front Cell Neurosci. 2017; 11:208.
168. Adamczyk P, Golda A, McCreary A C, et al. J Physiol Pharmacol. 2008 June; 59(2):217-28.
169. Melis M, Scheggi S, Carta G, et al. J Neuroscience. 2013; 33(14):6203-6211.
170. Umathe S N, Manna S S, Jain N S. Behav Brain Res. 2011 Sep. 30; 223(1):125-34.
171. Stahl S M. The human platelet: Archives of General Psychiatry. 1977; 34(5):509-516.
172. Su T, Zhang L, Chung M, et al. J. Psychiatric Research. 2009; 43(13):1078-1085.
173. Holzman I R. Traumatic Lumbar Punctures. Pediatrics. 2004; 113(1):172-172.
174. Kaushal H S, Kathleen M R, Sarah N, et al. Emergency Medicine. 2003; 10(2):151-154.
175. Glass L. Nature. 2001 Mar. 8; 410(6825):277-84.
176. Hrabak J, Chudáčkova E, Walkova R. Clinical Microbiology Reviews. 2013 Jan. 1, 2013; 26(1):103-114.
177. Lagace-Wens P R S, Adam H J, Karlowsky J A, et al. J. Clinical Microbiology. 2012 Oct. 1, 2012; 50(10):3324-3328.
178. Le-Niculescu H, Kurian S M, Yehyawi N, et al. Mol Psychiatry. 2009 February; 14(2):156-74.
179. Redei E E, Andrus B M, Kwasny M J, et al. Transl Psychiatry. 2014 Sep. 16; 4:e442.
180. Papakostas G I, Shelton R C, Kinrys G, et al. Mol Psychiatry. 2013 March; 18(3):332-9.
181. Pajer K, Andrus B M, Gardner W, et al. Transl Psychiatry. 2012 Apr. 17; 2:e101.

182. Mehta-Raghavan N S, Wert S L, Morley C, et al. Transl Psychiatry. 2016 Mar. 29; 6:e770.
183. Redei E E, Mehta N S. Annals of the New York Academy of Sciences. 2015; 1344(1):37-49.

Example 4

In the search for reliable and, possibly, specific biomarkers for neuropsychiatric disorders, growing evidence has demonstrated that biosynthesis of neuroactive steroids and the endocannabinoid system are involved in the neuropathology of post-traumatic stress disorder (PTSD) and major depressive disorder (Rasmusson et al., 2006, Uzunova et al., 1998, Locci and Pinna, 2017a) (FIG. 5).

Although, undisputable progress has been made to assess validity of biomarkers for psychiatric disorders, the topic still remains underdeveloped as compared to other fields of neuroscience (Fernandes et al., 2017). The diagnosis of psychiatric disorders still relies on subjective measures centered on the DSM-5 criteria which have several shortcomings (Brewin et al., 2017). Psychiatric conditions are poorly understood and there is a wide heterogeneity in how illness manifests in several individuals. Furthermore, self-assessment of one's own feelings can be biased, ill-defined, and difficult, making psychological diagnoses unreliable and may lead to treatment inefficacy. Thus, searching for potential biomarkers to guide precision medicine in the treatment of PTSD, and to increase the success of clinical trials and prompt the development of novel and specific treatments, is required. To aid this search, more sophisticated methodological tools and validated animal models has also become essential to reliably correlate a behavioral changes with neurochemical alterations (reviewed in Ngounou Wetie et al., 2013).

The overlap of symptoms and the comorbidity with other psychiatric disorders such as major depressive disorder, anxiety spectrum disorders, and even suicidal ideation (Franklin et al., 2018), suggest a biosignature for PTSD should include numerous biomarkers (Locci and Pinna, 2017a). A refined approach to more specifically "bio-define" PTSD can be to establish a biomarker axis or in other words, to assess the relation of numerous biomarkers as opposed to only a few (Loci and Pinna, 2017a), which fluctuate in concert and correlate uniquely with PTSD-like behavioral modifications. Insofar, a biomarker axis may provide a higher accuracy in the diagnosis of the disorder with benefits for prediction in PTSD treatment response and relapse (Pinna and Izumi, 2018; Locci et al., 2018). As a matter of fact, the gold standard treatment for PTSD and depression, the selective serotonin reuptake inhibitors (SSRIs), improve only half of the treatment-seeking patients and they are associated with severe side-effects (reviewed in Bernardy and Friedman, 2017; Bernardy and Friedman, 2015; Golden, et al., 2002; Rush et al., 2006; Kemp et., 2008). This also suggests these psychiatric disorders are complex, multifaceted diseases arising from multiple and diverse neurobiological backgrounds and therefore, symptoms may not always recapitulate to a serotonergic deficit and administering SSRIs may not improve symptoms. Unveiling reliable biomarkers is also a necessity for patient stratification in treatment selection as well as for drug development through clinical trials.

Working with the gas chromatography-mass spectrometry (GC-MS) can provide reliable information based on a powerful technology with high sensitivity and unsurpassed structure selectivity (Uzunov et al., 1996; Pinna et al., 2000). Hence, by applying the GC-MS measurements of neuroactive steroids in serum, plasma, CSF and post-mortem brain, in the past decade, we have shed light in the fundamental role of neuroactive steroids in patients with neuropsychiatric disorders (Rasmusson et al., 2006; 2016; 2017; Pineles et al., 2018m Locci and Pinna, 2017a).

The biosynthesis of allopregnanolone, a positive allosteric modulator of GABA's action at $GABA^A$ receptors has been found deficient in a number of neuropsychopathologies, including epilepsy (eg., PHDH19), major depression, PTSD, perceived social isolation, post-partum depression, premenstrual syndrome, and anorexia nervosa or obesity complicated by anxiety and depression symptoms in women (Trivisano et al., 2017; Uzunova et al., 1998; Romeo et al., 1998; Rasmusson et al., 2006; Nemerof et al., 2008; Lovick, 2013; Dichtel et al., 2018, Pineles et al., 2018). Therapeutic measures aimed at reinstating normal allopregnanolone levels in deficient-patients correlates with improved symptoms (Kane et al., 2017). The question arises as to whether allopregnanolone biosynthesis per se is a reliable biomarker to predict, diagnose and instruct treatment selection of patients or whether its relation with neurotransmitter systems ($GABA_A$ and NMDA receptors), stimulation of neurotropic factors (e.g., BDNF), and/or crosstalk with the endocannabinoid system (e.g., PPAR-α) may provide a valuable biomarker axis with a higher disorderselectivity. This analysis includes both neurosteroids that are positive allosteric modulators of $GABA_A$ receptors (Pinna et al., 2000; Belelli and Lambert, 2005), such as allopregnanolone and pregnanolone and their sulfated forms that are inhibitors of NMDA-mediated tonic neurotransmission (Vyklicky et al., 2016), which can result in neuroprotection. The unforeseen behavioral and neurosteroidogenic function of PPAR-α, formally known to regulate pathophysiological functions, including inflammation and oxidative stress, opens the field for potential biomarkers for PTSD.

This Example will discuss a biomarker role for allopregnanolone biosynthesis and the endocannabinoid system for stress-induced disorders. The strategy of assessing a biomarker axis, which can indicate the relation of various inter-related neurobiological deficits for one disorder (FIG. 20), may help for diagnosis accuracy and for designing successful individualized treatments.

The unforeseen behavioral and neurosteroidogenic function of PPAR-α, formally known to regulate pathophysiological functions, including inflammation and oxidative stress, opens the field for potential biomarkers for PTSD.

Neurosteroid Action at $GABA_A$ and NMDA Receptors. Sulfated or unconjugated neuroactive steroids modulate ionotropic amino acid neurotransmitter receptors, including $GABA_A$ and NMDA receptors. The $GABA_A$ receptor offers two binding residues that express affinity for allopregnanolone and unconjugated congeners (e.g., pregnanolone) that act as potent positive allosteric modulators of the action of GABA at $GABA_A$ receptors. One is located at the interface of the α/β subunits, and the other is within the cavity of a subunits (Hosie et al., 2006). The α,β,γ $GABA_A$ receptor subtype is the most frequent synaptic configuration and is highly sensitive to benzodiazepines but shows lower sensitivity to GABA and neurosteroids (Nusser and Mody, 2002). The α,β,δ GABAA receptor subtype expressed in the extrasynaptic region is benzodiazepine-insensitive, show low efficacy for GABA, but neurosteroids increase its agonist efficacy (Stell et al., 2003; Shu et al., 2012). This receptor combination shows high efficacy for neurosteroids (Brown et al., 2002; Nusser and Mody, 2002; Wohlfarth et al., 2002). See e.g. FIG. 5.

Sulfated neurosteroids such as pregnenolone sulfate, dehydroepiandrosterone sulfate, pregnanolone sulfate and allopregnanolone sulfate may function as endogenous neuromodulators by inhibiting $GABA_A$ receptors, or pending on the receptor conformation and the sulfated neuroactive steroid examined, by activating or inhibiting NMDA-mediated neurotransmission (Park-Chung et al., 1999). Sulfation at $C_3$ is essential to reverse the direction of modulation from positive to negative in $GABA_A$ receptors. Steroid negative and positive modulators act through distinct sites, which implies that steroid negative and positive modulators can act independently or coordinately to modulate the flavor of GABAergicmediated inhibitory neurotransmission (reviewed in Smith et al., 2014). While, micromolar concentrations of pregnenolone sulfate negatively modulate $GABA_A$ receptors, pregnenolone sulfate can negatively or positively modulate NMDA receptors, depending on the subunits expressed (Malayev et al., 2002; Smith et al., 2014). For instance, pregnenolone sulfate potentiates NMDA receptors that contain NR2A and NR2B subunits, but negatively modulates NR2C and NR2D-containing receptors (Malayev et al., 2002).

Recent studies showed that pregnanolone sulfate has a potent inhibitory action at tonic rather than synaptically-activated NMDA receptors, which provides neuroprotection and possibly improves emotional behavior and cognition (Vyklicky et al., 2016). This feature is relevant for developing a novel class of steroid-based NMDA inhibitors devoid of the psychotomimetic effects that characterize classical NMDA receptor inhibitors, including ketamine.

While $GABA_A$ receptor subunit expression during protracted stress has been previously investigated (discussed below), the role and action of sulfated pregnanolone, pregnenolone, allopregnanolone, and the expression of NMDA receptor subunit in PTSD patients and in rodent stress models, still warrants elucidation.

The neurosteroid and endocannabinoid crosstalk. Intriguingly, studies conducted in cell cultures, brainstem and spinal cord showed the endocannabinoid, N-palmitoylethanolamine (PEA) binding at the ligand-activated nuclear receptor, peroxisome proliferator-activated receptor (PPAR-α) stimulates allopregnanolone biosynthesis and potentiates pentobarbital-induced sedation (Sasso et al., 2010, 2012; Raso et al., 2012). These observations suggest that PPAR-α may play a role in the regulation of emotions by inducing neurosteroidogenesis in corticolimbic neurons following binding with its endogenous ligand, PEA, or synthetic agonists.

Whereas, the cannabinoid receptor type 1 (CB1) has been shown to regulate emotions and stress responses, PPAR-α's role on emotions remains poorly understood (Haring et a., 2012; Riebe and Wotjak, 2011). The relevance of the endocannabinoid system in behavior is highlighted by expression of CB1 and PPAR-α in glutamatergic neurons of emotion-relevant areas that are important for PTSD (amygdala, hippocampus, frontal cortex) (Katona, 2009; Moreno et al., 2004; Lo Verme et al., 2005; Petrosino et al., 2017; D'Agostino et al. 2009). Moreover, evidence suggests CB1 disruption, leads to impaired fear extinction (Reich et al., 2008), depressive- and anxiety-like behavior, while agonists, like AEA, induce anxiolysis and improves fear responses (Hill and Patel, 2013). Current thought suggests that the effects of AEA at CB1 account for the majority of anti-fear effects (Jacob et al., 2012; Viveros et al., 2005; Kamprath et al., 2006; Thiemann et I., 2008; Marsicano et al., 2002), however this view seems no longer tenable (Pistis and Melis, 2010). In addition to these cell-surface cannabinoid receptors, there is growing evidence that PPAR-α's activation represents a novel mechanism by which cannabinoids modulate behavior. Stimulation of PPAR-α by PEA or synthetic agonists was recently shown to elevate cortico-limbic allopregnanolone levels in hippocampus, amygdala, prefrontal cortex and in olfactory bulb, which correlated with improvement of PTSD-like behavior in socially isolated mice (Locci and Pinna, 2017a). PEA facilitates contextual fear extinction and fear extinction retention and induces anti-aggressive, anxiolytic, and antidepressant-like effects in socially isolated mice (Locci et al., 2017, Locci and Pinna, 2017b). PPAR-α synthetic agonists normalized allopregnanolone levels and improved behavior, whereas antagonism at PPAR-α, inhibition of allopregnanolone biosynthetic enzymes, or PPAR-αKO mice prevented both PEA-induced behavior and its neurosteroidogenic effects (Locci and Pinna, 2017b).

While the role of PPAR-α in neuropsychiatric disorders is just emerging, studies in the field suggest serum PEA and OEA levels increase after acute social stressor (Dlugos et al., 2012) and decrease after recovery (Hill et al., 2009a). Stress evokes fast induction of FAAH, which reduces PEA levels (Patel et al., 2005; Hill et al., 2009b). In PTSD patients, symptoms are inversely correlated with reduced hair levels of PEA, OEA and SEA in both males and females (Wilker et al., 2016). PEA adjunctive therapy to citalopram improves symptoms in depressed patients (Ghazizadeh-Hashemi et al., 2018). Furthermore, intense workouts increase PEA and OEA levels and improve depression and PTSD (Heyman et al., 2012). In rodents, exposure to predator stressors reduces PEA and OEA levels (Holman et al., 2014), but, antidepressant-like effects are induced by increasing PEA and OEA (Adamczyk et al., 2008; Umathe et al., 2011; Melis et al., 2013).

Collectively, the crosstalk between the endocannabinoid system and neurosteroid biosynthesis during stress may unveil biomarker axis uniquely altered in specific stress-induced mood disorders.

Biomarkers and Treatment Options for PTSD at the Interface of the Endocannabinoid and Neurosteroid Axis.

Neuropsychiatric disorders, such as PTSD, are not currently amenable to objective neurobiological determinations as is routine practice in the diagnosis and treatment of other medical conditions. This is likely due to the general complexity and multifactorial origins of these disorders and the difficulty to establish a consistent bio-signature. No biomarkers for PTSD have to date been firmly assessed with diagnostic validity. Biomarker candidates for PTSD have been proposed but often they share overlaps with other psychiatric disorders with similar symptoms and that are currently treated with the same drugs, Indeed, the first-choice pharmacological treatments for PTSD, the SSRIs, act through multiple molecular mechanisms other than by inhibiting serotonin reuptake. These mechanisms include the stimulation of neurosteroid and endocannabinoid biosynthesis and neurotrophic factors, such as BDNF, which are found deficient in PTSD. Increasing allopregnanolone levels is also associated with increased BDNF expression (Nin et al., 2011). Collectively, these findings have contributed to improve our understanding of the psychobiological abnormalities associated with PTSD and promote the development of novel targeted treatment options. For instance, the correlation between the impairment of neurosteroid biosynthesis and behavioral modifications in neuropsychiatric disorders has been the focus of several studies (van Broekhoven and Verkes, 2003; Agis-Balboa et al., 2014; reviewed in Pinna, 2014 and Locci & Pinna, 2017a). A reduction in the content of the GABAergic modulator allopregnanolone and its equipotent isomer pregnanolone was reported in cerebrospinal fluid (CSF) and serum of major depression and PTSD patients (Uzunova et al., 1998; Romeo et al., 1998; Rasmusson et al., 2006; 2016; Pineles et al., 2018). A negative correlation between CSF allopregnanolone levels and PTSD symptoms was more recently confirmed in male patients (Rasmusson et al., 2018). Other clinical studies support the significance of allopregnanolone biosynthesis as a biomarker of mood disorders (Uzunova et al., 1998; Agis-Balboa et al., 2014; reviewed in Zorumski et al., 2013, Schule, 2014; and Locci and Pinna, 2017) with finding showing decreased allopregnanolone levels in postpartum depression (Nemeroff, 2008), under treatment with finasteride, an allopregnanolone biosynthetic enzyme blocker (Altomare, & Capella, 2002; Caruso et al., 2015; Welk et al., 2017), and with anorexia nervosa or obese complicated by anxiety and depression (Dichtel et al., 2018). Intriguingly, SSRI treatments normalize plasma, CSF, and brain allopregnanolone content in association with improvement of symptoms (Romeo et al., 1998; Uzunova et al., 1998; Agis-Balboa et al., 2014). These findings are in support of the role of allopregnanolone in the mechanisms of SSRIs' anxiolytic effects (Pinna, 2015).

The downregulation of neurosteroid levels found in PTSD and depressed patients can be modeled in rodents exposed to protracted of stress, including the socially-isolated mouse. Allopregnanolone is produced in brain corticolimbic neurons and (FIG. 5) a reduction of its levels by prolonged social isolation (Agis-Balboa et al., 2006; 2007) or exposure to single prolonged stressors, result in development of anxiety-like behavior, aggression and enhanced contextual fear conditioning responses associated with impairment of fear extinction and elevated spontaneous fear responses at recall (Dong et al., 2001; Pibiri et al., 2008; Zhang et al., 2014; Pinna and Rasmusson, 2014). These preclinical studies further support allopregnanolone as a putative biomarker for stress-induced emotional modification, such as exaggerated fear responses and impaired fear extinction, a core feature of PTSD (Pinna et al., 2008; Pibiri et al, 2008; Pinna and Rasmusson, 2011). This evidence also suggests that new therapeutic approaches should counteract the downregulation of neurosteroid biosynthesis to improve symptoms in PTSD patients. In a recent phase 3 clinical trial, intravenous allopregnanolone (brexanolone or SAGE-547) or an oral analog (SAGE-217) showed a rapid and long-lasting remission of post-partum depression symptoms and major depressive disorder symptoms (Kanes et al., 2017). Stress tremendously affects the expression of GABAA receptor subunits (reviewed in Locci and Pinna, 2017).

After social isolation, the $\alpha 4$, $\alpha 5$ and $\delta$ subunit expression was increased, and the $\alpha 1$, $\alpha 2$ and $\gamma 2$ was significantly decreased in corticolimbic areas (Pinna et al., 2006b; Pibiri et al., 2008). These changes result in decreased benzodiazepine recognition sites and lower pharmacological response to benzodiazepines (Pinna et al., 2006b; Nin et al., 2011a). Remarkably, protracted stress favors a $GABA_A$ receptor composition with high sensitivity for allopregnanolone and its analogs (Locci et al., 2017). Clinical findings support lower benzodiazepine recognition sites in brain of PTSD patients in association with benzodiazepine-insensitivity (Geuze et al., 2008). Altogether, these findings suggest that isolation stress results in: i) changes in $GABA_A$ receptor subunit composition; ii) downregulated neurosteroidogenesis; and iii) lack of response to benzodiazepines, which may provide a unique biomarker axis for PTSD (FIG. 20).

The pharmacological profile of SSRIs on stimulation of neurotropic factors, including the brain derived neurotrophic factor (BDNF), via stimulation of allopregnanolone biosynthesis is an additional mechanism to consider when establishing biomarkers for PTSD. BDNF expression decrease in PTSD patients is associated with symptom severity. In the socially isolated mouse, fluoxetine improves behavior by elevating the corticolimbic levels of allopregnanolone and BDNF expression, independently from the action of these drugs on serotonin reuptake inhibition.

Biomarkers that instruct which treatment would be most effective for a patient is expected to considerably reduce non-responders and non-completers rate. Following activation of PPAR-$\alpha$, undoubtedly their cross-talk offers a unique opportunity to assess a biomarker axis that encompasses these two systems (FIG. 20). Both endocannabinoids and neurosteroids can be measured by GC-MS, however, presently there is no method that can determine them simultaneously in the same samples.

FIG. 5 can demonstrate the regulation of emotional behavior via endocannabinoid and neurosteroid systems cross-talk. The neurosteroid, allopregnanolone (Allo) and its equipotent isomer pregnanolone (PA) are primarily synthesized in glutamatergic neurons and upon secretion, they may act at $GABA_A$ receptors located on cell bodies or dendrites of distal pyramidal neurons (Arrow 1, FIG. 5). They may also act at $GABA_A$ receptors located on glutamatergic neurons' dendrites or cell bodies by an autocrine mechanism (Arrow 2, FIG. 5), or may access and act at the intracellular sites of GABAA receptors located in glutamatergic neurons that produced allopregnanolone itself (Arrow 3, FIG. 5) (Agis-Balboa et al., 2006; 2007; Pinna et al., 2008). Allopregnanolone can play a central neuromodulatory role in facilitating the action of GABA at $GABA_A$ receptors (a primary target of anxiolytics) and in the fine-tuning of the receptor for agonists and GABA mimetic agents (Pinna et al., 2000). The finding that allopregnanolone facilitates the efficacy of $GABA_A$ receptor allosteric modulators substantiates its endogenous physiological relevance (Pinna et al., 2000; 2008; Guidotti et al., 2001). $GABA_A$ receptors composed by $\alpha,\beta,\gamma$ subunits are the most common configuration in the synaptic membranes and they are responsible for the inhibitory phasic currents. These receptors are benzodiazepine-sensitive but show lower sensitivity to GABA and allopregnanolone (Nusser and Mody, 2002). The $GABA_A$ receptors including $\alpha,\beta,\delta$ subtypes are mostly extrasynaptic and mediate inhibitory tonic currents. They are not sensitive to benzodiazepines and show low efficacy for GABA, however, allopregnanolone increase their efficacy (Stell et al., 2003; Shu et al., 2012). The efficacy of GABAergic neurosteroids is greatly enhanced for this receptor combination (Brown et al., 2002; Nusser and Mody, 2002; Wohlfarth et al., 2002). Remarkably, protracted stress favors a $GABA_A$ receptor composition with high sensitivity for allopregnanolone and its analogs (Locci and Pinna, 2017a).

Following the action of sulphotransferase, allopregnanolone and pregnanolone can be transformed into allopregnanolone sulfate (Allo-S) and pregnanolone sulfate (PAS). These sulfated steroids can be measured by gas chromatography-mass spectrometry in serum, CSF, and brain of patients or rodents in concentrations consistent with a physiological role in modulating neurotransmitter systems (Smith et al., 2014; Locci and Pinna, 2017b). Recently, pregnanolone sulfate has been shown to inhibit NMDA receptors. Pregnanolone sulfate can accumulate in plasma membranes and may accesses binding sites that are located at NMDA receptors (Borovska et al., 2012). Pregnanolone sulfate, and probably allopregnanolone sulfate, is highly potent at inhibiting tonic rather than synaptically mediated NMDA receptor neurotransmissions. While synaptic NMDA receptors play a pivotal role in synaptic plasticity, learning and memory, as well as in synaptogenesis, tonic-mediated NMDA receptor neurotransmission is mostly involved with excitotoxicity. Thus, the effects of pregnanolone sulfate negative modulation of tonic-mediated NMDA receptor neurotransmission have relevance for neuroprotection (Vyklicky et al., 2016). By this mechanism, these allopregnanolone and pregnanolone sulfated derivatives may play a role in the regulation of cognitive processes and of emotional behavior (reviewed in Locci and Pinna, 2017a).

There is growing evidence that the intracellular peroxisome proliferator-activated receptor (PPAR-α), members of the ligand-activated nuclear steroid receptorsuperfamily (O'Sullivan, 2007; Forman et al., 1996), is also a cannabinoid target. PPAR-α heterodimerize with the retinoid X receptor (RXR) and binds to the consensus regions on the target gene promoters and initiates transcription (Neumeister, 2013). Given that endoannabinoids activate PPAR-α (Marsicano et al., 2002; Pistis and Melis, 2010), the activation of these nuclear receptors represents a novel mechanism by which cannabinoids may modulate behavior. The endocannabinoid, N-palmitoylethanolamine (PEA) is a PPAR-α agonists, which is found decreased in PTSD patients (Wilker, S. et al., 2016). Recent preclinical findings showed that supplementing PEA in rodent PTSD models improves emotional behavior by enhancing allopregnanolone biosynthesis in corticolimbic glutamatergic neurons. This effect is mimicked by PPAR-α agonists and prevented by allopregnanolone biosynthetic enzyme blockers and by deletion of the PPAR-α gene (Locci and Pinna, 2017). Thus, anxiolytic, anti-aggressive and anti-fear effects of PEA and other synthetic cannabinoids that act as PPAR-α agonists may relate to an induction of corticolimbic allopregnanolone's biosynthetic enzymes, including CYP11A1 and 5α-reductase. This may result in potentiation of $GABA_A$ receptor signal transduction and improved behavioral dysfunction (represented in the bottom panel). Stress effects on PEA levels and probably expression of PPAR-α may result in the down-regulation of allopregnanolone's biosynthetic enzyme expression and allopregnanolone levels. The interface of the endocannabinoid and neurosteroid systems may provide an important biomarker axis to selectively predict, diagnose, and establish the best individualized treatment selection for PTSD patients.

FIG. 20 shows a schematic demonstrating the biomarker axis at the interface of the endocannabinoid and neurosteroid systems. In animal models of PTSD, protracted stress results in the downregulation of allopregnanolone biosynthetic enzymes (e.g., 5α-reductase type I, 5α-RI) and allopregnanolone concentrations in corticolimbic glutamatergic neurons of the frontal cortex, hippocampus, and basolateral amygdala. This allopregnanolone decrease correlates with behavioral dysfunction, such as increased aggression, enhanced contextual fear responses and anxiety-like behavior (Pinna et al., 2003; Pibiri et al., 2008). Supplying allopregnanolone or stimulating its biosynthesis decreases anxiety-like behavior, aggression and fear responses (Pinna, 2014; Pinna and Rasmusson, 2014). Stress may also result in changes in $GABA_A$ receptor subunit expression (Pinna et al., 2006; reviewed in Locci and Pinna, 2017a) with increased α4, α5 and δ subunits and decreased α1, α2 and γ2, which result in down-regulated benzodiazepine binding sites and inefficacy of benzodiazepine pharmacological action (Pinna et al., 2006; Nin et al., 2011b). Protracted stress results in increased $GABA_A$ receptor subunits, including $α_{4-6},β,δ$. highly sensitivity for allopregnanolone (Locci and Pinna, 2017a). Both allopregnanolone biosynthesis downregulation and decreased benzodiazepine binding sites have been reported in PTSD patients (Rasmusson et al., 2006; 2018; Geuze et al., 2008). Thus, the combination of downregulation of allopregnanolone biosynthesis, changes in GABAA receptor subunit expression, and lack of benzodiazepine pharmacological action are peculiar changes observed in PTSD that may provide a selective biomarker axis for this disorder. Stress may affect PEA levels and expression of PPAR-α which in turn may downregulate allopregnanolone concentrations. Thus, the PPAR-α-allopregnanolone axis may provide further biomarker candidates to support selection of the best individualized precision medicine for PTSD. Abbreviations: Allo, allopregnanolone; GABA, γ-aminobutyric acid; PEA, N-palmitoylethanolamine; PPAR-α, peroxisome-proliferator activated receptor-αStAR, steroidogenic acute regulatory protein; TSPO 18 kDa translocator protein.

REFERENCES FOR EXAMPLE 4

Altomare, G. & Capella, G. L. (2002) *J. Dermatol.* 29, 665-9.
Adamczyk P, Golda A, Przegaliński E. (2008). *J Physiol Pharmacol.* 59:217-28.
Agis-Balboa, et al. (2006) *Proc. Natl. Acad. Sci. USA* 103, 14602-7.
Agis-Balboa et al. (2007). *Proc. Natl. Acad. Sci. USA* 104, 18736-41.
Agis-Balboa R C, Guidotti A, Pinna G. (2014) *Psychopharmacology.* 231:3569-80. 2014.
Belelli, D. & Lambert, J. J. (2005) *Nat. Rev. Neurosci.* 6, 565-75.
Bernardy N C, Friedman M J. (2017) *Curr Opin Psychol.* 14:116-121.
Bernardy N C, Friedman M J (2015). *Curr Psychiatry Rep.* 17:564.
Brewin C R, et al. (2017). *Clin Psychol Rev.* 58:1-15.
Brown N, et al. (2002). *Br J Pharmacol* 136: 965-974.
Caruso, D. (2015). *J. Steroid Biochem. Mol. Biol.* 146, 74-9.
D'Agostino, G. (2007). *J. Pharmacol. Exp. Ther.* 322, 1137-43.
Dichtel L E, et al. (2018). *Neuropsychopharmacology*
Dlugos, A. (2012) *Neuropsychopharmacology* 37, 2416-27.
Fernandes B S, et al. (2017) *BMC Med.* 15:80.
Forman B M, Chen J, Evans R M (1996) *Ann N Y Acad Sci* 804, 266-75
Franklin C L, et al. (2017). *Psychiatry Res.* 261:504-507.
Geuze E, et al. (2008) *Mol Psychiatry* 13, 74-83.
Ghazizadeh-Hashemi, M. (2018). *J. Affect. Disord.* 232, 127-133.
Girdler, S. S. & Klatzkin, R. (2007) *Pharmacol. Ther.* 116, 125-39.
Golden R N, et al. (2002). *J Clin Psychiatry* 63: 577-584.
Heyman, E. (2012). *Psychoneuroendocrinology* 37, 844-51.
Hill, M. N. et al. (2009a) *Psychoneuroendocrinology* 34, 1257-62.
Hill M. N. et al. (2009b) *Trends Pharmacol. Sci.* 30, 484-93.
Hill, M. N. & Patel, S. (2013) *Biol. Mood Anxiety Disord.* 3, 19.
Häring M, Guggenhuber S, Lutz B. (2012) *Neuroscience.* 1; 204:145-58.
Hosie A M, Wilkins M E, da Silva H M, Smart T G (2006). *Nature* 444: 486-489.
Kanes S, et al. (2017). *Lancet.* 390:480-489.

Kamprath K, et al. (2006) J Neurosci 26(25), 6677-86
Katona, I. Behav. Neurosci 1, 65-86 (2009).
Kemp A H, Gordon E, Rush A J, Williams L M (2008). C N S Spectr 13: 1066-1086.
Jacob W, et al. (2012) Neurobiol Learn Mem 98(1), 47-55.
Locci, A. & Pinna, G. Br. J. Pharmacol. 174, 3226-3241 (2017).
Locci A, et al. (Editors) Nova Biomedical Publ. 2018.
Locci A, Pinna G. 165.19. 47th Annual Meeting Society for Neuroscience, Washington, D.C., USA, Nov. 11-15, 2017.
Lo Verme, J. et al. Mol. Pharmacol. 67, 15-9 (2005).
Lovick, T. J. Psychopharmacol. 27, 1180-5 (2013).
Malayev A, Gibbs T T, Farb D H (2002). Br J Pharmacol 135: 901-909.
Marsicano G, et al. (2002) Nature 418(6897), 530-4
Neumeister, A. et al. Psychoneuroendocrinology 51, 577-84 (2014).
Nemeroff C B (2008). Neuron 59: 185-186.
Nin S M, Martinez L A, Pibiri F, Nelson M and Pinna G: Front. 2011 Endocrin. 2:73.
Ngounou Wetie A G, et al. 2013 Jun. 5; 1(1):8
Nusser Z, Mody I (2002). J Neurophysiol 87: 2624-2628.
O'Sullivan S E (2007) Br J Pharmacol 152(5), 576-82.
Patel, S. et al. J. Lipid Res. 46, 342-9 (2005).
Park-Chung M, et al. 1999. 830(1):72-87.
Petrosino, S. & Di Marzo, V. Br. J. Pharmacol. 174, 1349-1365 (2017).
Pibiri, F. et al. Proc. Natl. Acad. Sci. USA 105, 5567-72 (2008).
Pineles, S. L., et al., Psychoneuroendocrinology (in press).
Pinna G and Izumi T: Pinna G. & Izumi T (Editors) Nova Biomedical Publ. 2018.
Pinna G, Rasmusson A. Front. Cell. Neurosci. 8:256.2014.
Pinna G. Targeting neurosteroidogenesis as therapy for PTSD. Front. Pharmacol. 2014
Pinna G and Rasmusson A M: J. Neuroendocrinology. 24:102-16. 2012
Pinna, G. et al. Proc. Natl. Acad. Sci. USA 100, 2035-40 (2003).
Pistis M, Melis M. (2010)Cur. Med Chem. 17:1450-67.
Rasmusson, A. M. et al. Biol. Psychiatry 60, 704-13 (2006).
Rasmusson A M, King M, Gregor K, Scioli-Salter E, Pineles S, Valovski I et al. (2016). Sex differences in the enzyme site at which GABAergic neuroactive steroid synthesis is blocked in PTSD: implications for targeting of PTSD therapeutics. 32nd Annual Meeting, International Society for Traumatic Stress Studies Dallas, Tex.
Rasmusson, A. M. et al. Neurosci. Lett. 649, 156-163 (2017).
Raso, G. M. et al. J. Neuroendocrinol 23, 591-600 (2011).
Reich C G, Mohammadi M H, Alger BbE. J Psychopharmacol. 2008; 22(7):769-77.
Riebe C J, Wotjak C T. Endocannabinoids and stress. Stress. 2011. 14(4):384-97.
Romeo, E. et al. Am. J. Psychiatry 155, 910-3 (1998).
Rush A J, et al. (2006). Biol Psychiatry 59: 493-501
Sasso, O., et al. Eur. Neuropsychopharmacol. 20, 195-206 (2010).
Sasso, O. et al. Pain 153, 33-41 (2012).
Schüle, C. et al. Neuroscience 191, 55-77 (2011).
Schüle, C. et al. TProg. Neurobiol. 113, 79-87 (2014).

We claim:

1. A method of treating a post-traumatic stress disorder (PTSD) in a subject in need thereof, the method comprising: administering an effective amount of an endocannabinoid PPARα agonist to the subject in need thereof, wherein the subject in need thereof has not responded to treatment with one or more selective-serotonin reuptake inhibitors.

2. The method of claim 1, wherein the endocannabinoid is arachidonoylethanolamine (AEA), oleoyldopamine (OEA), palmitoylethanolamide (PEA), stearoylethanolamide (SEA) or any combination thereof.

3. The method of claim 2, wherein the endocannabinoid is PEA.

4. The method of claim 3, wherein the effective amount of PEA can range from about 5 mg/kg to about 20 mg/kg.

5. The method of claim 1, further comprising the step of detecting a biomarker for PTSD in a sample from the subject in need thereof.

6. The method of claim 5, wherein the biomarker for PTSD is the amount of endogenous neurosteroids, endocannabinoids and their congeners, or the ratio thereof, in a bodily fluid sample of the subject in need thereof.

7. The method of claim 6, wherein the neurosteroid comprises allopregnanolone, allopregnanolone sulfate, pregnanolone sulfate, or a combination thereof.

8. The method of claim 6, wherein the endocannabinoids and their congeners comprises N-Palmitoylethanolamine (PEA), oleoyldopamine (OEA), stearoylethanolamide (SEA), N-arachidonoylethanolamine (AEA), or a combination thereof.

* * * * *